(12) United States Patent
Knox et al.

(10) Patent No.: US 9,702,803 B2
(45) Date of Patent: Jul. 11, 2017

(54) PARTICLE DETECTION

(71) Applicant: Xtralis Technologies Ltd., Nassau (BS)

(72) Inventors: Ron Knox, Mount Eliza (AU); Kemal Ajay, Mount Waverley (AU); Karl Boettger, Mount Waverley (AU)

(73) Assignee: GARRETT THERMAL SYSTEMS LIMITED, Berkshire (GB)

( * ) Notice: Subject to any disclaimer, the term of this patent is extended or adjusted under 35 U.S.C. 154(b) by 0 days.

(21) Appl. No.: 14/687,969

(22) Filed: Apr. 16, 2015

(65) Prior Publication Data

US 2015/0241330 A1    Aug. 27, 2015

Related U.S. Application Data

(63) Continuation of application No. 12/743,171, filed as application No. PCT/AU2008/001697 on Nov. 14, 2008, now Pat. No. 9,025,144.

(51) Int. Cl.
*G01N 21/00* (2006.01)
*G01N 15/06* (2006.01)
(Continued)

(52) U.S. Cl.
CPC ............ *G01N 15/06* (2013.01); *G01N 21/53* (2013.01); *G08B 17/125* (2013.01); *G08B 29/18* (2013.01);
(Continued)

(58) Field of Classification Search
CPC .......... G01N 15/06; G01N 2015/0693; G01N 21/53; G01N 15/0656; G01N 21/532;
(Continued)

(56) References Cited

U.S. PATENT DOCUMENTS 3,429,243 A    2/1969  Boyle, Jr.
3,688,298 A    8/1972  Miller et al.
(Continued)

FOREIGN PATENT DOCUMENTS

DE    3641716 A1    6/1988
EP    1300816 A1    4/2003
(Continued)

OTHER PUBLICATIONS

Communication dated Feb. 29, 2016, issued by the Canadian Intellectual Property Office in corresponding Canadian Application No. 2,705,830.
(Continued)

*Primary Examiner* — Tri T Ton
(74) *Attorney, Agent, or Firm* — Sughrue Mion, PLLC

(57) ABSTRACT

A particle detection system (100), such as an active video smoke detection system, includes at least one illumination means (102) for directing a beam (106) of radiation through at least part of the air volume being monitored (110), an image sensor (104) is positioned to capture images of at least part of a beam (106) from illumination means (102); and means to analyze (107) the captured images to detect the presence of particles within the volume. At least 29 different aspects are described for improving the sensitivity, usability, and robustness of particle detection. These include, for example, configuring illumination means (102) to create a curtain of light or a rapidly-scanned beam across the air volume (110), and configuring a reflector to steer or change direction of a beam reflected from illumination means (102).

24 Claims, 31 Drawing Sheets

(51) Int. Cl.
*G08B 17/12* (2006.01)
*G01N 21/53* (2006.01)
*H04N 5/32* (2006.01)
*H04N 7/18* (2006.01)
*G08B 29/18* (2006.01)

(52) U.S. Cl.
CPC ............... *H04N 5/32* (2013.01); *H04N 7/18* (2013.01); *G01N 2015/0693* (2013.01)

(58) Field of Classification Search
CPC .... G08B 17/125; G08B 29/18; G08B 17/107; H04N 5/32; H04N 7/18
USPC .................................................. 356/335–343
See application file for complete search history.

(56) References Cited

U.S. PATENT DOCUMENTS

| | | |
|---|---|---|
| 3,727,056 A | 4/1973 | Enemark |
| 3,737,858 A | 6/1973 | Turner et al. |
| 3,788,742 A | 1/1974 | Garbuny |
| 3,901,602 A | 8/1975 | Gravatt, Jr. |
| 3,915,575 A | 10/1975 | Sick |
| 3,924,252 A | 12/1975 | Duston |
| 4,594,581 A | 6/1986 | Matoba |
| 5,189,631 A | 2/1993 | Suzuki |
| 5,225,810 A | 7/1993 | Inoue et al. |
| 5,266,798 A | 11/1993 | Borden et al. |
| 5,381,130 A | 1/1995 | Thuillard et al. |
| 5,502,434 A | 3/1996 | Minowa et al. |
| 5,530,433 A | 6/1996 | Morita |
| 5,576,697 A | 11/1996 | Nagashima et al. |
| 5,646,390 A | 7/1997 | Wang et al. |
| 5,696,379 A | 12/1997 | Stock |
| 5,751,785 A | 5/1998 | Moorman et al. |
| 5,861,951 A | 1/1999 | Uesugi et al. |
| 5,912,619 A | 6/1999 | Vogt |
| 5,923,260 A | 7/1999 | Endo et al. |
| 6,091,345 A | 7/2000 | Howard et al. |
| 6,119,055 A | 9/2000 | Richman |
| 6,204,768 B1 | 3/2001 | Kosugi et al. |
| 6,292,683 B1 | 9/2001 | Gupta et al. |
| 6,509,832 B1 | 1/2003 | Bauer et al. |
| 6,658,203 B1 | 12/2003 | Oster et al. |
| 6,813,303 B2 | 11/2004 | Matsuda et al. |
| 7,983,445 B2 | 7/2011 | Knox et al. |
| 8,154,724 B2 | 4/2012 | Mitchell et al. |
| 8,406,471 B2 | 3/2013 | Knox et al. |
| 8,427,642 B2 | 4/2013 | Mitchell et al. |
| 8,508,376 B2 | 8/2013 | Knox et al. |
| 8,620,031 B2 | 12/2013 | Knox et al. |
| 2002/0070854 A1 | 6/2002 | Bartholomew et al. |
| 2002/0080040 A1 | 6/2002 | Schneider et al. |
| 2002/0118352 A1 | 8/2002 | Ohzu et al. |
| 2002/0135490 A1 | 9/2002 | Opitz et al. |
| 2002/0153499 A1 | 10/2002 | Oppelt et al. |
| 2003/0189487 A1 | 10/2003 | Mathews et al. |
| 2004/0017505 A1 | 1/2004 | Yamauchi |
| 2004/0051791 A1 | 3/2004 | Hashimoto |
| 2004/0056765 A1 | 3/2004 | Anderson et al. |
| 2004/0080618 A1 | 4/2004 | Norris et al. |
| 2004/0085448 A1 | 5/2004 | Goto et al. |
| 2005/0207655 A1 | 9/2005 | Chopra et al. |
| 2005/0259255 A1 | 11/2005 | Williams |
| 2006/0170787 A1 | 8/2006 | Bentkovski |
| 2006/0202847 A1 | 9/2006 | Oppelt et al. |
| 2007/0024459 A1 | 2/2007 | Cole |
| 2007/0064980 A1 | 3/2007 | Knox et al. |
| 2008/0061250 A1 | 3/2008 | Perel et al. |
| 2008/0297360 A1 | 12/2008 | Knox et al. |
| 2011/0058167 A1 | 3/2011 | Knox et al. |
| 2011/0221889 A1 | 9/2011 | Knox et al. |
| 2011/0243389 A1 | 10/2011 | Knox et al. |
| 2012/0038768 A1 | 2/2012 | Fukimori |
| 2012/0140231 A1 | 6/2012 | Knox et al. |
| 2013/0121546 A1 | 5/2013 | Guissin |
| 2013/0170705 A1 | 7/2013 | Knox et al. |
| 2014/0022547 A1 | 1/2014 | Knox et al. |
| 2014/0028989 A1 | 1/2014 | Butscher et al. |

FOREIGN PATENT DOCUMENTS

| | | |
|---|---|---|
| GB | 2426323 A | 11/2006 |
| JP | S5387283 A | 8/1978 |
| JP | S5622932 A | 3/1981 |
| JP | 62153780 | 7/1987 |
| JP | H03245296 A | 10/1991 |
| JP | 05-288668 A | 11/1993 |
| JP | H06109631 A | 4/1994 |
| JP | H0712724 A | 1/1995 |
| JP | 10154284 A | 9/1998 |
| JP | H10232196 A | 9/1998 |
| JP | H11503236 A | 3/1999 |
| JP | 11339150 A | 12/1999 |
| JP | 2000-019112 A | 1/2000 |
| JP | 2000180349 A | 6/2000 |
| JP | 200250769 A | 9/2002 |
| JP | 2004-257876 A | 9/2004 |
| JP | 5-020563 B2 | 1/2012 |
| WO | 2004102498 A1 | 11/2004 |
| WO | 2006/050570 A1 | 5/2006 |

OTHER PUBLICATIONS

EP Search Report dated Jun. 5, 2013 issued in EP 12183148.1.
EP Search Report dated Jun. 20, 2013 issued in EP 12183185.3.
EP Search Report dated Jul. 2, 2013 issued in EP 12183207.5.
Office Action dated Jan. 7, 2010 issued in U.S. Appl. No. 10/556,807.
Office Action dated Mar. 17, 2009 issued in U.S. Appl. No. 10/556,807.
Office Action dated Aug. 8, 2010 issued in U.S. Appl. No. 10/556,807.
Allowance dated Mar. 15, 2011 issued in U.S. Appl. No. 10/556,807.
Restriction dated Oct. 19, 2011 issued in U.S. Appl. No. 13/164,123.
Office Action dated May 14, 2012 issue din U.S. Appl. No. 13/164,123.
Allowance dated Nov. 23, 2012 issued in U.S. Appl. No. 13/164,123.
Office Action dated May 8, 2013 issued in U.S. Appl. No. 13/775,577.
Allowance dated Aug. 23, 2013 issued in U.S. Appl. No. 13/775,577.
Office Action dated Jan. 27, 2012 issued in U.S. Appl. No. 11/719,226.
Office Action dated May 29, 2012 issued in U.S. Appl. No. 11/719,226.
Allowance dated Apr. 8, 2013 issued in U.S. Appl. No. 11/719,226.
Restriction dated Feb. 15, 2012 issued in U.S. Appl. No. 12/743,171.
Office Action dated Jan. 14, 2014 issued in U.S. Appl. No. 12/743,171.
Office Action dated Jun. 20, 2014 issued in U.S. Appl. No. 13/936,418.
Communication dated Mar. 20, 2015 from the European Patent Office in counterpart European Application No. 08849716.9.
English Translation of communication dated May 26, 2015 from the Japanese Patent Office in counterpart application No. 2014-148142.
European Patent Office Search Report and Opinion; Application No. 08 849 716.9; Nov. 1, 2011.
Communication dated Jun. 3, 2014 from the Japanese Patent Office in counterpart Japanese Patent Application No. 2013-055559.
Communication dated Jun. 10, 2014 from the Japanese Patent Office in counterpart Japanese Patent Application No. 2013-096833.
Communication dated Jun. 3, 2014 from the Japanese Patent Office in counterpart Japanese patent Application No. 2010-196936.
EP Search Report dated Jan. 24, 2013 issued in EP 12182832.1.
EP Search Report dated May 10, 2013 issued in EP 12183197.8.

(56) References Cited

OTHER PUBLICATIONS

EP Search Report dated May 15, 2013 issue din EP 12183106.9.

1. LIGHT SOURCE
2. OUTWARD BEAM
3. ILLUMINATION SPOT
4. SCATTERED LIGHT
5. RETURNED LIGHT
6. RECEIVING DETECTOR

PARTICLE DETECTION

CROSS REFERENCE TO RELATED APPLICATIONS

This application is a Continuation of application Ser. No. 12/743,171 filed on Oct. 19, 2010 which is a National Stage of International Application No. PCT/AU2008/001697 filed Nov. 14, 2008, claiming priority based on Australian Patent Application No. 2007906260, filed Nov. 15, 2007, the contents of all of which are incorporated herein by reference in their entirety.

FIELD OF THE INVENTION

The present invention relates to systems and methods applicable to particle detection systems. The preferred embodiment of the present invention relates to systems and methods adapted to detect smoke, and more particularly to systems and methods applicable to active video smoke detection. While it is convenient to describe the present invention in this context, the present invention should not be seen as being limited to that exemplary field of application.

BACKGROUND OF THE INVENTION

Active video smoke detection (AVSD) is the name that has been coined by Xtralis Pty Ltd for particle detection systems (most preferably smoke detection systems) that use video analysis techniques to detect smoke in an air volume that is actively illuminated, e.g. by a laser or other electromagnetic (EM) radiation source.

Systems and methods for performing AVSD have been described in international patent publications WO 2004/102498 and WO 2006/001723 in the name of VFS Technologies Pty Ltd, the contents of which are incorporated herein by reference for all purposes.

The basic system disclosed in those documents is one in which a laser beam is directed across an air volume being monitored. An image sensor is positioned such that it can capture images of at least part of the beam. The captured images are analysed to determine whether smoke is present in the volume by determining the level of scattered EM radiation captured in the images.

As noted in those patent publications one problem that may be faced by such system is that of objects other than smoke entering the beam or field of view of the image sensor. This can have several effects; firstly it can cause a false alarm by imitating the effect of smoke. Secondly, encroaching objects may prevent the system from detecting smoke by blocking the path of the beam across the volume being monitored or by blocking the view of part of the beam by the image sensor. Thirdly, it may be unsafe if a person (or animal) passes through the beam. Thus, such systems need mechanisms and methods for both preventing the encroachment of objects into the beam, and for the amelioration of the negative effects on the system when such an encroachment occurs.

Another issue to consider is the set-up and maintenance of such a system. An AVSD system will typically have a EM radiation source shining a EM radiation beam across an extended distance. In most circumstances system components will need to be accurately aligned across this extended distance. Alignment of the components will need to be performed at commissioning and periodically during the operation of the system to ensure correct operation.

Due to the relative difficulty in controlling the environment in air volumes suited to the use of an AVSD system, e.g. large areas, high roofed enclosed areas such as atriums etc. an AVSD system must be sufficiently robust to cope with a wide range of environments. For example such environments often have a wide range of possible background light levels, e.g. differences in lighting levels between day and night, and may also have rapidly fluctuating background light levels.

Accordingly there is a need for methods and systems for improving the sensitivity, usability, and robustness of AVSD systems. Other objects and aspects of embodiments of the present invention will become apparent from the following description.

It is not admitted that any of the information in this specification is common general knowledge, or that the person skilled in the art could be reasonably expected to have ascertained, understood, regarded it as relevant or combined it in anyway at the priority date.

SUMMARY OF THE INVENTION

In the present specification an AVSD system should be understood to refer to a particle detection system adapted to detect particles directly in a volume being monitored, the system including at least one illumination means (also called a primary light source) for directing a beam of radiation through at least part of the air volume being monitored, an image sensor is positioned to capture images of a least part of a beam from an illumination means; and means to analyse the captured images to detect the presence of particles within the volume on the basis of radiation captured in the images.

The term light should be interpreted to include any wavelength electromagnetic (EM) radiation, including radiation falling in the visible spectrum and non-visible parts of the EM spectrum, such as infra-red, ultraviolet, or longer or shorter wavelength bands. In certain embodiments, the light used will be confined to a narrow band, whereas in other embodiments the light will cover a wide bandwidth.

The beam can be of any geometry, including, collimated, planar, divergent.

An AVSD system may include plurality of primary light sources and/or a plurality of sensors arranged to monitor the volume from different perspectives. An AVSD system may additionally include one or more secondary light sources used for a purpose other than primary particle detection.

The primary light source may be a laser, laser diode, LED or other sufficiently intense light source. In some embodiments, it will be advantageous for the light source to produce coherent light however, this may not be essential, or even desirable in all embodiments.

The light sensor may be a video camera or the like, or a purpose-built light sensor including means for converting a received optical signal into an electrical signal and optionally light receiving optics associated therewith. The light sensor may additionally include one or more filters or polarising optics in certain embodiments of the present invention.

In the specification and claims the term 'region of interest' are used to refer to region of intersection between the light emitted by a primary light source (whether emitted directly or by reflection) and the field of view of the corresponding sensor, and from which scattered light is to be received by the sensor.

A light source of the AVSD system may include one or more optical components adapted to provide the light emitted by the light source with one or more predetermined characteristics. For example, the optical components may include collimators, focussing or defocusing lenses, mirrors, prisms or the like, configured to give the emitted light beam a predetermined characteristic.

In a preferred form an AVSD system is a smoke detector.

In the first aspect the present invention provides a particle detection system configured to detect particle in an air volume, the system including: illumination means for directing a beam of radiation across the air volume being monitored, an image sensor is positioned to capture images of a least part of the beam; means to analyse the captured images to detect the presence of particles within the volume on the basis of scattered radiation captured in the images; a light source configured to illuminate a surface providing a background to at least an extended part of the volume being monitored; and a light sensor adapted to receive light reflected from the background surface; means for analysing the output of the light sensor to determine the presence of a shadow cast on the background surface.

Preferably the means for determining the presence of a shadow include, means for storing a pre-recorded reference image and means for comparing the light sensor output to the pre-recorded reference image to determine the presence of a shadow.

Preferably the system includes fault notification means for raising a fault condition if a shadow is detected. The fault notification means includes means for determining a duration of a fault condition, and wherein the system is configured raise a fault condition if the fault condition lasts for a predetermined duration.

The surface can be illuminated using an un-collimated or divergent beam in certain embodiments of the present invention. The light source configured to illuminate a surface can be additionally used for particle detection. The light source can project a collimated beam of radiation into the volume and is scanned across the volume to illuminate an extended portion of the surface. The light source can project an un-collimated or divergent beam.

In a second aspect the present invention provides a method for identifying the presence of an object in at least part of the field of view of a light sensor of an AVSD system, the method including:
illuminating at least part of a surface within the field of view of the light sensor;
analysing the output of the light sensor to determine a change in the illumination of the surface; and
identifying the presence of an object if the output of the light sensor meets one or more predefined criteria.

The step of analysing the output of the light sensor can include, comparing an output of the light sensor to a reference output of the light sensor.

Preferably the step of analysing includes, determining the presence of at least one shadow in the output of the light sensor that is not present in the reference output.

The surface can be illuminated using an un-collimated or divergent beam in certain embodiments of the present invention. Alternatively, a collimated beam and the method includes, scanning the beam across the surface to illuminate a wide portion of the surface.

In another aspect the present invention provides a particle detection system configured to detect particle in an air volume, the system including: primary illumination means for directing a beam of radiation across the air volume being monitored, a primary image sensor is positioned to capture images of a least part of the beam; said primary illumination means and primary image sensor being positioned on non-opposing sides of the volume being monitored; at least one reflector configured to direct light emitted by the primary light source to a predetermined target position such that the light traverses a path across at least part of the volume being monitored; means to analyse the captured images to detect the presence of particles within the volume on the basis of scattered radiation captured in the images.

In a further aspect the present invention provides: an AVSD system comprising particle detection system configured to detect particle in an air volume, the system including:
a primary light source mounted on a first side of a volume being monitored and configured to emit a beam of radiation;
a reflector configured to receive an incident beam received from the primary light source and to reflect a reflected beam, said reflector being positioned such that at least the reflected beam traverses a volume being monitored by the system; and light sensor mounted such that it is able to receive light scattered from a reflected beam in a forward scattering geometry, means to analyse the output of the light sensor to detect the presence of particles within the volume on the basis of scattered radiation.

Preferably the primary light source and primary light sensor are located on a same side of the volume being monitored.

The primary light source and primary light sensor can be substantially co-located. The primary light source and primary light sensor can also be mounted in the same housing.

Preferably the field of view of the primary light sensor includes at least part of the beam incident on the reflector and the reflected beam. The field of view of the primary light sensor can include a predetermined target position.

The reflector can include a plurality of reflective surfaces. The reflector is preferably a corner reflector adapted to reflect a beam of light at a substantially fixed angle to an incident beam.

Either the light source or one or more of the reflectors can be steerable to change the path of the incident or reflected beam.

The system can further include a second light sensor positioned to receive the reflected beam.

Preferably at least a portion of the reflected beam traverses a volume being monitored.

In another aspect the present invention provides an AVSD system including a marker light source that emits a beam of radiation, the system including: illumination means for directing at least one beam of radiation across the air volume being monitored, an image sensor is positioned to capture images of a least part of the beam; means to analyse the captured images to detect the presence of particles within the volume on the basis of scattered radiation captured in the images; wherein the system wherein at least one of said beams of radiation is a marker beam that enables the light sensor to determine the path of the beam through the volume in the substantial absence of particles intended to be detected by the system.

Preferably the system includes a secondary light source to emit the marker beam. Preferably the marker beam includes a wavelength component that produces scattering from particles smaller than those particles intended to be detected by the system, at a wavelength within a light reception band of the light sensor.

The marker beam can be a short wavelength beam of light. The marker beam can be a beam of blue or ultraviolet light. The marker beam could be a beam produced by a primary light source.

In another aspect the present invention provides a particle detection system configured to detect particle in an air volume, the system including: illumination means for directing at least one beam of radiation across the air volume being monitored, said at least one beam including two or more wavelength components, an image sensor is positioned to capture images of a least part of the beam; means to analyse the captured images to detect the presence of particles within the volume on the basis of scattered radiation captured in the images.

Preferably a scattering signal from at least two wavelength components can be determined.

The scattering signal at, at least two wavelengths can be processed to determine data relating to the particle size distribution in the volume being monitored.

The marker beam can be in a visible band of the electromagnetic spectrum.

The system can includes at least one primary light source that emits a beam of light in a known positional relationship to the source of the marker beam.

The system can include primary light source to emit a first beam of light for use in the detection of particles and a marker light source for generating the marker beam, wherein the primary light source and marker light source are mounted in a common housing in a predefined positional relationship.

The marker beam and primary beam may be arranged in one of the following relationships: the beams are co-axial; the beams are parallel.

The primary light beam can be outside the visible band of the electromagnetic spectrum. The marker light source can be illuminated intermittently.

In another aspect the present invention provides a light source arrangement for an particle detection system including a light emitting element configured to emit a light beam in a first direction and a reflector positioned to reflect at least part of the beam emitted from the light emitting element, said light emitting element and reflector being mounted such that the relative orientation of the light emitting element and reflector can be varied to steer the beam reflected off the reflector.

Preferably the relative orientation of the light emitting element and reflector can be varied in two dimensions.

The light source arrangement can further include a light sensor configured to receive a beam of light. Preferably the light sensor is mounted in a position relative to the reflector such that the beam of light received by the light sensor is reflected off the reflector.

In a further aspect of the present invention there is provided a particle detection system configured to detect particle in an air volume, the system including: illumination means including a light source as claimed in any one of claims 1 to 4 for directing a beam of radiation across the air volume being monitored, an image sensor is positioned to capture images of a least part of the beam; means to analyse the captured images to detect the presence of particles within the volume on the basis of scattered radiation captured in the images.

The system can further includes a reflective target arranged to reflect at least one beam of light emitted from the light source.

The reflective target includes a retro-reflective portion configured to reflect light in a path substantially opposite its path of incidence on the retro-reflective portion. The system may include a secondary light source positioned in a known physical relationship to the light source arrangement.

In a further aspect the present invention provides a method of determining alignment of a beam in an AVSD system, the method including: emitting a beam of light across a volume being monitored; scanning the beam of light across a predetermined area; receiving at least a portion of the beam of light at a light sensor; and based on at least one measured parameter of the received light determining an alignment of the beam of light.

The measured parameter can include any one or more of the following characteristics: light intensity, spot size, total received irradiance, a light intensity pattern.

The method preferably includes reflecting at least a portion of the light beam from a reflector, back toward a light sensor such that either the emitted beam or reflected beam traverse the volume being monitored.

The step of scanning the beam of light can include scanning the beam over a predetermined angular range, or a predetermined linear range or area at the target.

The method can include the step of: analysing the light received as a result of scanning of the beam to identify a light reception pattern characteristic of a reflection from a reflector forming part of the AVSD system.

The reflector can include an optical characteristic that give its light reflection at least one detectable characteristic. For example the optical characteristics of the reflector can include means for forming a detectable pattern in light reflected from the reflector caused by a reflectivity, refraction and/or diffraction characteristic of at least part of the reflector.

Preferably the detectable pattern is caused by any one or more of the following: a change of reflectivity across reflector; a bar-code, pattern, a hologram, a known reflection spectrum.

The method can subsequently include, on the basis of the determined alignment, changing the alignment of the beam of light so that the beam is aligned in a predetermined manner.

The step of scanning the beam of light across a predetermined area can include scanning the beam in a predetermined pattern. For example, the pattern can be a linear patter, raster pattern, spiral pattern, or other pattern.

In a further aspect the present invention provides a method of determining alignment of a beam in an AVSD system, the method including: detecting light emitted from either a primary or second the secondary light source with a light sensor; and based on at least one measured parameter of the received light, determining an alignment of the beam of light.

The measured parameter can include any one or more of the following characteristics: light intensity, spot size, total received irradiance, a light intensity pattern.

The step of detecting light emitted from either a primary or second light source with a light sensor includes scanning either of the light beams across a light sensor in a predetermined pattern. For example, the pattern can be any one or more of the following patterns; a linear patter, a raster pattern, a spiral pattern, or other pattern.

The method can subsequently include, on the basis of the determined alignment, changing the alignment of a beam of light emitted by a system so that the beam is aligned in a predetermined manner.

In a further aspect there is provided particle detection system including a primary light source, at least one light sensor configured to detect light scattered from the beam from the primary light source, and a reflector configured such that at least a portion of the beam from the primary light is reflected across the volume being monitored toward the light sensor, wherein the reflector is configured to enable the direction of the beam reflected from it to be changed. Preferably the reflector is steerable about at least one axis.

Preferably the reflector is steerable about 2 axes. The primary light source can include a beam alignment mechanism to allow the alignment of the beam emitted to be changed.

The invention can also provide a method in an AVSD system including: aligning a beam emitted from a light source with a reflector to within a first predetermined tolerance; reflecting the beam toward a predetermined point within a second predetermined tolerance.

The method can include moving the light source to align the beam with the reflector and/or moving the reflector to align the beam with the predetermined point. The second predetermined tolerance can be tighter than the first predetermined tolerance.

In another aspect the present invention provides a method in an AVSD system including: detecting a presence of scattered light over a period of time; analysing at least one characteristic of the sensed light over at least a portion of the volume to determine whether the light has been scattered by solid object or particles in the volume being monitored.

The method can include analysing a position dependent scattering characteristic to determine whether the light has been scattered by solid object or particles.

The method can include analysing an intensity profile of the received light over time or space to determine the presence of a solid object. The method can also include analysing the detected light to identify a characteristic of detected light signifying an edge of a solid object. The method can further include scanning a beam from a primary light source across an extended portion of the volume and detecting light scattered from the swept beam.

The method can include repeating any one or more of the above steps to confirm that an edge of a solid object has been detected.

The method can include indicating a fault if a solid object is detected.

In a further aspect there is provided a method in an AVSD system including: modulating the intensity of emission of a light source: and modulating the sensitivity of a corresponding sensor such that the sensitivity of the sensitivity of the light sensor is reduced from a peak value at the time or arrival of a peak in intensity of the emitted light.

In another aspect the present invention provides a method of monitoring for obstructions on surface of an optical component of an AVSD system illuminating an area adjacent the surface so as to illuminate an obstruction on the surface of the optical component; detecting light reflected from the illuminated obstruction.

In another aspect the present invention provides a particle detection system including a primary light source for emitting a beam of radiation into a volume being monitored; means for determining the intensity of the light received from the primary light source after traversing the volume being monitored; and a supervising system adapted to determine if the beam is at least partly obscured by an intrusion on the basis of the determined light intensity. The means for determining the intensity of the light received from the primary light source can be a photo-detector. The system can include a reflector to reflect the beam towards the means for determining the intensity of the light received from the primary light source.

The supervising system can be configured to decrease the level of light emitted from the primary light source in the event that an intrusion is detected.

In another aspect the present invention provides a method of supervising a beam of an AVSD system, the method including: monitoring an intensity of light received from a primary light source; and in an event that a decrease in intensity of received light is detected, determining that an intrusion into the beam path has occurred.

The method can include reducing the beam power in the event an intrusion has been detected. The method can include reflecting the beam across the volume being monitored.

In another aspect the present invention provides a method of maintaining alignment of a primary light source in an AVSD system including: monitoring an intensity of light received from a primary light source; and adjusting the alignment of the primary light source to attempt to achieve a predetermined light intensity characteristic.

In one embodiment the predetermined light intensity characteristic is based on either or both of: a predetermined intensity level, and a substantially constant intensity level.

The method can include reflecting the light from the primary light source to means for detecting the intensity of the reflected beam.

Adjusting the alignment of the primary light source can include at least one of: changing a direction of emission of the light source; and changing the angle of reflection from a reflector.

In one aspect the present invention provides a component for a particle detection system, said component including a housing and a tilt sensitive element mounted in a fixed relationship to housing. For example the tilt sensitive element can include one of more of the following: an accelerometer, capacitive tilt sensor, electrolytic tilt sensor, gas bubble in liquid tilt sensor, mercury tilt sensor, and pendulum tilt sensor.

The component can include a chassis having one or more optical components mounted to it. The housing can include a window through which light may pass to or from the optical component.

The tilt sensitive element can be communicatively coupled to a control system to detect tilting of the component. The component can include a plurality of tilt sensitive elements arranged to monitoring tilting of the component in more than one direction.

In another aspect the present invention provides a method in an AVSD system for determining intrusion of an object into the field of view of the light sensor, the method including: emitting a beam of light across at least part of the field of view of the light sensor; analysing the output of the light sensor to determine whether an object has impinged upon the beam of light.

The step of emitting a beam of light across at least part of the file of view of the light sensor includes, scanning a linear beam of light across part of the volume being monitored.

The step of analysing the output of the light sensor, can include identifying the presence of any one of the following features in the sensor output: a shadow, reflection, refraction, diffraction pattern or glint.

The method can include providing a secondary light source for monitoring a portion of the field of view of the image capture device affected by a primary light source. Preferably the method includes providing a secondary light source covering an extended area of the field of view of the light sensor, and analysing the output of the light sensor to determine the presence of objects intervening between the secondary light source and the image capture means.

In another aspect the present invention provides a method of checking for objects impinging on a field of view of an image sensor of an AVSD system, including: illuminating a region of the volume being monitored using a light source;

analysing the output of the image sensor to identify the object on the basis of either a reflection or shadow from the object.

The method includes scanning a light beam across a portion of the volume being monitored to at least temporarily illuminate a region of the volume between a primary beam position and the image capture means to attempt to identify objects blocking the line of sight between the image capture means and the light beam when it is in its primary beam position.

In another aspect the present invention provides a method in an AVSD system, for detecting intrusions into a volume being monitored by the system, the method including: capturing a plurality of images of at least part of the volume being monitored; determining at least one feature of the in the image that is in or behind a portion of the volume being monitored that is substantially time invariant; and analysing subsequent images including the feature; and in the event that the feature changes appearance; indicating at least a potential intrusion into the volume.

The feature can be a background feature lying behind a primary beam in the field of view of the image sensor.

The method can include illuminating the background. The illumination is preferably non-visible.

The step of illuminating the background can include providing a plurality of secondary light sources to illuminate the background. Preferably the secondary light sources are LEDs.

The step of illuminating the background can includes projecting a pattern of light onto a background surface.

In an embodiment in which a pattern is projected onto a background surface the method can include: attempting to recognise the pattern in at least one image, and in the event that an expected portion pattern is not visible, determining that an intrusion into the region of interest has occurred.

In a further aspect the present invention provides method of identifying an object in a volume being monitored by an AVSD system, the method including: (a) capturing images of the volume from at least two spatially separated positions, (b) identifying a suspected intruding objection in the image from one of the positions; and (c) identifying the same object in an image from another position taken at approximately the same time as the first image and calculating a position of the suspected intruding object.

The method can include, repeating the steps a to c to track the suspected intruding object.

The method can include raising a fault condition if an intruding object is identified.

In another aspect the present invention provides a particle detection system configured to detect particle in an air volume, the system including: illumination means for directing a beam of radiation across the air volume being monitored, a plurality of image sensors configured to capturing images with overlapping fields of view, one or more of said image sensors being positioned to capture images of a least part of the beam; means to analyse the captured images to detect the presence of particles within the volume on the basis of scattered radiation captured in the images; and intrusion detection means configured to analyse the output of the cameras and identify a suspected intruding objection in the image from one of the cameras; and to identify the same object in an image from the other camera taken at approximately the same time as the first image and to calculate a position of the suspected intruding object.

At least one of the cameras can also be a primary image capture sensor of system.

In another aspect the present invention provides a particle detection system configured to detect particle in an air volume, the system including: a first primary light source and a first light sensor positioned to detect light scattered from a beam of the first light source; a second primary light source and a second light sensor positioned to detect light scattered from a beam of the second light source; means to analyse the captured images to detect the presence of particles within the volume on the basis of scattered radiation captured in the images, and wherein the system geometry is such that the first light sensor is arranged to supervise a region between the first light source and the second light sensor, and the second light sensor is arranged to supervise a region between the second light source and the first light sensor.

The system can also include one or more secondary light sources extending between the first primary light source and second image capture device, and one or more secondary light sources extending between the second primary light source and first image capture device.

An aspect of the invention also provides a component of an for a particle detection system of the previous embodiment of the present invention, said component including, in a common housing in which is mounted a primary light source, and an image capture means, and one or more secondary light sources between them. Preferably the image capture device and light sources are arranged in a linear arrangement. The secondary light sources can be an array of LEDs, a fluorescent tube or other extended light source. The secondary light sources can form substantially uniform linear illumination pattern or an intermittent illumination pattern.

The component can be configured such that the primary light source is adapted to operate as the first primary light source, and an image capture means is adapted to operate as the second image capture means.

In another aspect the present invention provides a method in a particle detection system configured to detect particle in an air volume, the system including: a primary illumination means for directing a beam of radiation across the air volume being monitored, an image sensor is positioned to capture images of a least part of the beam; means to analyse the captured images to detect the presence of particles within the volume on the basis of scattered radiation captured in the images; and at least one secondary illumination means which emits light at least partly in the visible part of the electromagnetic spectrum, the method including: detecting an ambient light level: setting the light intensity of the secondary light source on the basis of the ambient light level so as to minimise the level of visibility of the light from the secondary light source, but maintain detectability of light from the secondary light source by a light sensor of the system.

The step of setting the light intensity of the secondary light source can include selecting one of a plurality of predetermined intensity levels.

In another aspect the present invention provides a particle detection system configured to detect particle in an air volume, the system including: illumination means for directing a beam of radiation across the air volume being monitored, an image sensor is positioned to capture images of a least part of the beam; means to analyse the captured images to detect the presence of particles within the volume on the basis of scattered radiation captured in the images, wherein at least one component of the system is polarisation selective.

The particle detection system is preferably adapted to detect particles using a predetermined polarisation of electromagnetic radiation. Preferably the system can be configured to detect particles in two polarisation states. One or both of a light source, or light sensor of the system can operate in a polarisation selective manner. The at least one illumination means is optionally adapted to emit a polarised light beam.

An illumination means can be configured to receive light having (one or more) selected polarisations.

In another aspect the present invention provides a method in a particle detection system configured to detect particle in an air volume, the system including: illumination means for directing a beam of radiation across the air volume being monitored, an image sensor is positioned to capture images of a least part of the beam; means to analyse the captured images to detect the presence of particles within the volume on the basis of scattered radiation captured in the images, the method including: measuring at least one scattered light component with at least one characteristic polarisation property; and processing said measurements to determine at least one characteristic of one or more airborne particles or objects within the volume being monitored.

The method can include detecting light in a plurality of polarisation states from which a characteristic of the airborne particles or objects within the volume being monitored can be determined. The method can include measuring the relative signal strengths in two polarisation states. One of the polarisation states may be an unpolarised or circularly polarised state.

The method can include using a primary light source to emit light with a known polarisation; and measuring light scattered light with a known polarisation selectivity.

The characteristic of the airborne particles measured can include one or more of the following: a concentration of particles above a determined size; a concentration of particles below a determined size, a concentration of particles falling within a size range. Advantageously this method can be used to detect the presence of large particles or objects in the path of the light beam.

In another aspect the present invention provides a method of detecting particles having a predetermined size profile, including: emitting a beam of light with a known polarisation state across a volume in which said particles are to be detected; measuring light scattered from the beam having a predetermined polarisation state; such that the relative polarisation of the emitted and measured light are selected to enable selective detecting particles having a predetermined size profile.

In another aspect the present invention provides a method of detecting objects intruding into a beam from a light source of an AVSD system, the method including: emitting a beam of light with a known polarisation state across a volume; measuring light scattered from the beam having a predetermined polarisation state, such that the relative polarisation of the emitted and measured light are selected to enable selective detect objects above a predetermined size.

In the above aspects the relative polarisation of the emitted and measured light can preferably be parallel or orthogonal. They may be at some intermediate angle, but this may reduce selectivity.

When the relative polarisation of the emitted and measured light are parallel the method can be adapted to measure particles having a size less than a predetermined level. When the relative polarisation of the emitted and measured light are orthogonal (i.e. cross polarised) the method can be adapted to measure particles or objects having a size greater than a predetermined level.

The method includes measuring light from the beam at a plurality of predetermined polarisation states. Each polarisation state is preferably measured independently.

The method can include using the measurements at each of the polarisation states to determine a characteristic of the particles in the air of the volume or a correction factor to be used in subsequent processing.

In another aspect the present invention provides a method of dust rejection in an particle detection system including, detecting particles having a predetermined size profile that substantially excludes dust, using a method of the previous aspect of the present invention.

In another aspect the present invention provides a light sensor for an particle detection system including, a light sensitive element with a polarisation sensitive element, said the light sensitive element being configured to enable only predetermined polarisations of light to reach the light sensitive element. The polarisation angle(s) of the polarisation sensitive element can preferably be changed. Preferably the polarisation sensitive element is a polarisation filter.

In another aspect the present invention provides a particle detection system as including a light sensor as described above.

The system can include a polarised light source for emitting light of a known polarisation.

The system can include a light sensor capable of measuring multiple polarisations of light. The light sensor can be configured to selectively measure multiple polarisations of light, alternatively the sensor is adapted to measure the multiple polarisations simultaneously. The light sensor can include a plurality of light receiving subsystems capable of receiving respective polarisations of light.

In another aspect the present invention provides a particle detection system configured to detect particle in an air volume, the system including:
a primary illumination means for directing a beam of radiation across a first air volume being monitored,
an image sensor is positioned to capture images of a least part of the beam; means to analyse the captured images to detect the presence of particles within the volume on the basis of scattered radiation captured in the images; air circulation means configured to move air from a second volume into the first volume to enable particles in the second volume to be detected.

In a preferred form the first volume and second volumes are substantially separate air volumes.

The first and second air volumes can be one or more of the following: neighbouring rooms; a room and an equipment cabinet.

The circulation means can include a fan configured to draw air through an aperture in a wall between the first and second air volume. The circulation means is preferably configured to introduce air from the second volume into the first volume either into the beam or adjacent the beam emitted from a primary light source of the particle detection system.

In a further aspect the present invention provides a method of monitoring a plurality of air volumes with a particle detection system arranged to monitor one of the volumes, the method including: drawing air from the second air volume into the first air volume, such that particles in the second volume will be detected by the particle detection system.

The particle detection system can be configured to detect particle in an air volume, the system including: illumination means for directing a beam of radiation across the air volume being monitored, an image sensor is positioned to capture images of a least part of the beam; means to analyse the captured images to detect the presence of particles within the volume on the basis of scattered radiation captured in the images.

In another aspect the present invention provides a smoke detection system including a primary smoke detection sub-system and a second particle detection sub-system configured to detect particle in an air volume, the system including: illumination means for directing a beam of radiation across the air volume being monitored, an image sensor is positioned to capture images of a least part of the beam; means to analyse the captured images to detect the presence of particles within the volume on the basis of scattered radiation captured in the images.

The system can further include an alarm subsystem adapted to raise an alarm if smoke is detected, the alarm sub-system being configured to raise a first, lower level alarm upon detection of smoke by the second particle detection sub-system and to raise a second, higher level alarm upon detection of smoke by the primary smoke detection system. Preferably the primary smoke detection sub-system is a standards approved smoke detection system. Most preferably the primary smoke detection sub-system is an aspirated smoke detection system.

In another aspect the present invention provides a method in a particle detection system configured to detect particle in an air volume, the system including illumination means for directing a beam of radiation across the air volume being monitored, an image sensor is positioned to capture images of a least part of the beam; means to analyse the captured images to detect the presence of particles within the volume on the basis of scattered radiation captured in the images the method including monitoring a light beam of an system to detect changes in a received signal caused by changes in the refractive index of part of the path of the beam to identify a heat source within the volume.

In another aspect the present invention provides a method of detecting fire including: shining a laser beam across a volume being monitored; and monitoring the light beam to detect changes in a received signal caused by changes in the refractive index of part of the path of the beam to identify a fire within the volume.

Preferably, the method includes detecting, at least one of: rapid changes in the alignment of the beam at a target; and changes in received intensity a target.

In another aspect the present invention provides a method in a particle detection system configured to detect particle in an air volume, the system including: illumination means for directing a beam of radiation across the air volume being monitored, an image sensor is positioned to capture images of a least part of the beam; means to analyse the captured images to detect the presence of particles within the volume on the basis of scattered radiation captured in the images, the method including: collecting light from a field of view including at least part of the beam, to collect light scattered from the beam by particles in the volume, with a first image sensor; and collecting light from substantially the same field of view in a manner that substantially excludes light scattered from the beam by particles in the volume, with a second light sensor.

Preferably the steps of collecting light by the first and second light receiving portions of the system are performed simultaneously.

Preferably, the first and second light receiving portions of the system form part of the same light sensor of the particle detection system. In a particularly preferred form, the first and second light receiving portions of the particle detection system are portions of a common imaging chip.

The method can include filtering the light arriving at the second light receiving portion. The filter is preferably a narrow band wavelength filter or polarisation filter.

The method can include receiving light at an optical system of the system and spitting the received light for separate reception at the first and second light receiving portions.

In another aspect the present invention provides a light sensor for an particle detection system including light receiving optics configured to split an image into two paths, one of said paths including a filter to prevent transmission of light having a particular characteristic that is transmitted in the other path. The light sensor can include a common light sensitive element arranged to simultaneously receive light from each path at different portions thereof.

The filter is preferably a wavelength filter or polarisation filter. The other path may additionally include a filter having a different filtering characteristic.

In another aspect the present invention provides a method in an particle detection system, said method including: capturing a series of image frames with a light sensor, said series of image including a plurality of "on frames" in which a primary light source associated with the light sensor is on and a plurality of "off frames" in which a primary light source associated with the light sensor is off, wherein said off frames can be interspersed between the on frames; and processing either the on frames and/or off frames using a factor, f, for correcting for the variance in mean illumination levels between the on frames and off frames.

In preferred forms f is calculated in at least one of the following manners:

$$f = \frac{\left(\frac{\mu_{on1}}{\mu_{off1}} + \frac{\mu_{on2}}{\mu_{off2}}\right)}{2}, f = \frac{\mu_{on1} + \mu_{on2}}{\mu_{off1} + \mu_{off2}}, \text{ or } f = \left(\frac{\mu_{on1} \cdot \mu_{on2}}{\mu_{off1} \cdot \mu_{off2}}\right)^{1/2}$$

where: μ is the average value of pixel intensity in two background regions, 1 and 2 that are located on opposite sides of a region of interest and as denoted by the subscripts, and the subscripts "on", and "off" denote whether the image is an emitter on frame or off frame.

In another aspect the present invention provides a method of processing a light scattering signal from particle detection system: receiving a light scattering signal; identifying a temporary peak in received scattered light intensity in the signal; and smoothing the temporary increase in received scattered light intensity of the signal.

In the method the temporary peak in received scattered light intensity can be a size of a predetermined number of pixels when compared to a spatially based average intensity.

Preferably the peak has a duration of 1 pixel. The temporary peak in received scattered light intensity is has a size of a predetermined number of frames when compared to a time based average intensity. For example the peak can have a duration of 1 frame.

The step of smoothing the peak can include one or more of the following: clipping the peak, ignoring the peak; or replacing the peak with a predetermined value.

The peak is preferably replaced by one of the following values: e.g. a local average, a temporal average, a neighbouring value, a preceding value, a following value, etc.

The temporary peak can be determined with reference to a predetermined threshold signal level. The threshold signal level can be determined based on a statistical measure of the received signal, for example, one or more standard deviations above the local or temporal average signal value.

In another aspect the present invention provides a method, in an particle detection system including: determining a statistically derived correction value for at least partially correcting for the affect of dust on scattering readings; and correcting the scattering readings using said correction value.

In a preferred form the method includes, for one or more pixels of an image capture device: determining backgrounds noise levels in the received scattering values; determining the standard deviation and mean scattering levels with reference to known representative statistical values for dust and smoke; calculating the scattering standard deviation; and determining the scattering contribution of smoke and/or dust.

In an alternative embodiment the method includes: determining backgrounds noise levels in the received scattering values; determining a higher statistical moment of the distribution of scattering readings with reference to known representative statistical values for dust and smoke; calculating the scattering standard deviation; and determining the scattering contribution of smoke and/or dust.

The method can include correcting measured scattering readings to a value representative only of smoke particles.

In another aspect the present invention provides a method of determining an alarm condition in an particle detector including: defining a plurality of segments along a beam of a primary light source; defining a plurality of virtual particle detectors at positions along the beam; associating each virtual particle detector with at least one segments; determining an alarm level of a virtual particle detector on the basis of one or more of the segment(s) associated with it.

Preferably the alarm level of virtual smoke detector is the highest alarm level amongst the one or more of the segment (s) associated with it. Alternatively the alarm level of the virtual particle detector is determined on the basis of the highest smoke reading of any associated segment.

The segments may overlap. Moreover segments may have weighted contribution when used to calculate an alarm level of a corresponding virtual detector.

In one aspect there is provided a particle detection system having a primary light source operating at a wavelength at which little or no ambient light is encountered by the system. For example, the primary light source can operate at a wavelength corresponding to either a solar or atmospheric absorption line, e.g. below 300 nm at which wavelengths the atmosphere absorbs most received sunlight, or at 656 nm which corresponds to an absorption line.

In one form the light source operates at a wavelength outside the spectrum of a lighting used to illuminate in the volume being monitored, or an adjacent volume.

The light sensor can include a filter having a pass-band including the chosen wavelength. Preferably the filter's pass-band is narrower than the absorption line in which the system operates.

In another aspect the present invention provides a method of correcting a scattering reading for the presence of large particles in an particle detection system, the method including: determining the total scattering over at least part of a beam from a primary light source; determining the total loss over a the part of the beam; calculating a correction factor for scattering readings for the part of the beam on the basis of the ratio of total scattering to total loss over the part of the beam.

The correction factor can be calculated as (fractional light loss:scattering)$^k$, where k is takes a value between 0 and 1.

Measuring the fractional light loss can include, measuring the received light intensity over the whole cross section of the beam.

The method can include setting a 100% transmission level from which subsequent transmission levels are computed. The 100% transmission level can be set periodically.

The method can include performing said method at a plurality of wavelengths.

In another aspect the present invention provides a fractional light loss measurement device configured to measure fractional light loss of a beam of light, said beam defining a cross section at the measurement device, fractional light loss measurement device including a light sensitive element configured to measure light from an area greater than the cross section of the beam. The light sensitive element can have a light receiving surface larger than the cross section of the beam. The device can include an optical arrangement able to receive light from an area greater than the cross section of the beam and direct it onto the light sensitive element. The fractional light loss measurement device can include means to prevent laser speckle, e.g. a defocusing lens.

In a further aspect there is provided an AVSD system including a primary light source and a light sensor adapted to receive light scattered from the beam of the primary light source within the volume and a fractional light loss measurement device according to the previous aspect of the invention.

The system can include a reflector to reflect the beam across the volume. In this case the fractional light loss measurement device and a primary light source of the AVSD system are substantially co-located.

The system can include one or more of the following, to reduce multi-path effects in the projection of the beam onto the fractional light loss measurement device: jittering the beam position, de-cohering the beam; and using of a non-coherent primary light source.

In another aspect the present invention provides a method of processing an output of a light sensor in an AVSD system, the method including: capturing a plurality of image frames from the light sensor, wherein a first set of the frames are taken when a primary light source is illuminated (one frames) and a second set of the frames are taken when the primary light source is off (off frames) and wherein the on frames and off frames have the same centre of time. Centre of time can be calculated as follows, (time×exposure length) number of frames.

Preferably the total exposure time of the on frames and off frames is the same.

In a preferred form the method includes applying a scaling to some of the frames. In one form the on frames and off frames include different numbers of frames. Preferably a scaling function is applied to some or all of the frames to ensure that the on frame and off frames have the same total exposure.

In another aspect the present invention provides a device for steering an optical component in an particle detection system, the device including, a coarse steering stage and a fine steering stage mounted on the coarse steering stage and to which an optical component can be mounted.

Preferably the coarse steering stage is a mechanical steering stage. The fine steering stage is preferably a non mechanical steering stage. The non-mechanical steering stage can include one or more of the following actuators: electro-mechanical actuators; piezoelectric actuators; another high speed non-mechanical actuator.

In a further aspect there is provided a method of steering an optical component of a particle detection system including, steering the optical component from an initial position, using a mechanically driven coarse steering stage, to a coarsely aligned position within a first predefined tolerance of a desired position; and steering the optical component from the coarsely aligned position, using a non-mechanically driven fine steering stage to a final position within a second predefined tolerance of the desired position.

The method can include at least periodically re-aligning the optical component with the desired position using the non-mechanically driven fine steering stage.

In another aspect the present invention provides an optical component for a particle detection system including: an optical assembly including an exposed optical surface through which light passes, a housing having at least one wall defining a volume within the housing, and an aperture through which light may enter or leave the housing, the housing being configured to receive the optical assembly such that light may be received through the aperture and wherein the optical assembly is mounted within the housing such that a gap is provided between the optical surface of the optical assembly and the aperture to provide a settling zone for particles entrained in the air.

The settling zone can be provided with particle removal means for removing particles from the air in the settling zone. The particle removal means can include an element selected from the following: a passive electrostatic material, an active electrostatic filter to remove particles.

In another embodiment an optical component for a particle detection system including: an optical assembly including an exposed optical surface through which light passes, a housing having at least one wall defining a volume within the housing, a viewing aperture through which light may enter or leave the housing, and an air inlet adapted to allow air to enter the volume within the housing, the housing being configured to receive the optical assembly such that light may be received through the viewing aperture and air can flow from the air inlet and out of the viewing aperture.

The optical component can include an aspirator to draw air into the air inlet or draw air out of the viewing aperture. The air inlet can be provided with a filter to clean air entering the housing.

When the aspirator includes an axial fan having a plurality of blades, the fan can be positioned to enable light to enter and exit the aperture between blades of the fan. The operation of the optical component can be synchronised with the fan's rotation.

In another aspect there is provided an optical component for a particle detection system including: an optical assembly including an exposed optical surface through which light passes, a movable member adapted to be moved across the optical surface at least periodically.

The fan can include a brushless DC motor.

The movable member preferably performs a cyclic or reciprocating motion across the optical surface. The movable member can be one of the following: a wiper, brush or rod. Preferably the movable member can be spaced from the optical surface. The movable member can be configured to pass over a scratch resistant window.

In another embodiment the present invention provides an optical component of an AVSD system including a functional element and a cooling device. In a preferred embodiment the optical component is a light sensor and the functional element is a light sensitive element e.g. CMOS image capture chip or CCD. Preferably the cooling device is a Peltier cooler. The cooling device can be in heat communication with a heat sink thermally coupled to the cooling device to transfer heat to atmosphere.

In one embodiment the present invention provides a particle detection system configured to detect particle in an air volume, said system including a primary light source configured to create a curtain of light across at least part of a volume being monitored.

The system can further include: an image sensor is positioned to capture images of a least part of the curtain of light; means to analyse the captured images to detect the presence of particles within the volume on the basis of scattered radiation captured in the images.

Preferably the curtain of light is created using optical means to create a divergent beam. Alternatively a curtain of light can be created by scanning a linear beam across the volume being monitored.

Preferably the curtain of light is planar. In this case, the image capture means can be placed in the plane.

In a further aspect the present invention provides a mechanism for generating a scanning beam in an particle detection system, said mechanism including a light source adapted to generate a linear beam of light and a mirror with planar reflective faces rotating about an axis parallel to the faces, said mirror and light source being aligned such that the light from the light source is reflected from a surface of the mirror with changing angles of incidence as the mirror rotates. The mirror is preferably polygonal, and more preferably octagonal.

In a further aspect the present invention provides a method of operating an particle detection system at an ambient light level at which would cause saturation of an image sensor of the system at a predetermined aperture size, at a first exposure duration, the method including: determining a reduced exposure duration which will not cause saturation of the image sensor; determining an increased frequency of image capture on the basis of the reduced exposure duration.

Preferably the exposure time is reduced by a factor of N to avoid saturation, and the image capture frequency is increased by substantially the same factor N.

In preferred embodiments the increased frequency of image capture is above 500 images per second. Most preferably it is between 600 to 2000 images per second.

In a further aspect the present invention provides a method of correcting light scattering measurements made by an particle detection system, the method including: determining fractional light loss along a beam of a particle detection system: correcting scattering measurements made in respect of a primary light source of the particle detection system on the basis of the determined fractional light loss.

The step of determining fractional light loss can include, estimating fractional light loss along the beam. This estimation can be made on the basis of scattering measurements from the beam. Fractional light loss estimation can be conducted on a piecewise manner along the beam length.

The step of determining fractional light loss can include, measuring fractional light loss along the beam. This can include providing a light reception means adapted to receive the beam of light at a terminal end thereof. The method can be repeated iteratively. The step of correcting scattering measurements can include dividing a scattering measurement by (1-fractional light loss).

BRIEF DESCRIPTION OF THE DRAWINGS

Illustrative embodiments of the various aspects of the present invention will now be described by way of non-limiting the example with reference to the accompanying drawings, in which.

DETAILED DESCRIPTION OF THE
EMBODIMENTS

As part of the operation of an AVSD system according to an embodiment of the present invention, it may be necessary to determine if there are any obstructions in the field of view of the optical receiver that may reduce the sensor's ability to detect smoke over the expected area of operation. Specifically, it is necessary to monitor the sector defined by the imaginary line connecting the receiver to the light source and the line formed by the projection of the collimated light beam as shown in FIG. 1.

Figure 1:
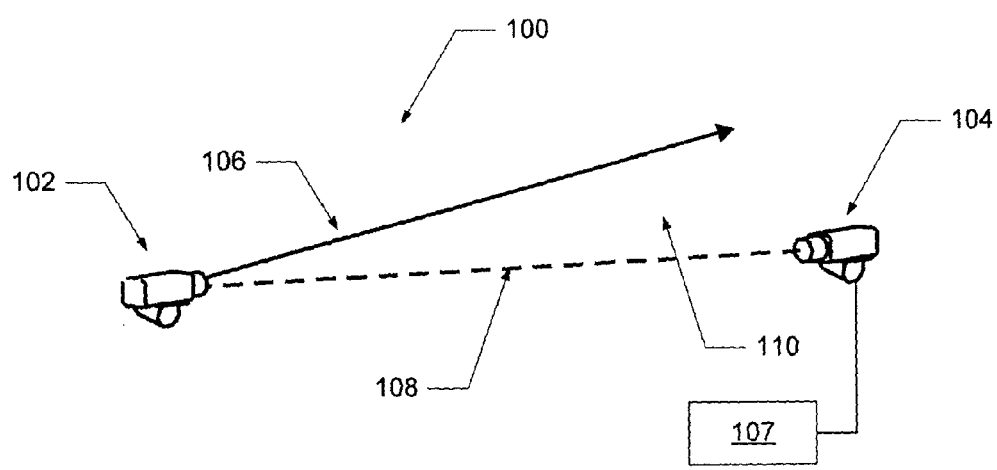
FIG. 1 shows a typical AVSD particle detection system according to an embodiment of the present invention.

FIG. 1, illustrates a typical AVSD particle detection system 100 including a light source 102 and a receiver 104 in the form of a camera. The light source is arranged to emit a beam of light 106 that traverses a space being monitored. The camera 104 is aligned to view the light source 102 and its beam 106 and to detect the level of light scattered from the beam 106 by particles present in the space being monitored. The critical volume 110 in which obstructions must be monitored is between the beam 106 and the imaginary line joining 108 the camera and the light source 102. If obstructions occur in this region the beam 106 will be obscured from the view of the camera 104 and thus the camera will not be able to detect scattered light from the entire beam and the detection sensitivity of the system will be compromised. The image sensor 104 (and possibly the emitter 102) is connected to a processor 107 which is adapted to analyse the images captured, either with or without source illumination data, to determine detect the presence of particles within the volume on the basis of radiation captured in the images.

Figure 2:
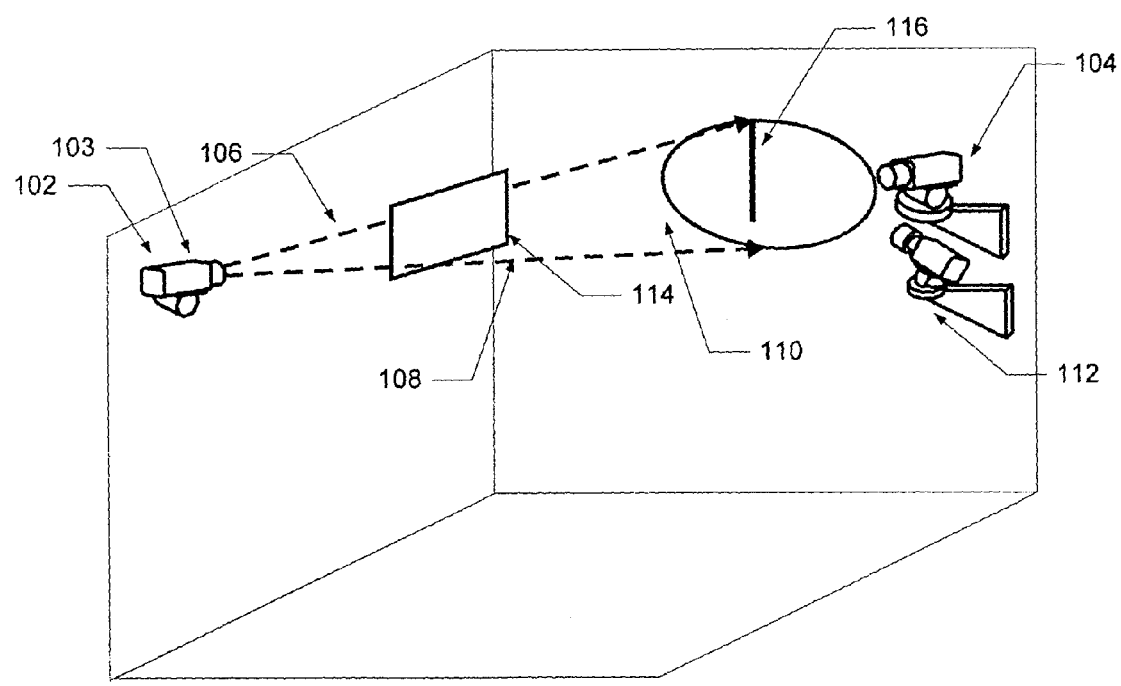
FIG. 2 illustrates a second embodiment of an AVSD system, this time incorporating multiple image capture means, which can be used to detect obstructions in the region of interest of the system.

One method for detecting obstructions in the volume 110 is to project an un-collimated or spread beam over the sector 110 to be monitored. Alternatively, a collimated beam may be rapidly scanned across the section 110 to achieve a similar outcome. If obstructions are present in the volume 110 shadows will be cast by the un-collimated beam. FIG. 2, shows an exemplary arrangement in which the AVSD system of FIG. 1 has been augmented with a second, rearward facing camera 112 and a source 103 of un-collimated light that projects light over the region 110. The camera rearward facing 112 is arranged to view the surface behind the region 110 that is illuminated by the source 103 of un-collimated light. Using such an arrangement an object 114 intruding into the volume 110 will cast a shadow 116 that can be observed by the rearward looking camera 112. Images taken by camera 112 may be processed to recognise a variation from a pre-recorded "reference" image known to be free of obstructions. If a variation between an image frame from the second camera 112 and the reference image is determined by the processing to be significant then a fault alarm can be raised. Alternatively the image processing may determine the presence of a shadow caused by an obstruction by comparing intensities of adjacent image regions and determining that there is sufficient variation between neighbouring regions to detect a shadow.

It is desirable that the light source 103 be non-visible as this offers the advantage that it will be unobtrusive to people working in the area and therefore not cause disturbance. In one embodiment the light source 103 could be a Xenon Flash lamp.

The system can be arranged to trigger a fault condition if a shadow of a predetermined size persists for longer than a predetermined time. The length of the predetermined time should be long enough to avoid going into a fault condition over a transient obstruction, such as a bird quickly flying through the region 110.

In some embodiments of an AVSD system according to the present invention it would be advantageous to have its major components located in close proximity to each other, e.g. at the same end of the protected space, as opposed to on opposite ends of the room as in the systems of FIGS. 1 and 2. Such an arrangement removes the need to provide power and signalling to opposite sides of the protected space, and consequently may result in a lower cost of installation of the system.

In one form, this aim may be achieved using a special purpose reflector placed at the distal end of the protected space, away from the light source and receiver. The light beam is directed toward the reflector, which is designed to return a reflected beam to a required target position, which may be adjacent the receiver.

The reflector may have greater than 90 degree "corners" to cause beam to be reflected at a fixed angle to incident beam. The reflector may alternatively be a convex mirror where the beam is steered to be reflected to a known target position. The mirror may be actually implemented as a set of flat mirrors or could be concave too, allowing for a convergent reflected beam.

Figure 3:
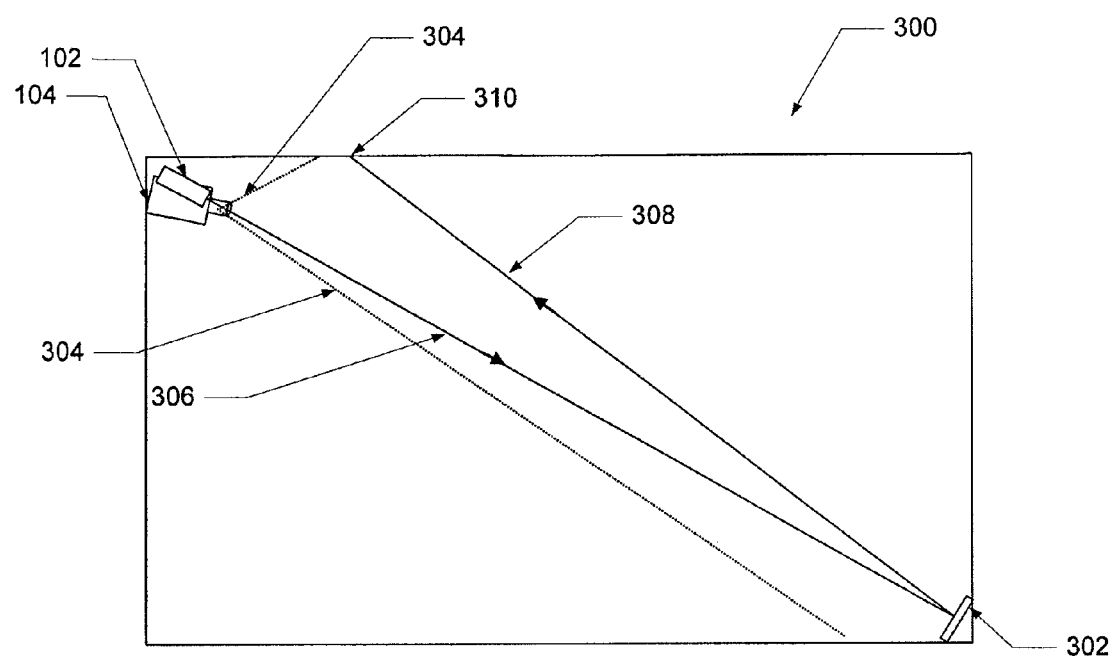
FIG. 3 illustrates an example of an AVSD system incorporating a reflector at its far end, which can be used in embodiments of the present invention.

FIG. 3 illustrates in an embodiment of this aspect of the present invention 300 where the receiver 104 and light source 102 are mounted relatively nearby each other. In a particularly preferred form they may be substantially co-located, e.g. in the same housing. In this embodiment, the light beam 306 is directed at a planar reflective surface 302, and the camera 104 is aligned to give a field-of-view (illustrated by the lines 304) which includes the reflector 302, part of the incident beam 306, the entire reflected beam 308, and the target 310. As discussed in our earlier patent applications that were referenced above, the target spot 310 may be allowed to fall out of the direct view of the camera 104 if other methods for its supervision are provided.

The reflector 302 may be mounted on an adjustable mounting that enables its angle to be manually adjusted at installation e.g. by the use of adjustment screws or the like. Alternatively, a further improvement may be obtained to maintain long-term positional stability of the reflected beam, by using an electro-mechanically driven tilt mechanism such as the one illustrated in FIG. 33. While this requires power to be provided to the far end of the system, such a system may have very low average power consumption, permitting it to employ batteries with a long life. Many alternative actuator types will be known to those skilled in the art that can perform this function including geared electric motors, stepper motors, galvanic mirrors, solenoids, piezo-electric actuators, thermal actuators and the like.

The angular position of the mirror 302 may be advantageously set initially, and thereafter maintained, by remote control. This control may be performed automatically by software in the detection system using the visual image from the camera and other inputs. Similarly, the beam 306 emanating from the light source 102 may be automatically steered to remain directed on target at the reflector 302. Suitable mechanisms for beam steering are disclosed elsewhere herein.

Further, the ability to scan the reflected beam 308 by adjustment of the angle of the mirror 302 may be usefully employed to verify that the field of view of the camera has not become excessively obstructed. To do this, the reflected beam can be periodically scanned toward the camera. If during the scan the target spot disappears unexpectedly this is likely to be caused by an obstruction. Alternatively, if scattering (or an unexpected change in scattering) is detected during the scanning of the beam 306, this can be caused by the edge of an obstruction, which can be recognised by the detection software. At installation time, the effect of acceptably small obstructions (e.g. vertical building columns or fixtures) can be recorded and later compared to the new scan results.

In an alternative embodiment the reflector 302 may be curved, or made up of a number of adjoining flat mirrors each positioned at a slightly different angles. With this type of reflector the path of the reflected beam 308 can be altered from the light source by targeting a different portion of the reflector surface. In a still further configuration the reflector 302 may be a variant on the corner-reflector arrangement. Normally, such reflectors use reflective surfaces arranged orthogonally so that the light beam is reflected substantially directly back to the source, regardless of the point on the reflector where it lands. However, when the reflector surfaces are placed at 90 degrees plus an angle θ the reflected beam is always directed back at an angle of 2×θ from the incident beam.

Figure 4:
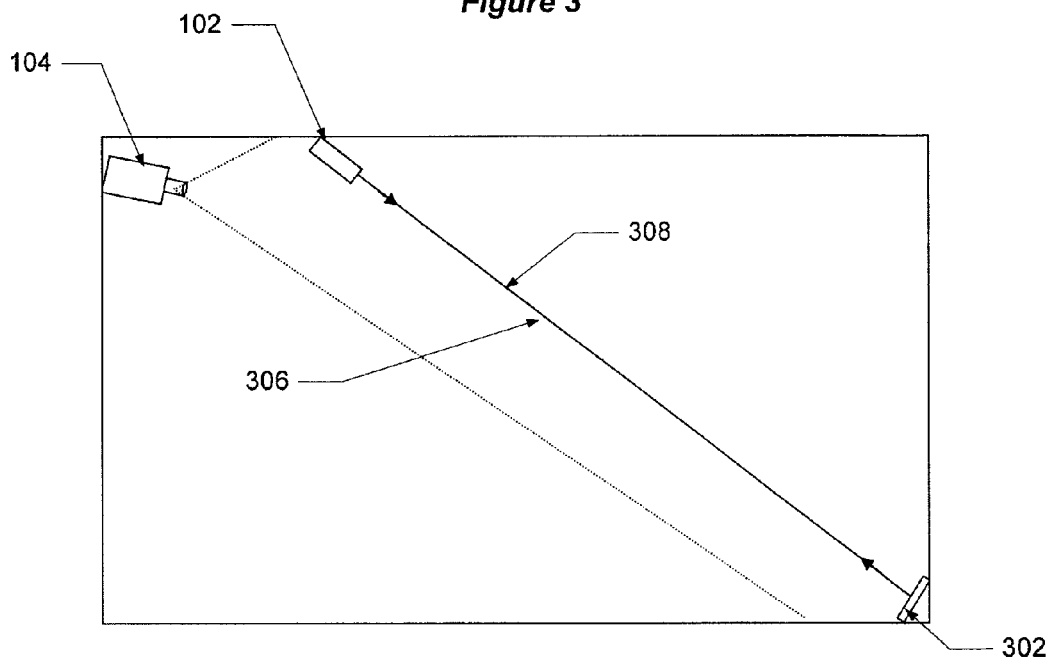
FIG. 4 illustrates an AVSD system according to a further embodiment of the present invention, which includes a 180 degree retro-reflector to return a transmitted beam back to a photo-detector at or adjacent the light source.

In a still further configuration, illustrated in FIG. 4 the light source 102 and the receiver 104 may be placed a short distance apart, and a conventional 180 degree retro-reflector 302 employed. In this way, the incident beam 306 and reflected beam 308 remain on the same path, in opposite directions. In order to supervise the arrival of the laser beam 308 back at the light source 102, a separate detection system in the form of, for example, a photo-diode located on the light source 102 may be employed. The signal from this device may also be used as a confirming transmission-loss smoke-detector in a manner described in more detail below.

In certain embodiments of the present invention telescopic imaging optics may be used to increase the effective range and sensitivity of the detection device. In one form the telescopic imaging optics may take the form of a commercially available zoom lens. The magnification of many commercially available lenses can be electrically controlled, allowing the system software to selectively zoom in on a part of the image to improve performance in that region. This may be particularly advantageous if a potentially ambiguous low level signal is identified in a specific area. In this case the telescopic optics can allow the system to zoom in on the region emitting the low signal and confirm the presence or absence of a particles or fire threat without risk of either unnecessary delay or false alarm. In this embodiment, the smoke can be detected in the receiver's output signal in any manner.

There are many situations in which it would be advantageous for the light beam to be visible to the camera even in the absence of airborne smoke or dust particles e.g. in order to facilitate system configuration at set-up, to enable installations where the light source and/or target are outside the field of view of the camera, and to monitor obstructions in the light beam.

The inventors have determined that such functionality can be provided by using a short wavelength light source that produces visible scattering from very small particles, such as oxygen and nitrogen gas molecules in clean air. For example a blue or UV laser or a collimated Xenon flash, optionally passed through a blue or UV filter could be used.

The short wavelength light source can be used alone i.e. used for smoke detection, or it may be used in conjunction with a primary light source that is used for smoke detection.

In preferred embodiments the short wavelength light source used is a blue, violet or ultra-violet laser diode. However with current technology, these have a limited total operational life, so it would preferably be operated for only brief periods e.g. at regular intervals, to meet the timing requirements for fault condition recognition. Therefore in the preferred embodiment a second light source that emits light in the visible or infrared spectrum, arranged to be co-linear or co-axial with the short-wavelength beam, is used for primary smoke detection purposes. If the life expectancy of short wavelength laser diodes improves in the future, as is expected, then the visible or infrared light source could be omitted.

It is known that short wavelength light sources generate relatively strong scattering signals in response to smaller particles when compared to longer wavelengths. This permits earlier detection of smokes containing a high proportion of small particles, for example those emanating from overheated cables of the "Low-Smoke Zero-Halogen" variety.

Further, by comparing the scattering signals from the short-wavelength source with those from the longer wavelength source an estimate of the relative proportions of small and larger particles can be made which is beneficial in permitting the identification of non-fire originated particles such as dust, so reducing the incidence of false fire alarms. In this embodiment, it may also be advantageous to extend the operational life of a short-wavelength source, by only activating it when particles have already been detected by scattering of the longer wavelength.

The particle detection system described in other embodiments of the present invention typically use non-visible wavelengths of light in order to avoid an undesirable visible spot, which may be a nuisance or distraction, especially in dimly lit environments. However, the fact that the light emitted by the primary light source is invisible may be a disadvantage e.g. at the time of installation if the installer wishes to verify that the light source(s) and camera(s) are positioned sufficiently accurately to allow the laser beam to be targeted correctly.

Figure 5:
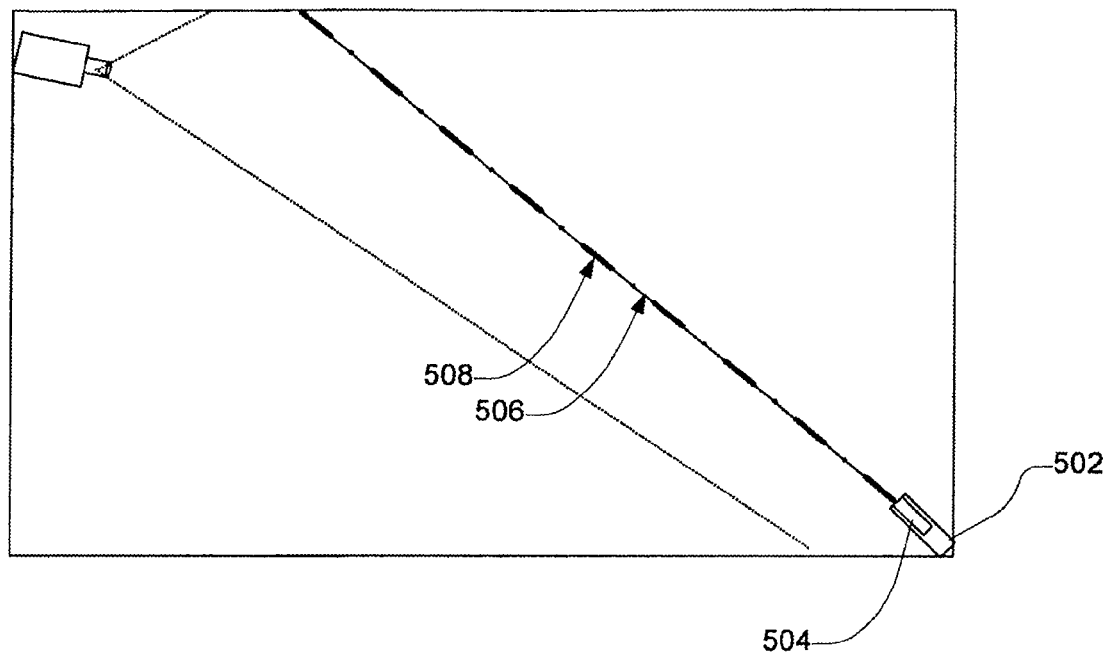
FIG. 5 illustrates an AVSD system according to an embodiment of the present invention using two coaxial light beams.

To facilitate ease of alignment of the primary light source, a second laser may be positioned which emits a beam of visible light as illustrated in FIG. 5. FIG. 5 illustrates a system 500 including two coaxial lasers 502 and 504. The first laser 502 emits a beam of light (506 illustrated in solid line) eg. in the infrared portion of the EM spectrum and is used as the primary laser for particle detection. The second laser 504 emits a light beam 508 in the visible portion of the electromagnetic spectrum.

This second laser can be mounted such that it is pre-aligned with the primary laser on an adjacent co-linear or co-axial path. The visible spot from this beam may be used to facilitate verification of the suitable positioning and alignment of the source.

After commissioning the second laser can be turned off during normal operation. If the primary laser needs to be re-aligned after commissioning the visible light source can be turned back on. The same physical structure could be used to mount a short wavelength (blue or UV) laser to implement an embodiment of the system described above.

In some embodiments of the present invention this system will be provided with a reflective target onto which the beam from the light source is directed. The beam reflected from this target can then be used for determining the correct alignment of the laser beam and possibly for other tasks such as fractional light loss measurement.

In other embodiments the system may call for a mechanism for scanning the beam from the target to another point in order to monitor the region adjacent to the beam path for obstructions.

In any case it is necessary to determine that the light source and the target are aligned in the desired fashion.

In order to determine that the light source is correctly aligned, so that it directs the laser beam onto the target position, the light source unit can be equipped with an optical detector, which is preferably directionally sensitive. The sensor is setup to track the alignment of the laser beam with respect to the light spot projected to the surface of the reflector. The detector can be used to measure fractional light loss and to track the location of the laser spot.

Figure 6:
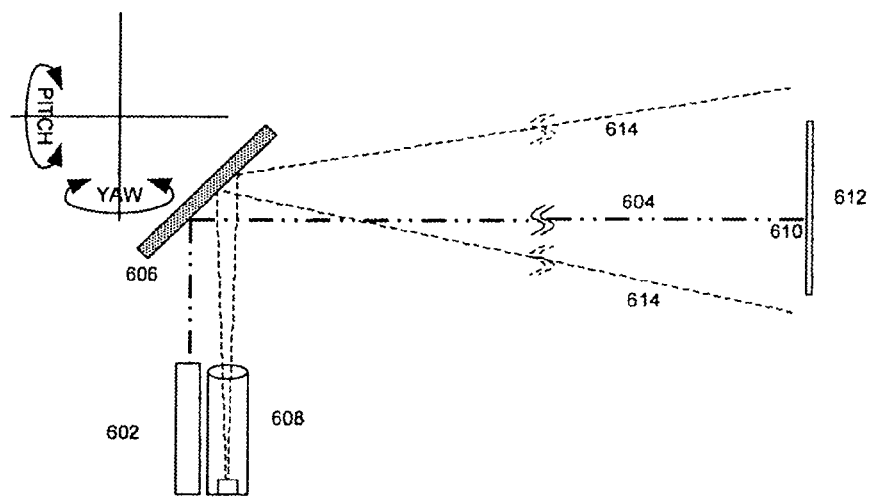
FIG. 6 illustrates an exemplary embodiment of a light source mounting arrangement that may be used in certain embodiments of the present invention.

FIG. 6 illustrates an exemplary embodiment of a light source mounting arrangement 600 that enables both beam steering and spot tracking. In this arrangement 600 the laser 602 emits a beam 604 that is steered by a electrically adjusting the angle of a movable mirror 606 in two rotational dimensions; for example, pitch and yaw.

Alternative arrangements to achieve the same movement capability include the use of a plurality of mirrors each of which may tilt in only one dimension; or direct movement the laser emitter itself; or a combination of a movable emitter and one or more mirrors or prisms or the like.

Preferably, the optical receiver 608 views the laser spot 610 on the retro-reflective target 612 through the same movable mirror 606. In one embodiment, the sensor 608 is mounted alongside the light source 602 and is aligned with it, such that the centre of its field of view 614 is centred substantially in line with the laser beam path 604.

In the preferred embodiment the optical receiver 608 consists of one or more photo-diodes mounted at the focal point of a lens mounted in a tube.

A problem that can arise with detecting the location of the retro-reflective target e.g. after beam scanning or during commissioning is that other objects in the region may also give substantial reflections which may be mistaken for the wanted target, so forming "false targets". An example is the intersection of glass windows and a high gloss window frame, which may form an unintentional but very effective "corner reflector", that reflects the beam back along or very close to, the incident path. Such false targets may be distinguished from the wanted target in a number of ways. For example, by scanning the width and height of the reflective target to verify that these parameters, e.g. the extent of the target, are commensurate with the those expected for the real target. Alternatively, distinguishing features may be added to the real target; for example areas of reflective and non-reflective materials around the periphery, so that scanning the beam can create recognisable responses in a manner similar to a bar-code reader. However, such methods may introduce undesirable complexities, ambiguities or delays in identifying the target.

Figure 7:
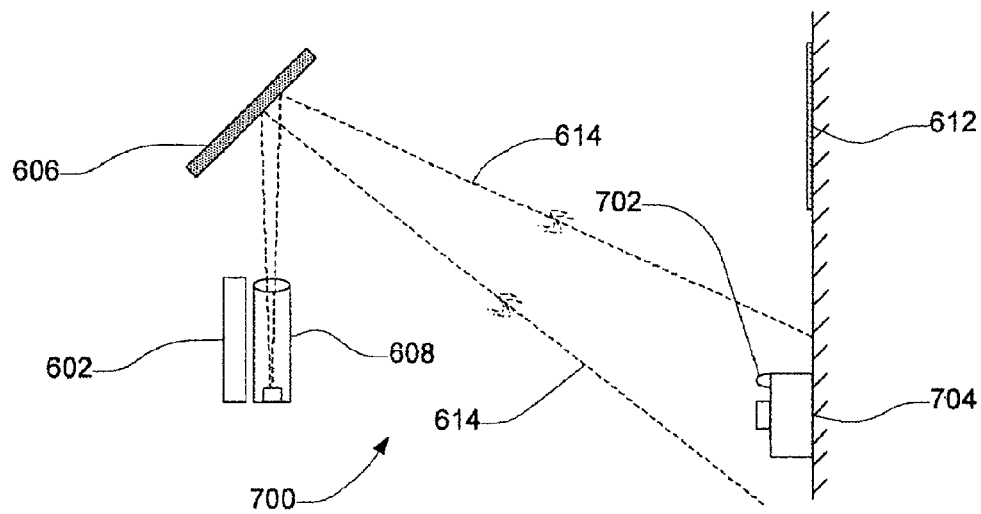
FIG. 7 illustrates a second embodiment of a light source mounting arrangement usable in an embodiment of the present invention.

FIG. 7 illustrates another embodiment of the present invention generally similar to that of FIG. 6 but which additionally includes a secondary light source that operates as a marker, in order to direct the laser beam correctly and quickly. In FIG. 7, features in common with FIG. 6 have been commonly numbered. The system 700 includes a secondary light source 702 that is preferably a LED emitting light at a wavelength to which the optical receiver 608 is sensitive. The light source 702 is mounted in a known positional relationship with respect to the target 612 and is preferably mounted on a sensor unit 704. In use the steerable mirror is adjusted to scan the laser from the target 612 to the sensors 704, during the search, the laser 602 may preferably be turned off and the secondary light source 702 is preferably modulated in a predetermined manner. This modulation is used in processing of the signal received by the sensor 608 to facilitate detection of the signal and to distinguish the wanted emitter 702 from any other unwanted light sources that may be present.

In the preferred embodiment, a search pattern is used which minimises the time required to locate the centre of view of the optical detector 608, and laser beam 602, on the retro-reflective target 612; as follows. Preferably, the mirror 606 is initially set to its centre position, and then caused to move in such a way that an increasingly large spiral shape is described by the laser beam movement. However, many alternative search patterns could readily be employed. The signal from the optical receiver 608 is processed to determine the mirror position at which the signal from the marker light source 702 mounted on the sensor 704 is maximised. The coordinates of the mirror 606 at that point are recorded as determining the location of the sensor unit 704.

Because the physical architecture of the installation is known i.e. the relative positions of the retro-reflective target 612 and the sensor unit 704 are known, when seen from the light source or mirror 606, the position of the expected target 612 can be determined. For example, the retro-reflective target 612 may be placed on the same horizontal line as the sensor's 704 inlet aperture at a displacement of 1 degree to the left.

Having determined the location of the sensor 704 as described, the mirror 606 is then aligned so that the laser is aimed at the expected position of the centre of the retro-reflective target 612 and the light source 602 is switched on and a similar search pattern begun. Theoretically this search should be begun with the laser centred on the retro-reflective target. In this instance, the laser beam is modulated in a predetermined manner and the optical signal received by the optical receiver 608 from the reflected laser light is processed to determine the position at which the signal from the retro-reflective target 612 is maximised. The coordinates of the mirror 606 at that point are recorded as determining the location of the retro-reflective target 612.

In an alternative arrangement the remotely located mirror can be made to be scannable in addition to (or alternative to) using a scanning light source. In this embodiment the light source is mounted close to the camera, and has an associated laser target mounted on it (or adjacent to it). The laser can be scanned to locate the "smart" remote plane mirror (e.g. using the outward spiral pattern described above). The mirror can then be arranged to automatically be tilted and/or panned to place the reflected laser spot on target, as judged by a photo sensor on the laser. The scanning arrangement for the mirror need only allow slow movement to enable final alignment, whereas the laser can be allowed to perform quicker movement so as to enable it to scan for intruding objects from camera end as described herein.

In some embodiments of the system disclosed in our previous patent application mentioned above, a transparency (or similar) can be used to simulate smoke for calibration or alignment of the system. In that embodiment a semi-transparent piece of light-scattering material may be advantageously used to determine the location of the laser beam path and to verify the correct operation of the particle detector. This is particularly valuable at commissioning and during maintenance.

However, a problem can arise during normal operation of the system in that objects may fully or partially enter the beam and cause scattering that may be confused with particles and so raise a false alarm. Even if the beam is positioned well above floor level, objects such as balloons or plastic may still enter the beam.

One method to avoid false alarms is to recognise the relatively sudden nature of an intrusion by a solid object compared to a smoke event. Instead of an alarm, a fault is raised in this case. While this method may be effective in some cases, for a scattered-light detector there remains a risk that an object will enter the beam at a rate that makes it substantially indistinguishable from smoke using this method alone.

The current embodiment of the present invention provides an alternative, or complementary, solution to address this problem and aid in distinguishing such solid objects from smoke. The principle of operation is that the primary smoke detection beam is scanned in one or more axes; if the scattering signal received varies in a manner that is characteristic of a solid object, e.g. substantially fixed edges are identified, then the object is recognised as solid and reported as causing a fault rather than an alarm condition. Preferably a plurality of scans are made, as a solid object will tend to scatter light in a substantially consistent and repeated fashion, whereas a plume of smoke will vary significantly in both position and strength over a similar time period. For example, a scanning period of 5 to 20 seconds may be advantageously used.

Figure 7A:
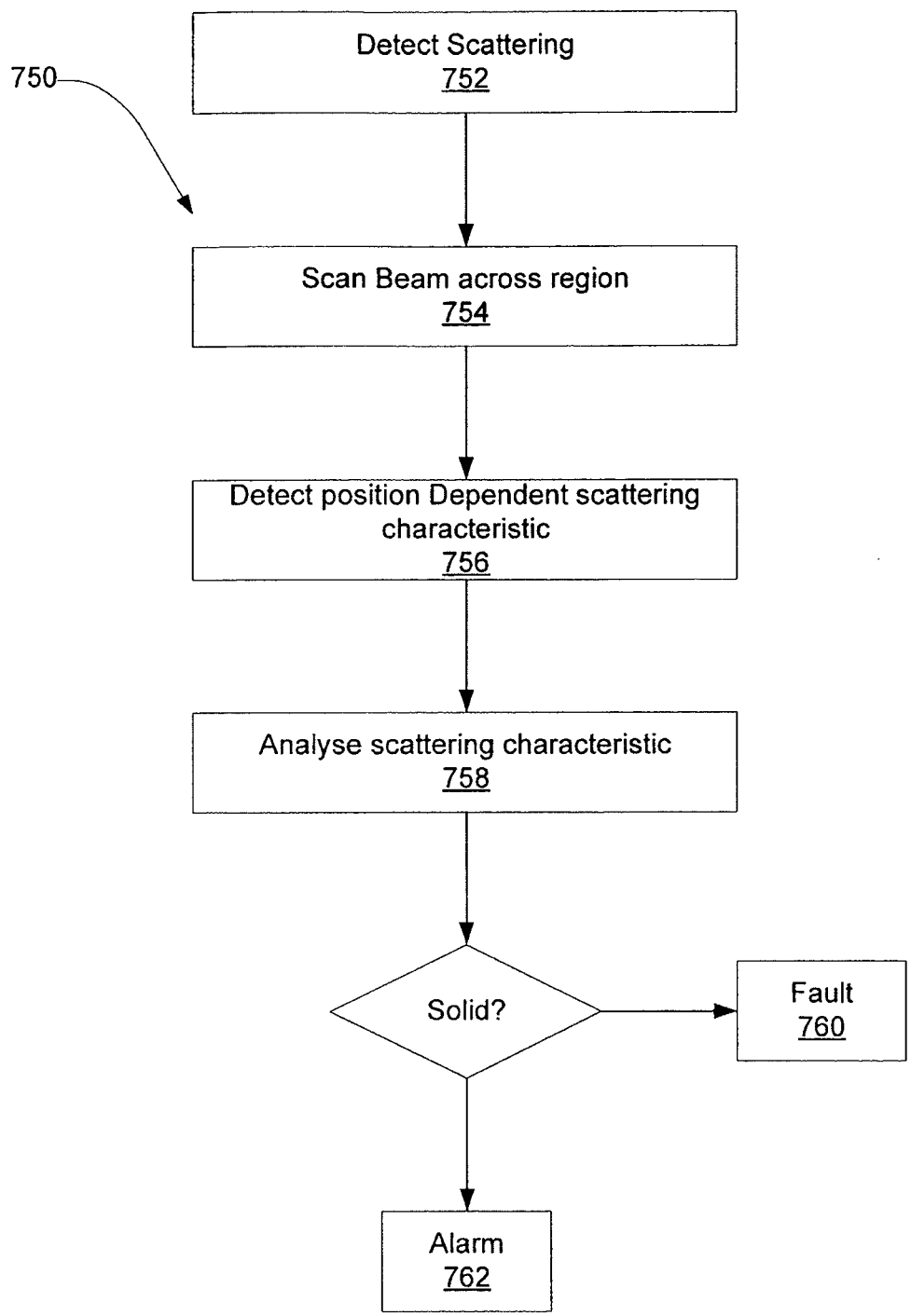
FIG. 7A is a flowchart illustrating an exemplary method for using position dependent scattering to determine a characteristic of an object intruding into a light beam in an AVSD system.
Figure 9:
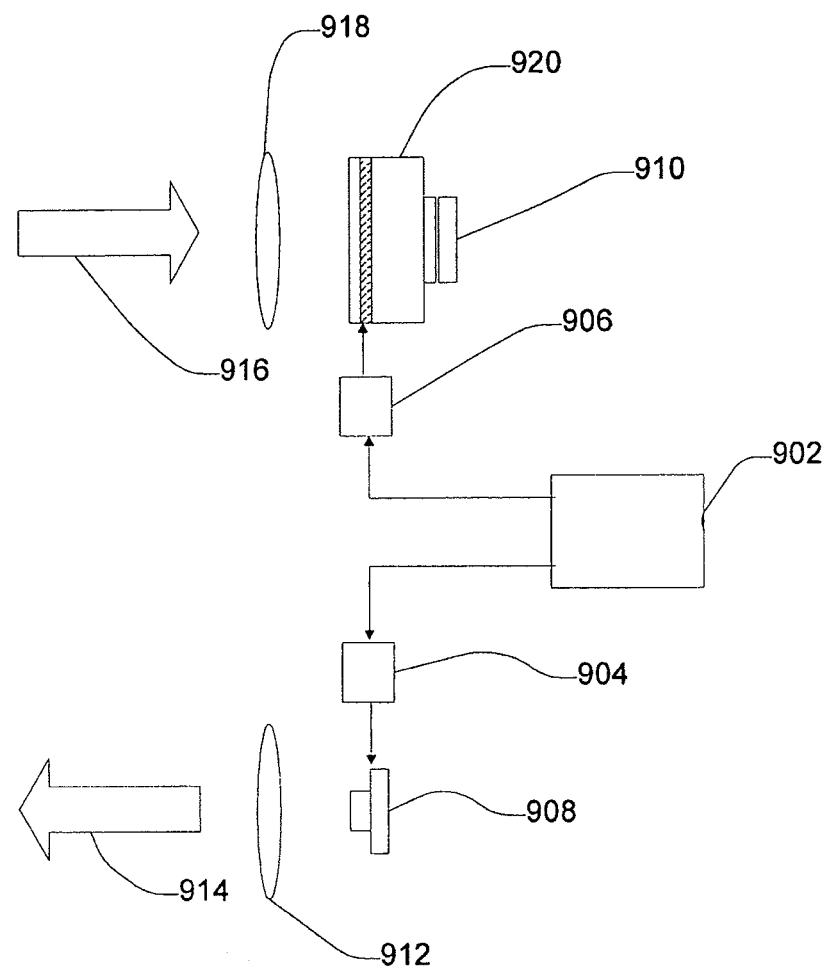
FIG. 9 illustrates a system for modulating light source intensity and receiver sensitivity that may be used in a system as disclosed in FIG. 8.

FIG. 7A is a flow chart illustrating such a method. In this figure the method 750 begins with the detection of scattered light by the AVSD system in step 752. Next the beam is scanned across the region of interest in a random or predetermined manner in step 754 in order to determine the manner in which the scattered light readings vary with beam position. From this measurement, a position dependent scattering characteristic of the scatterer is determined in step 756. For example, the position dependent scattering characteristic may be the absolute scattering level or the rate of change of scattering or some other measure. The scattering characteristic is then analysed in step 758 to determine whether spatial variation of the scattering characteristic of the object is solid-like or smoke-like. If the object is solid then a fault is raised at 760, and if the object is not solid an alarm signal may be raised at 762.

The fault or alarm condition raised by this process may be delayed in accordance with time delays and threshold levels built into the alarm protocol of the smoke alarm system. Moreover, the determination whether an intrusion into the beam is solid or smoke can be made repeatedly within the appropriate delay period such that if an object initially appears to be the solid intrusion into the beam but later resembles smoke an appropriate alarm could be raised, and visa versa.

Figure 8:
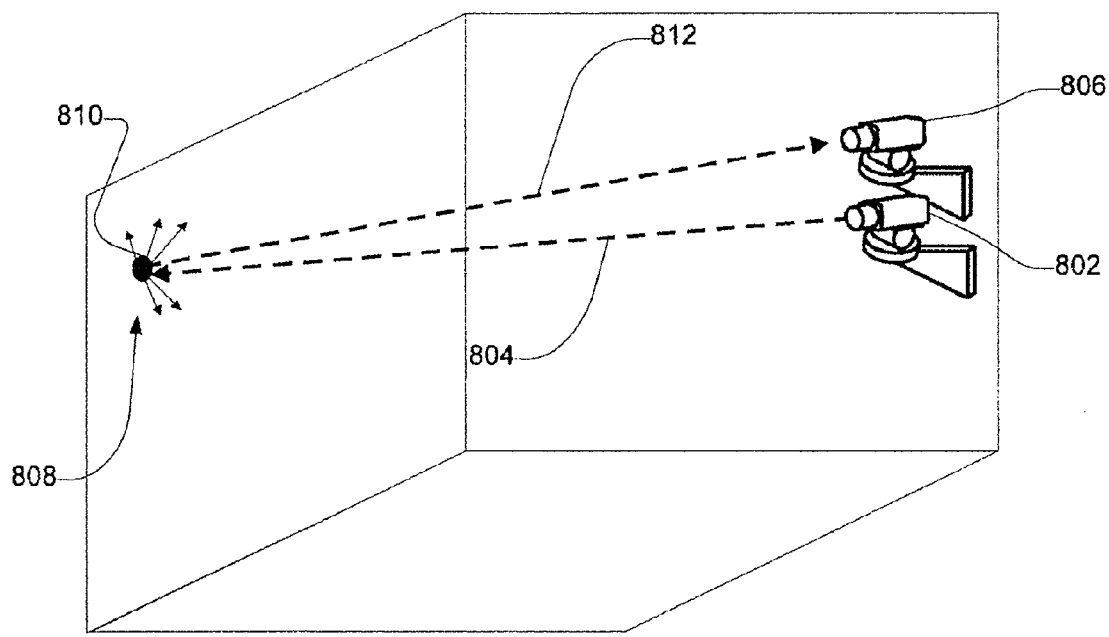
FIG. 8 illustrates a particle detection system according to an embodiment of the present invention in which the light beam emitted by the system impinges on a surface at the opposite end of the light beam being monitored.

In some embodiments of the present invention the system can be used with a backscatter geometry, in such a system a difficulty may be encountered, in that the observing camera can be overloaded due to scattering (reflection) from a surface on which the beam impinges, e.g. a surface on which the beam is projected to observe the location beam. If this occurs, the overloading can cause a 'blooming' effect on the receiving image sensor, thus making part of its field of view ineffective. This situation is shown in FIG. 8, which illustrates a particle detection system 800 according to an embodiment of the present invention. The system 800 includes a light source 802 that projects a beam 804, across a region being monitored. Particles entering the beam 804 cause light scattering, which is detected by the camera 806 to detect the presence of the particles. Additionally, when the beam 804 impinges on a wall 808 at the opposite side of the region being monitored a significant amount of scattering occurs at the spot 810 created. Because the spot 810 is within the field of view of the camera 806 and some of light scattered from the wall 812 is captured by the camera 806 this can result in part of the image sensor therein to be overloaded.

However, it is possible to address this problem by modulating the light source intensity and the receiving camera sensitivity in a manner that causes the affect of the scattered light to be significantly reduced at the time of the peak intensity of the arrival of the scattered light from the spot 810.

An arrangement for implementing such a method is shown in FIG. 10A and the associated driving wave forms used in one embodiment are shown in FIG. 10B.

Figure 10:
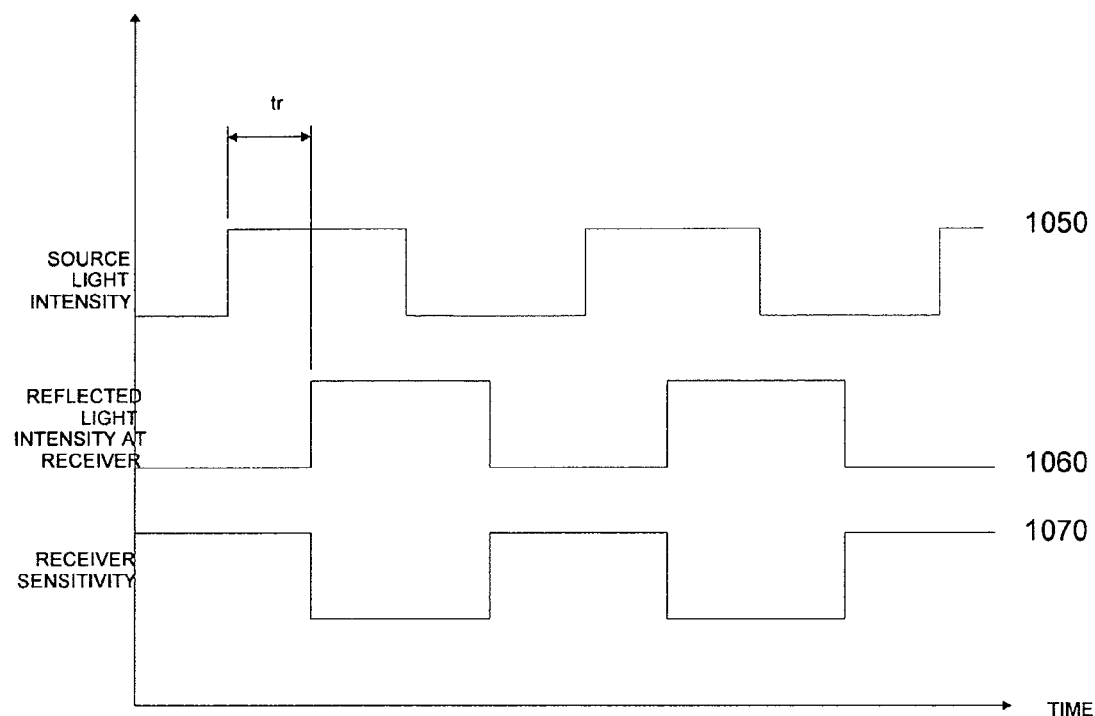
FIG. 10 illustrates a series of driving wave forms usable by the modulation system of FIG. 9.

The arrangement 900 includes a phase controlled pulse generator 902, which is connected to two driver circuits 904 and 906 connected to the light source 908 eg. a laser diode and the light sensor arrangement 910 (e.g. camera) respectively. Light is emitted from the laser diode 908 through the collimating lens 912. Part of the emitted beam 914 is reflected back as the return light 916. The returned light 916 first passes through focussing lens 918 before passing though micro-channel plate image intensifier 920, which has its operation controlled by the output pulse from the driver circuit 906. The amplified light beam 916 is then received at the CCD array of the light sensor 922. The source light intensity is modulated by the driver circuit 904 in such a way that after the beam has traveled to the target wall and been reflected back, it appears exactly out of phase with the modulated receiver sensitivity that is controlled by the driver circuit 906. FIG. 10 shows three graphs 1050, 1060, 1070 requesting the emitted light intensity from the laser 908, the reflected light sensitivity received at the sensor and the sensor's sensitivity, respectively.

The time taken for the light to travel from the source to the target wall and back to the sensor is indicated in FIG. 10B as $t_r$.

As can be seen in FIG. 10B the driving waveform 1050 for the laser diode 908 is modulated so that the round-trip time for the light pulse from the source, to the wall and back to the sensor coincides with reduced drive to the gated image intensifier 920 as shown in graph 1070.

To protect the camera and its optics from damage and contamination the camera will typically be mounted within a housing and the camera will view the area being monitored through a window in the housing. However contamination of the camera and its housing may still be a problem faced by installations of the present invention. There are many possible sources of contamination, e.g. dirt and dust accumulating on the detector optics. However one problem that may cause rapid obscuration of the camera is an insect crawling on the camera housing window, which if it occurs, will interfere with the ability of the system to detect smoke. Therefore, it is advantageous to supervise the window surface so that a fault is signalled if the window is covered or partially obscured.

Figure 11:
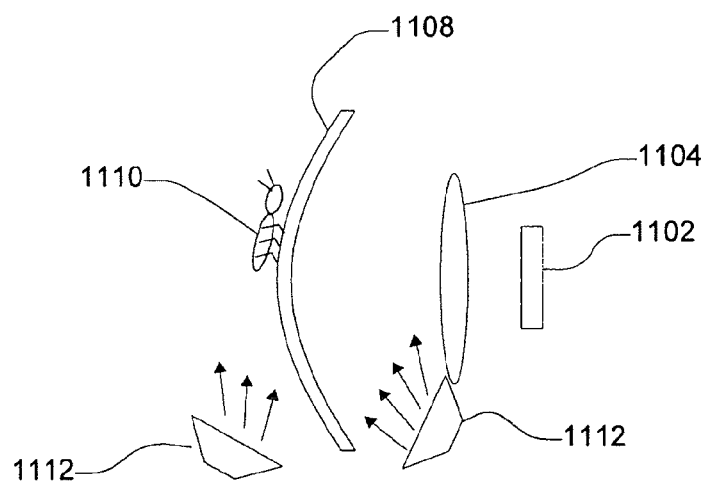
FIG. 11 illustrates part of the imaging arrangement used in an embodiment of the present invention that is adapted to detect obstructions caused by objects on the imaging optics.

FIG. 11 illustrates a part of an imaging arrangement used in an embodiment of the present invention. The imaging arrangement 1100 includes an image capture array 1102 e.g. a CCD, which views the area being monitored via a focussing lens (or lenses) 1104. These optics are protected by a transparent window 1108. If an insect 1110 crawls across the window 1108 the performance of the system will be degraded.

One method of checking for this type of obstruction is to illuminate the region of the window 1108 of the enclosure from time to time and check if the image captured differs substantially from a reference image known to be taken when the window is clear of obstructions, or predetermined threshold level. In order to provide the necessary illumination the imaging arrangement 1100 is provided with one or more light sources 1112 that are arranged to illuminate the surfaces of the window 1108. Any object close to or on the window 1108 will reflect a substantial portion of the illuminating light. An image captured under these conditions is compared with a reference image or threshold (taken without an obstruction) to determine if an obstruction on the window exists.

In an alternative embodiment the image taken with the light source 1112 "on" could be compared to a reference image taken with the light source 1112 off. In this case the image with the light source 1112 turned on will include a bright artifact as a result of illuminating the obstruction.

A similar technique can be used to detect insects or other obstructions on the inside of the window or on the surface of other optical components of the system, e.g. the image sensor lens.

In order to prevent exposure to potentially hazardous laser light levels emitted by some embodiments of the invention it may be necessary to monitor the laser path. In one embodiment of the present invention a fractional light loss measurement technique can be used to detect if there has been an intrusion into the laser beam path. If an intrusion is detected the system supervising the operation of the laser can be configured to reduce the laser power to a safe level until the intrusion is no longer present.

The present inventors have devised a number of ways for detecting intrusion onto the beam based on fractional light loss. One method is to place an optical detector in the beam path and measure the intensity of the arriving laser radiation. This intensity measure can be input to the supervising system, and if a reduction in the received light is detected then it may be assumed that an intrusion is present.

Figure 12:
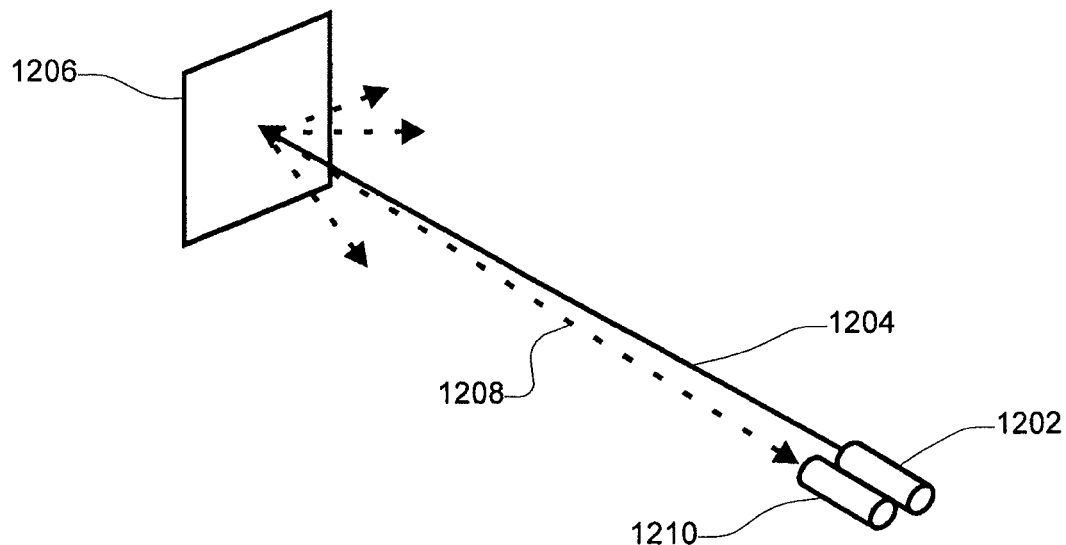
FIG. 12 illustrates a light source of an AVSD system according to a further embodiment of the present invention.

FIG. 12 illustrates the light source portion 1200 of a system according to an embodiment of this aspect of the present invention. This arrangement includes a primary light source 1202, which will typically be a laser, that emits a beam of radiation 1204. This beam is reflected by a reflector, 1206 which is placed at the opposite side of the region being monitored. In use the light beam 1204 traverses the region and is reflected off the reflector 1206. At the reflector 1206 the beam 1204 may be scattered and at least some of the reflected radiation 1208 will arrive at a suitably placed optical detector 1210. The reflector may be any of a variety of types, e.g. a corner cube type or a diffuse reflection surface or other retro-reflective material. The optical detector 1210 may be placed near the light source or at any other location where it is able to receive some reflected radiation.

If there is a change in the light level measured by the detector 1210 then it may indicate that something is obscuring the beam and as noted above the beam power can be reduced.

As will be noted in the aforementioned embodiments, it is sometimes necessary to steer the primary beam of the AVSD system, e.g. to align the beam on a target reflector during commissioning or at other times.

Figure 13:
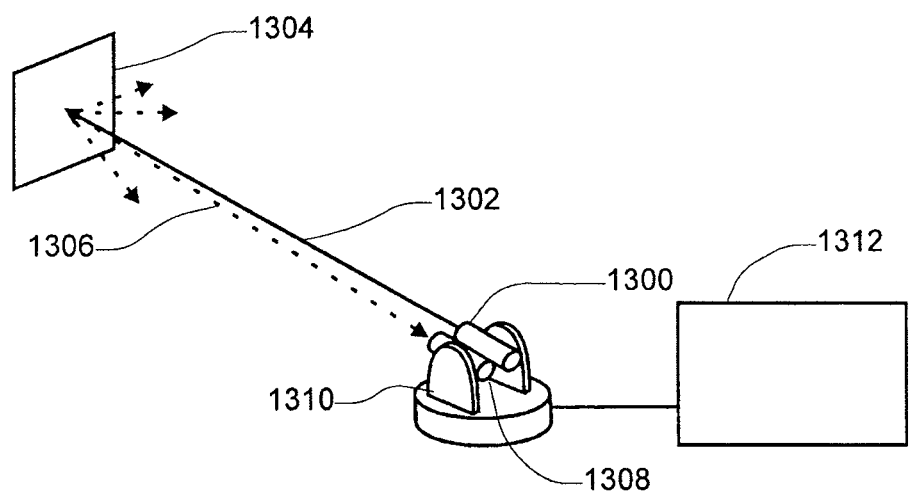
FIG. 13 illustrates an embodiment of the present invention in which the light source projects a beam towards a reflective target and in which the light source is mounted on a pan-tilt mechanism to allow steering of the beam.

In a preferred embodiment depicted in FIG. 13 a light source 1300 projects a beam 1302 in the direction of a reflective target 1304 in a manner described in previous embodiments. At least some of the reflected light 1306 is incident upon a receiver 1308 which is mounted adjacent to the light source 1300. The light source in this embodiment is mounted on a pan-tilt mechanism 1310 which has its position controlled by controller 1312 which adjusts the direction of the aforementioned beam in order to maximise the reflected light level received by receiver 1308.

The system requires a method for initially aligning and then maintaining alignment over time. The following is a method for performing accurate alignment using the apparatus described above.

The controller 1312 can cause the light source 1300 scan the beam 1302 over a region where the reflective target is likely to be, and stop when the received signal is above a pre-determined threshold. The pre-determined threshold can be a function of the distance. In order to find the centre of the target more exactly, the edges can be detected. To do this the laser 1300 is scanned over the target, and the positions at which the received signal is approximately half of the maxima are recorded. The laser is then set to the midpoint between these two positions. This process is then repeated in a direction orthogonal to the first, and can advantageously be repeated at least once more in the original direction. The repeated searches improve accuracy in cases where the target is not rectangular or its sides are not parallel to the search directions.

Other light sources can interfere with the above method. Some means of reducing the effects of interfering light sources are:
1) amplitude modulate the laser 1300, and use a receiver tuned to respond to this particular modulation (eg 1000 Hz on-off pulsations of the laser and synchronous detection with an integration period of 100 ms)
2) filter the received light with respect to wavelength (eg use a dye filter or an interference filter)
3) filter the received light with respect to polarisation (put a polariser in front of the receiver)

In order to assist installation and thereafter to confirm that the position of installed components has not changed, e.g.

due to tampering or movement in the mounting of components, a tilt sensor may be installed in at least one element of the system. In a preferred embodiment a tilt sensor is mounted in the camera housing and can be used to indicate if the sensor has moved out of alignment. Similarly a tilt sensor in the light source housing can indicate if the light source has moved out of alignment.

Figure 14:
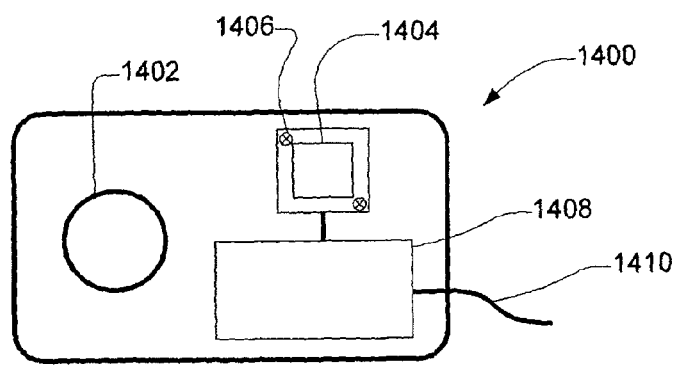
FIG. 14 illustrates a housing arrangement that can hold a light source or a receiver in an embodiment of the present invention.

Referring to FIG. 14, which shows a housing arrangement 1400 that can hold either a light source or a receiver. The housing 1400 is generally speaking an enclosure in which the components forming either a light source or a receiver are housed, and an aperture 1402 (which may be enclosed by a window). The aperture 1402 can be used either as an exit window for a light source housed in the housing 1402 or a viewing window for a receiver housed therein. A tilt sensor 1404 is mounted in a fixed relationship with the housing 1400 e.g. by fixing means 1406. The output signals from the tilt sensor 1404 are processed by signal conditioning circuit 1408 and compared with preset acceptable readings to provide an error signal. In the event that the error signals exceed a threshold a fault condition can be communicated to external monitoring equipment by a communication network e.g. via data cable 1410, or by other communications or signalling means such as a wireless communications link.

In order to establish that the system is able to detect smoke, it is necessary to ensure that there are no impediments to the camera's view of the laser beam path. Objects interposed between the beam and the camera will hide a portion of the beam path from the camera making it impossible to detect smoke along the hidden segment of the beam. Therefore it is necessary to check the camera's field of view over the area between the beam and the camera to ensure that it is free of objects. The inventors have conceived several methods which may be employed to detect objects in this area and some of these are described below.

The following supervision techniques can be applied to a range of AVSD system configurations, e.g. systems employing one or more light sources and/or one or more light sensors that perform smoke detection over different areas, using modifications that would be apparent to those skilled in the art.

Figure 15:
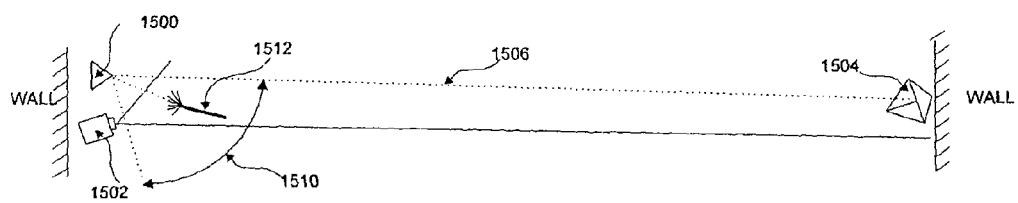
FIG. 15 illustrates an AVSD system according to a further embodiment of the present invention.

In the system configuration shown in FIG. 15, the light source 1500 and receiver 1502 are situated in close proximity to each other. The receiver 1502 is arranged to view a required area coincident with the path of the laser beam 1506. A reflector 1504, which may be a corner cube or other reflecting device is mounted at the opposing end of the area being monitored, and reflects the beam 1506 across the region being monitored in a direction such that the receiver 1502 can be used to detect forward scattering from the return path of the beam 1506 due to smoke or other particles.

The light source 1500 is mounted on a scanning mechanism so that the beam may be scanned over an arc 1510. Any object e.g. 1512, that is placed in the region bounded by the laser 1500, camera 1502 and reflector 1504 will be illuminated by the laser as it scans across it. Such illuminations may be detected by the camera and a fault raised.

In an embodiment in which the system is configured to include multiple light sources and receivers operating in pairs, the same method can be applied.

Figure 16:
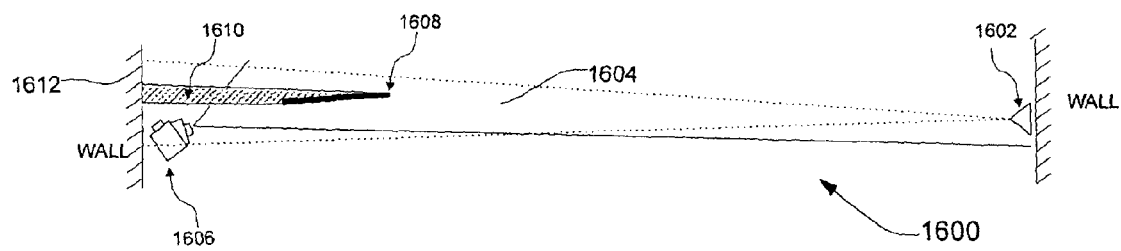
FIG. 16 illustrates an AVSD system according to an embodiment of the present invention, which uses shadow detection for monitoring faults.

Another supervision method, which can be used in certain embodiments of the present invention, involves projecting light across the area being monitored and checking to see if a shadow is cast by any intruding objects. In FIG. 16 a system 1600 is illustrated in which this supervision method is implemented. In the system 1600 a light source 1602 illuminates a region 1604 near a rearward facing camera 1606. In the event that an object eg. 1608 enters this region it casts a shadow 1610 on a background surface 1612 illuminated by the light source 1602. The output of the camera 1606 can be analysed to detect the shadow 1610 cast by the object 1608 and when a shadow is detected a fault can be raised.

Either the same or an additional light emitter-receiver pair can be used for primary smoke detection purposes.

It is known that where a light source; illuminated the edge of an opaque object that a glint is visible at the object's edge. Depending on the angle of viewing of the object and light source, the glint may be due to reflection or refraction. This phenomenon can be used in embodiments of the present invention to detect the presence of an intruding object. With reference to the FIG. 17, a light source 1700 projects a beam 1702 over the region being monitored 1704. The beam 1702 preferably illuminates the whole region being monitored. If the beam 1702 is narrow this can be achieved by scanning the beam 1702 e.g. with a steerable mirror etc. across the region. Alternatively this can be achieve using a wider beam which covers the entire region of interest 1704.

Light ray 1706, which may be due to a narrow steerable beam 1702 directed appropriately, or may be part of a wider beam, is coincident with an edge of intruding object 1708. In this case a reflected glint 1710 from the edge of the object will be visible to receiver 1712. Again as with the previous embodiment, the output of the receiver 1712 can be analysed to determine the presence of such a glint, and if one is identified an error signal can be raised. A drawback of this method is that the region 1714 cannot be supervised, since light will be received by the receiver 1712 directly from the light source 1700. This will tend to overload the receiver's detection elements.

In other embodiments a glint will also be visible due to refraction of light around an object. In the FIG. 18, which shows a system 1800 identical to that of FIG. 17, the light ray 1802, strikes the edge of the intruding object 1804 farthest from the camera 1712. In this case the glint is visible to the detector 1712 by refraction. The intruding object 1708 would also be detectable by virtue of the fact that the light source 1702, is itself hidden from receiver 1712, and any light that would normally be visible to the sensor is now not observable.

In the aforementioned embodiments using the detection of glints from an object for supervision, there may exist an area which is unable to be supervised. This area is difficult to supervise by glint due to the fact that the receiving system may be come overloaded or saturated due to light rays from the source that are directed at or near the sensor's lens. For example, if the sensor were a CCD camera, the pixels associated with the region around the light source may well saturate and bloom into neighbouring pixels resulting in the inability to detect glint by those pixels. In such circumstances, an alternative or additional mechanism may be used to supervise this region.

Figure 17:
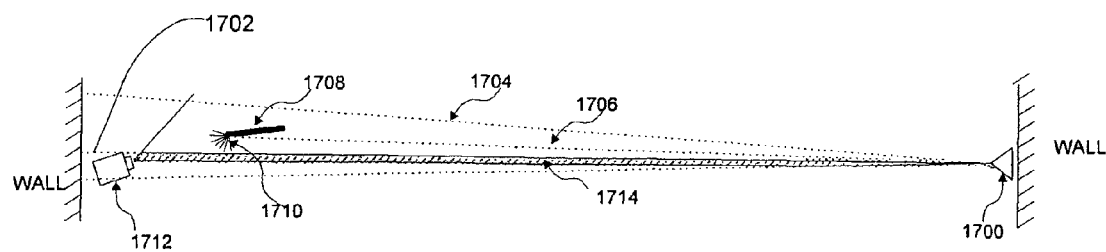
FIG. 17 illustrates the principle of using reflected glints of light from the edge of an object to detect the object impinging on the region of interest in a system according to an embodiment of the present invention.
Figure 18:
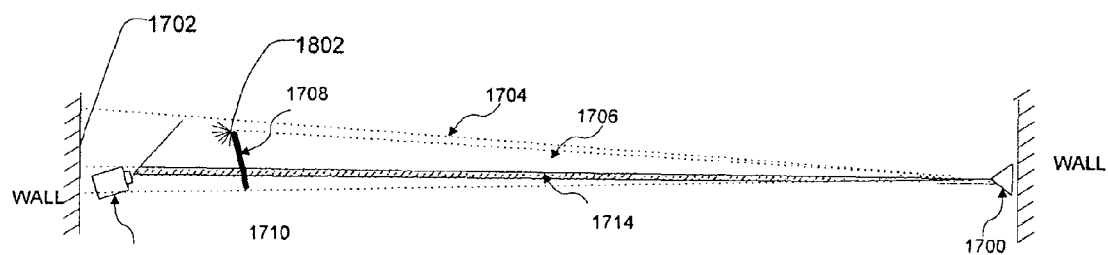
FIG. 18 illustrates the system of FIG. 17, when used for detecting an object in a different orientation to that shown in FIG. 17.
Figure 19:
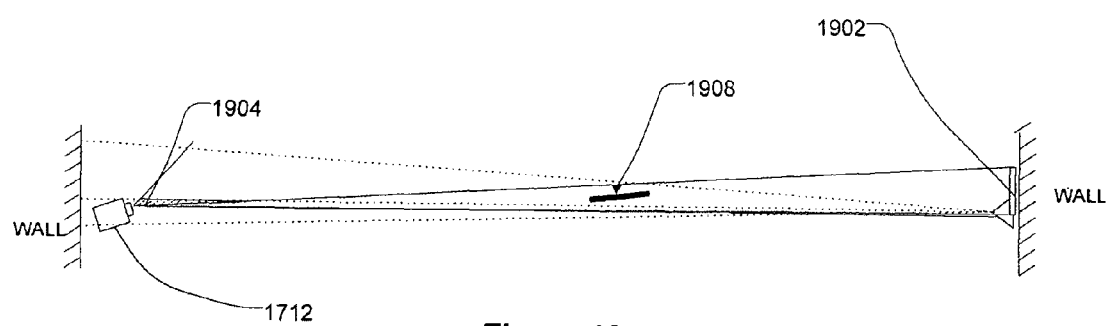
FIG. 19 illustrates an embodiment of the present invention, which uses a light bar to assist in the detection of foreign objects in the region being monitored.

One technique that can be used to supervise regions that are close to the light source in the sensor's field of view is to use a light source of sufficient physical size to cover otherwise unsupervised region, as illustrated in FIG. 19. In this embodiment the system of FIG. 17 is augmented with a light bar 1902 mounted next to the light source 1700. With the light bar 1902 in use, an intruding object 1904 will block the receiver's 1712 view of part or all of the light bar 1902. The output of the receiver 1702 can be analysed and the intruding object detected and a fault raised. The triangle formed by the sensor 1712, and the edges of light bar 1902, enclose the majority of the previously unsupervised region.

The remaining unsupervised region 1904, may be supervised by other methods, such as proximity detectors and other means known to those skilled in the art.

A further supervision mechanism can use the background behind the beam to possibly detect intrusions into the region of interest. In this regard, where a system is installed so that the sensor that views the region of interest against a background, as would be the case inside any normal building, the sensor can be configured to detect variations in the background image to determine if an object has moved into the region of interest. In essence this embodiment is similar to the method described above that uses a shadow to detect intrusions, but does not need an illumination beam to create changes in the background by way of a shadow.

Such a system has the potential disadvantage that it may be difficult to determine if the changes observed in the backgrounds image have occurred between the beam and the camera i.e. in the region of interest, or if the changes were merely in the background areas where they have no effect of the systems detection capability. In preferred forms this ambiguity can be resolved by adding at least one more receiver observing substantially the same region of interest but from a different viewpoint. Using this arrangement it is relatively straight forward to calculate the position of a detected object in the field of view using the principles of geometry. The system can thereby differentiate benignly placed objects from those which may interfere with the systems ability to detect smoke.

An additional problem with this method of background monitoring is that in dark environments it is possible that no background will be visible so it may not be possible to determine if an intruding object has been placed in the region of interest. One method of overcoming this problem is to employ active illumination so that at least some background features are always visible to the sensor when the region of interest is free from intruding objects. For example, the background may be illuminated by invisible electromagnetic radiation, e.g. IR, emitted from a dedicated illumination light source, if the camera is sensitive to this wavelength radiation.

In another embodiment of this scheme, the background regions may be populated with individual light sources such as, for example, LEDs or other small lamps whose light output is visible to the sensor. This is effectively a wide area light bar and can be implemented in line with the embodiments described above.

In yet another embodiment, a light may be projected on to part or all of the background that coincides with the sensor's view of the region of interest. This projected light may be in the form of a sheet of light which, when landing on a surface forms a stripe visible to the sensor, or it may be a beam or beams of light, either stationary or scanned over the background surfaces forming dots or multiple dots which are visible to the sensor; the presence of an intruding object in the field of view therefore causes a difference in the surface pattern as viewed by the sensor.

In a yet another embodiment, the background may have projected upon it a pattern or patterns that are identifiable by the system and thus minimize the likelihood of an intruding object being interpreted as a background feature.

Figure 23:
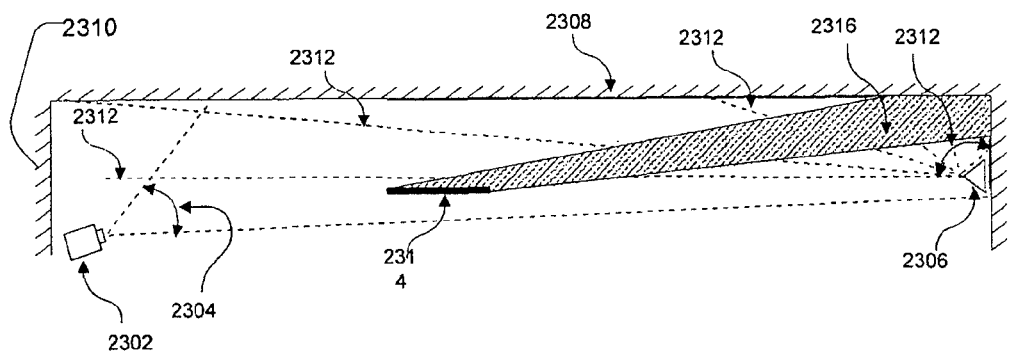
FIG. 23 illustrates an embodiment of the present invention that uses a vertically scanning beam for supervising the region of interest.

FIG. 23 illustrates an embodiment that uses a vertically scanning beam for supervision. The system 2300 includes a camera 2302 which has field of view 2304, in which a scanning light source 2306 resides. The beam from the light source can scan vertically over part of ceiling 2308 and part of wall 2310 that are visible to the camera 2302. The scanning light source 2306 is made to scan a region substantially overlapping field of view 2304 casting rays for example 2312. Other intermediate scan positions may be chosen depending on the requirements for size of object that must be detected.

In this system an intruding object 2314 that is introduced into the field of view masks the region 2316 from visibility to receiver 2302. Analysing the output of receiver 2302, in conjunction with known position of scanning light source 2306, reveals that in certain scan positions the camera 2302 will not view light on the wall or ceiling due to the masking effect of object 2314. In this case a fault condition can be raised.

In embodiments where the system has two pairs of cameras and receivers mounted in opposite directions, that is with a light source and receiver at each end, a light bar can also be used for supervision of the region of interest.

Figure 21:
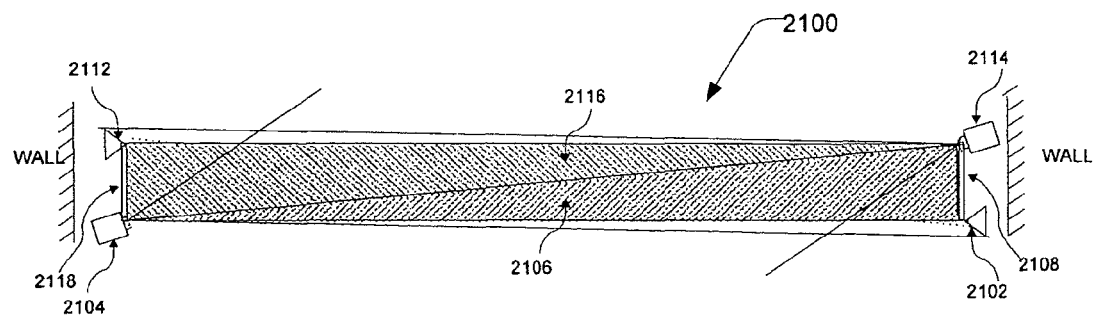
FIG. 21 illustrates another embodiment of the present invention using light bar supervision.

FIG. 21 illustrates a system 2100 of this type including a first light source 2102 and receiver 2104 configured to monitor a corresponding region of interest 2106. The system 2100 also includes a second light source 2112 and receiver 2114 configured to monitor a corresponding region of interest 2116. The system 2100 also includes two light bars 2108 and 2118. The light bars 2108 and 2118 are mounted between the first light source 2102 and the second receiver 2114, and between the second light source 2112 and the first receiver 2104. In use, the task of intrusion detection may be therefore split in two, with each laser-receiver pair monitoring a different area in the region of interest. The triangular area, 2106 is monitored by the first receiver 2104 and first light bar 2108, which is achieved by the sensor 2104 checking for any change across the intensity profile of the light bar, which as noted above can be is interpreted being caused by an intruding object obscuring the light from light bar 2108. Similarly, the triangular area 2116 is monitored by a second receiver 2114, and second light bar 2118.

Figure 22:
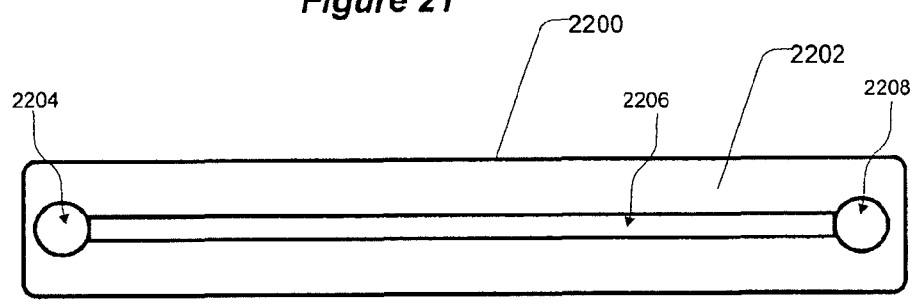
FIG. 22 illustrates an exemplary implementation of an apparatus that can be used in a system of the type shown in FIG. 21.

FIG. 22 illustrates an exemplary implementation of an apparatus 2200 that can be used in a preferred embodiment of this aspect of the present invention. The apparatus 2200 includes housing 2202 in which is mounted a combination of light source 2204, light bar 2206 and receiver 2208 that may be used at each end of system of the type illustrated in FIG. 21. In this example the light source 2204 will be used to project a beam of light toward a similar device mounted at the opposing end of the system for the detection of light scatter by a receiver mounted at that end. A light source mounted at that opposing end will emit a beam of light toward the sensor 2208 for detection of particles by scattering from the beam. The light bar 2206 extends from the light source 2204 to the sensor 2208 and is used by the light sensor mounted at to opposite end of the system to supervise the region of interest as described above.

In embodiments of the present invention, it is preferable that the primary light source used for particle detection is a laser beam, and that it is at a wavelength which is of low, or zero, visibility to the human eye e.g. for aesthetic reasons. In one embodiment, commonly available infra-red laser diodes with a wavelength in the region of 780 nm may be advantageously used. These laser diodes provide a good compromise of relatively low cost and satisfactory small particle detection performance, and their visibility is low because they emit in a narrow band at a wavelength to which the human eye is very insensitive. However, when using such laser diodes a problem may arise as follows.

In some embodiments, one or more additional light sources may be required to support functions such as assisting in the determination of the location of the light source, targeting the laser beam and supervising the sensor field of view. In such circumstances a LED device can be used since laser diodes are comparatively expensive and require more supporting circuitry. LED devices may also be centred at the same wavelength as the primary light source, but in currently available technology they emit light in a broader range and have higher visibility to the human eye, which may be an aesthetic nuisance especially when used in low ambient light circumstances, such as in a theatre.

It is known to automatically reduce the intensity of visible displays in low ambient lighting; for example LED alarm clocks are often equipped with a light sensor that causes the LED display to dim in a darkened room. However, while these methods are directed at maintaining visibility to the human eye, embodiments of the present invention must address the problem of causing the 'ON' intensity of the LED devices to be reduced to a point where the nuisance effect of their visibility is substantially removed, while at the same time they remain sufficiently intense that the signal detected by the associated sensor is adequate for correct functionality.

In the preferred embodiment, only two brightness levels of LED illumination intensity are used—i.e. the LED can be in one of three possible states 'OFF', 'BRIGHT' or 'DIM'. The selection of the BRIGHT or DIM state is based on the measured ambient lighting intensity which is compared to a pre-determined threshold. To avoid unnecessary rapid changes between these the bright and dim states is a hysteresis is applied to the threshold.

Alternatively, a plurality of intensity levels may be used, such that the intensity of the LED is maintained at a predetermined level sufficiently above ambient to reliably achieve the desired functionality, whilst minimising nuisance visibility.

In one embodiment the ambient light level may be advantageously measured using optically sensitive components that already exist in the system for another primary function. This has the advantage of minimising component count, hence is beneficial to both cost and reliability. For example, the ambient light level at the light source end may be monitored at the sensor end by measuring the intensity of pixels in the region of the LED position, or the intensity of pixels at the LED position when it is off.

It is possible to determine the distance to an object using the time-of-flight of a light pulse from the source to the object and the reflection from the object back toward the source. Commercially available 'lidar' systems are used in hunting, golf or for general purpose distance measurement. An embodiment of this type of system can be used to supervise the region of interest for intruding objects.

Figure 20:
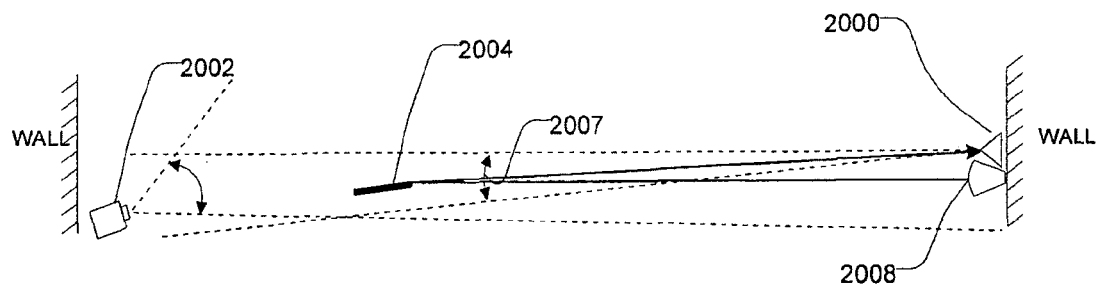
FIG. 20 illustrates an embodiment of the present invention using time of flight measurements to supervise the region of interest.

FIG. 20 illustrates an embodiment of the present invention using time of flight measurements to supervise the region of interest. A pulsed light source 2000 illuminates a region 2002 which includes intruding object 2004. Reflected light 2006 from object 2004, is returned to receiver 2008 that is located near the pulsed light source 2000. Timing circuitry (not shown) is used to control both the light source 2000 and the receiver 2008 and measures the round-trip time for a light pulse from the light source 2000 that is reflected by the object 2004 and returned to the sensor 2008. The distance to the object 2004 can then be determined by a simple calculation. Since the system knows the distance from the light source 2000, to the main system receiver 2002, a fault can be raised if the time of flight measurement indicates that an object is within in the intervening space.

When small particles (up to a few wavelengths across) scatter light, they show little tendency to change the polarisation of incident light. On the other hand large particles and objects e.g. large dust particles, insects, and other large obstructions, especially rough or irregular ones will modify the polarisation properties of the scattered light. Therefore, by using incident light of a known polarisation and a sensor that is polarisation sensitive it is possible to change the relative sensitivity of the system to large as opposed to small particles.

In embodiments of the present invention that use polarisation techniques the system will be fitted with polarisation sensitive sensor such as a camera fitted with a polarising filter either external to the camera or built into the camera housing or optics. Alternatively the face of the sensor could also be fitted with a polarising filter, or the sensor could have inherent polarisation sensitivity.

In certain embodiments, the ratio of, detected light scattered by smoke particles to unwanted ambient light, can be improved by a factor of about 2 by placing a polarising filter ahead of the camera and illuminating the monitored volume with a polarised light source. In this case, the polarisation of the light source and camera filter should be parallel aligned for optimum sensitivity. If the polarisation of either the source or the filter is rotated through 90 degrees, then only particles that modify the polarisation state of the incident light will be detected. In this case there will be a large reduction in sensitivity to small particles, since they do not tend to change the polarisation when they scatter light. However the response to large rough particles or non-specular surfaces will substantially remain. Thus a measure of very large particle density can be obtained.

In the following description, "cross-polarised scattering coefficient" will be the term given to measurements taken in an arrangement in which the polarisation of the light source and the sensor are perpendicular. The measurements taken in an arrangement with the polariser aligned with the light source polarisation will be referred to as the "parallel-polarised scattering coefficient".

As is the case with the parallel-polarised scattering coefficient, the cross-polarised scattering coefficient can take different values depending on the following factors:
  scattering angle relative to the propagation direction;
  the scattering angle relative to the plane of polarisation of the incident light;
  the illumination wavelength;
  the type and quantity of the scattering material.

If the system incorporates means for measuring both parallel-polarised and cross-polarised scattering coefficients, then by analysing the individual measurements and/or comparing their relative strengths the following benefits may be realised:
  Reduced false alarm rate due to airborne insects, spider webs and other small intruding objects.
  Reduced false alarm rate due to airborne dust.
  Large objects intruding into the beam can be identified as such and rejected so as not to cause false alarms.

In systems with automatically movable light sources, the system can use this information to reposition the beam to a more advantageous position or positions away from obstructions.

Figure 24:
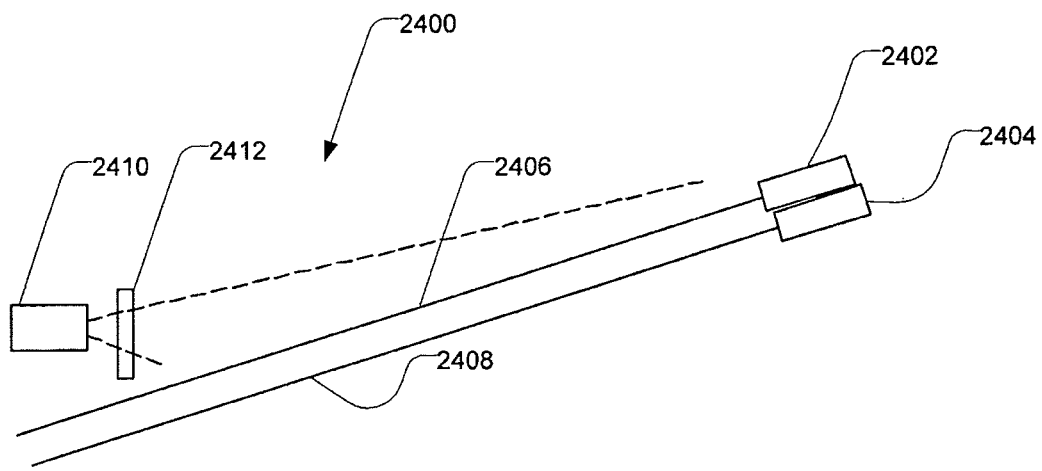
FIG. 24 illustrates a embodiment of an AVSD system using polarisation-based techniques to enable discrimination between large and small particles in an embodiment of the present invention.

FIG. 24 illustrates a system 2400 capable of detecting both the cross polarised and parallel polarised scattering coefficients. The system includes at least one vertically polarised light source 2402 and at least one horizontally polarised light source 2404 which emit respective beams of light 2406 and 2408. The beams 2406 and 2408 are monitored by a sensor 2410, which in this case is a camera and on which is mounted vertically polarised filter 2412. In the present embodiment by selectively powering the vertically polarised light source 2402 and horizontal light source 2404 the parallel polarised scattering coefficient and cross polarised scattering coefficients respectively can be taken. Clearly the system would work with alternative polarisation arrangements.

Figure 25:
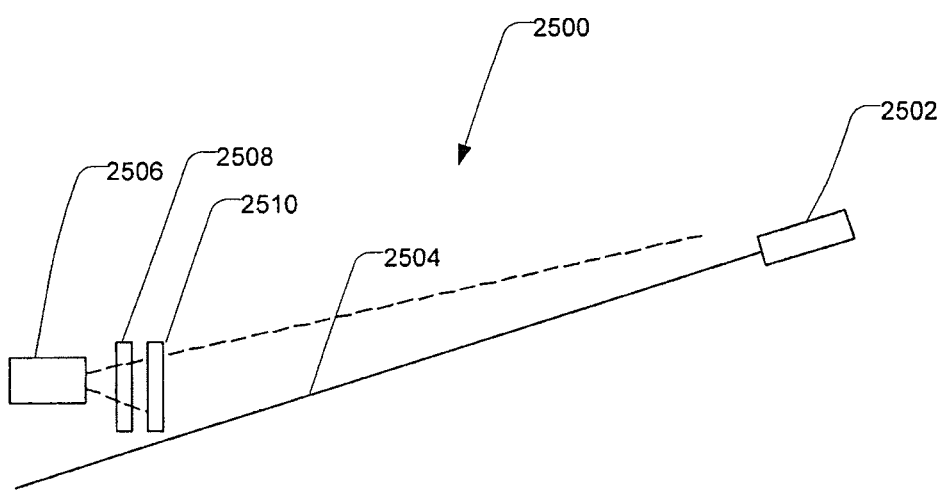
FIG. 25 illustrates a second embodiment of the present invention using polarisation based techniques to perform particle size discrimination.

FIG. 25 illustrates an alternative embodiment which can also be used to measure the parallel polarised and cross polarised coefficients in the system.

In FIG. 25 a system 2500 is illustrated which includes a single polarised light source 2502 which emits a beam 2504. The beam 2504 is monitored by a sensor 2506, which may be a video camera. The sensor 2506 is fitted with a polarising filter 2508 that can have its direction of polarisation controlled by a polarisation rotator 2510. By activating the polarisation rotator 2510, measurements of the cross polarised scattering coefficient and parallel polarised scattering coefficient can be determined. In a preferred embodiment the polarisation rotator 2510 can be of the liquid crystal type. It may also be a mechanical device configured to physically rotate the polarisation filter 2508.

There are other embodiments of such a system that can be created by making various modifications to the present embodiment. For example, the polarisation filter may be fixed and the polarisation direction of the light source may be rotatable in order to project light in the first polarisation direction and a second polarisation direction. In an alternative embodiment the system may be fitted with two cameras with polarising filters each set to monitor the light beam in different polarisation directions. In a third embodiment, double imaging may be employed by using a beam splitter to divide a beam into two to thereby present two identical images to the camera, but one via a parallel polariser and the other via a cross polariser. Alternatively, two of the AVSD systems can be arranged in close proximity each configured to operate in different polarisation orientations.

Another variation is to use circular or elliptical polarisations. As with linear polarisation, matching the filter and polarisation state of the light will allow scattered light from small particles to be received, and using a misaligned (preferably orthogonal) filter and light source polarisation state will reveal the scattered light from the larger, irregular particles.

When the images containing the scattering data are acquired by the system it is still necessary to capture image frames with the light source turned off if the background cancellation techniques, such as those described elsewhere herein are to be used. In this case, the image sequence captured can consist of interleaved normal, cross-polarised and off frames with the off frames used for background cancellation for both "on" measurements. Alternatively a set of parallel-polarised and "off" frames can be captured, followed by set of cross-polarised and "off" frames, or any other sequence. The interleaved scheme is preferred because the two measurements are occurring closer together in time. Also, configurations that employ substantially the same beam path for the measurements are preferred because they avoid errors due to non-homogeneity of the particle density in the volume observed.

It is possible in some embodiments to capture only parallel-polarised and cross-polarised frames in the image sequence without capturing off frames, but this will limit the analysis that can be performed. In this case the cross-polarised frames can be used as if they were the off frames in the background cancellation techniques described in our co-pending application. Such a system can still usefully reject dust and large particles.

This type of system can be advantageously employed in systems with dual cameras or double imaging since both the parallel-polarised and cross-polarised frames can be taken simultaneously.

Also, it is not strictly necessary to use exactly parallel aligned and perpendicularly aligned polarisation orientations, However, the signal processing is more complicated with other alignments. In this case, the two scattering measurements will be linear combinations of the parallel-polarised and cross-polarised values. The parallel-polarised and cross-polarised scattering coefficients may be computed provided the polarisation angles are known.

Once the parallel-polarised and cross-polarised scattering coefficients have been obtained, there are a number of methods that may be used to process the data.

A first method is to ignore the regions of space (i.e. those parts of the beam) with strong cross-polarised scattering response, as these indicate regions which are affected by large particles or objects, i.e. non-smoke particles. In this case the system can be configured to generate fault conditions for action e.g. a call for service. Alternatively, in embodiments capable of moving the beam the system can be configured to steer the beam away from the region. Fixed or adaptive thresholds and delays or other existing decision algorithms can be used to determine when to trigger a fault or steer the beam. This can be applied on a pixel-by-pixel basis along the beam, or on a sector or "virtual detector" basis.

In a second method the cross-polarised scattering coefficients can be scaled and then subtracted from the parallel-polarised scattering coefficients. The resulting scattering data will now be predominantly from the small particles alone, and thus false alarms from dust etc will be reduced. The scaling factor is chosen to obtain adequate cancellation from typical nuisance particles such as dust clouds.

A more elaborate data processing method is to compensate for the time varying particle size distribution of dust clouds. In a typical cloud of dust the particle size distribution will contain relatively more large particles when the cloud is first created compared to a time later on, due to gravitational separation of the dust particles. This can be modelled (for instance) with a fast-attack, slow-decay filter and scaling applied to the cross-polarised scattering response data. This filtered response can then be subtracted from the parallel-polarised scattering data to yield estimated scattering for the particles other than those in the dust cloud. The model can be further improved by allowing for diffusion effects. Those skilled in the art will be aware of applicable filtering methods.

The alarm thresholds, delays or other decision parameters can be varied based on the strength of the cross-polarised scattering response data to reduce the probability of false alarm. In a smoke detection system the "fire" threshold is the smoke level at which the fire alarm is sounded and the fire brigade called. A smoke detector system can also have early warning or pre-alarms to warn of an impending fire condition. These pre-alarms do not normally have the same regulatory requirements as the fire alarm, so therefore it could be acceptable to not indicate a fault when these levels are modified to avoid a response to nuisance materials. Therefore, for some systems it may be sufficient to signal a fault condition only when the fire alarm threshold has needed to be raised to avoid a false alarm.

Figure 26:
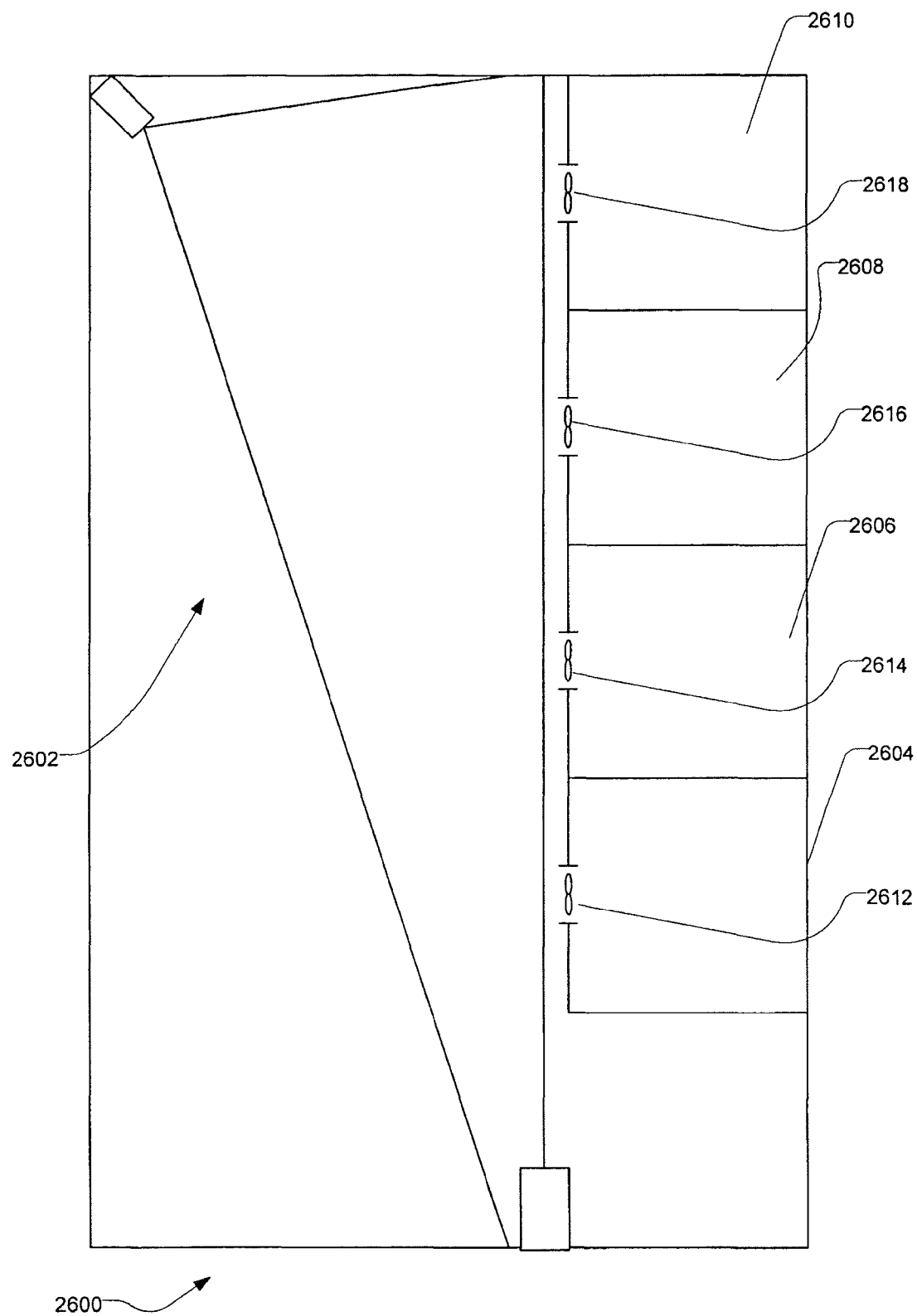
FIG. 26 illustrates an exemplary AVSD system configured to monitor a primary volume and a plurality of separately enclosed secondary regions.

FIG. 26 shows an AVSD system 2600 to monitor a region 2602. As will be appreciated from the previous description, AVSD systems are well suited to monitoring large open areas where a single beam can replace many conventional smoke detectors. However, as in the arrangement shown in FIG. 26 the area being monitored 2602 may additionally include smaller adjoining spaces such as offices 2604, 2606, 2608 and 2610 that also require fire protection. One solution to this problem is to provide means to extract air from the adjoining spaces into the area protected by the AVSD system. In the example of FIG. 26 each office 2604 to 2610 is provided with a respective fan 2612 to 2618 which is configured to pump air from the office into the AVSD monitored volume. The AVSD system 2600 is positioned within the volume 2602 in close proximity to the point of entry of the air from the other volumes. An embodiment of this type of system could be implemented to monitor a plurality of equipment cabinets by, for example, shining a beam of radiation across the top, or along the back of a row of cabinets. Other embodiments could also be used to monitor alcoves in tunnels.

In alternative embodiments ducting could be used to transfer air from the sub-volumes into the main volume 2602.

In some embodiments an AVSD system can be set up to monitor in a backscatter geometry rather than a forward scattering arrangement described in the majority of embodiments herein. These backscatter systems have an inherent advantage over forward scattering systems, in that the system's active (i.e. electrically powered) components all reside at the same end of the system. This clearly has advantages in terms of wiring and other aspects of installation However, backscatter systems have the disadvantage that they are often less sensitive than forward scattering geometries. In fact, measurements of the scattering properties of smoke has revealed that there is of the order of 100 times less light scattered back towards the source than is scattered forward in shallow angles of 1 to 20 degrees, resulting in almost a 100:1 loss of performance.

This large loss of sensitivity can be recovered to some extent by reducing the camera/laser spacing and/or increasing the laser power. However increasing laser power may raise problems of system safety.

In a backscatter geometry, since the laser arrival spot should be in the field of view of the camera, it is possible to add a frame rate based laser safety interlock that would then allow higher laser powers to be used with adequate safety.

A longer focal length lens may also be used to help recover the loss of spatial resolution.

A problem with basic AVSD systems is that objects blocking the field of view of the camera can cause the system to fail to detect smoke. Within the fire protection industry, such a fault condition, if not accompanied by a fault or trouble signal from the smoke detector system is termed a critical fault or critical failure. It is a requirement that approved systems have a very low probability of critical failures. Methods for supervising the camera field of view and detecting fault conditions are described elsewhere in this patent.

Another variation is to simply not use the scattering signal for producing the fire alarm.

Instead the scattering (preferably forward scatter) measurements are obtained by a camera to perform an early warning function, and to provide an indication of the location of the smoke. The smoke detection function (i.e. the fire alarm signal that is used to call the fire brigade or to trigger suppression systems) is generated independently. For example the pre-alarm or early warning can be triggered using the laser that is already part of the AVSD system, by monitoring the laser power arriving at a target. This can be achieved in several ways, as described above, including using a photo-detector at the target, using a corner reflector or retro-reflector at the target and a photo-detector at the laser end. In the event that the beam power detected there is reduced appreciably the beam can be taken to be impeded effectively operating as a beam detector. This arrangement avoids the need for complex camera field of view supervision systems, while retaining most of the benefits of the AVSD system.

A further variation is to use an independent smoke detection system such as an aspirated smoke detector e.g. such as those systems marketed under the trade mark VESDA by Xtralis Pty Ltd, to provide the approved smoke detection function for the building or area, and use one or more AVSD systems to provide early warning and smoke localisation functions.

The inventors have observed that in an AVSD system when there is a large heat source under the path of the laser beam the target spot is caused to vary rapidly in position in a way characteristic of heat shimmer, due to refraction caused by rapid changes in atmospheric density. In one embodiment of the present invention, this positional change can be recognised by processing of the sensor output (e.g. video image) of the target spot or by accurately detecting the received light level at the target spot, and looking for variations in received light level. Recognition of this heat shimmer may advantageously be employed to identify fires from fuels which produce little or no smoke (e.g. ethyl alcohol); or such threats as overheating electrical or chemical processing equipment before a fire occurs.

In order to remove effects such as background movement and light flicker, it is desirable to provide a mechanism for cancelling information in the captured image that is unrelated to light scattering from the laser beam. Many methods may be employed to do this such as taking sequential images; eg. one image with the laser light on and another with the laser light off and subtracting one from the other. This has the advantage of simplicity but is less effective if the background is changing rapidly compared with the frame rate at which images are captured.

A more robust method is to take at least two images of the same scene at the same time but with different filtering means so that the two images taken have a different sensitivity to the radiation scattered from the beam. Such images may be processed by subtraction or other mathematical algorithms to substantially reject background movement, flicker or other variations while still providing sufficient sensitivity to the scattered light from the laser beam.

Figure 26A:
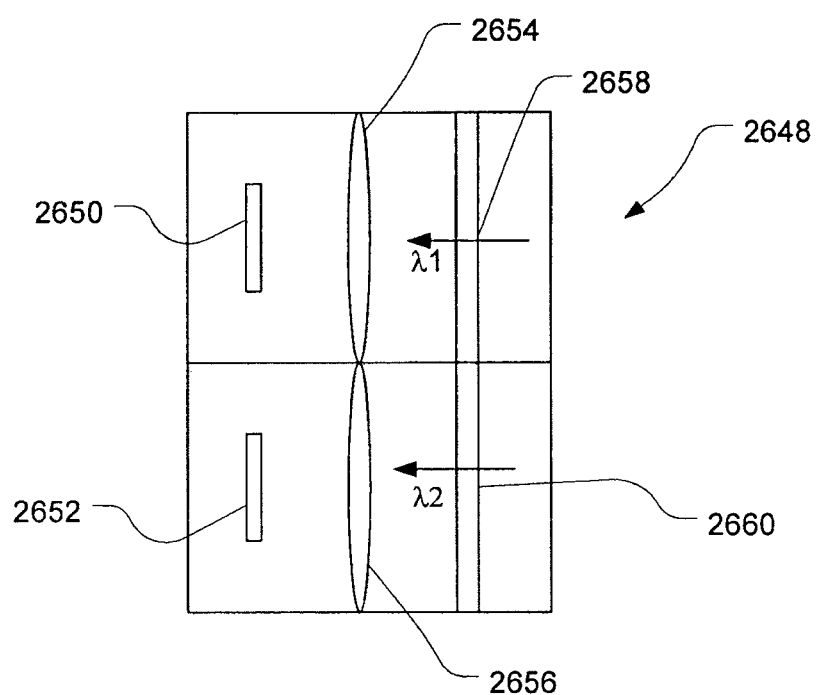
FIG. 26A illustrates a sensor system for use in an AVSD system according to an embodiment of the present invention.

Suitable filtering means can include wavelength filters where at least one filter is designed to pass the scattered laser light while at least one other is designed to pass light at another wavelength. A suitable set up for implementing this method is shown in FIG. 26A. This figure illustrates a sensor 2648 system for an AVSD system including two image sensors 2650 and 2652 each sensor has a respective lens system 2654 and 2656 associated with it. The first sensor 2650 also has a filter 2658 configured to pass a first wavelength EM radiation, whilst the second sensor has a second filter 2660 adapted to allow EM radiation in a second wavelength band to pass.

Another filtering arrangement similar to that of FIG. 26A, uses polarising filters (instead or in addition to wavelength filters) in front of the image sensor elements so that at least one image sensor is sensitive to the same direction of polarisation as the light source while at least one other sensor is less sensitive than the first.

Figure 26B:
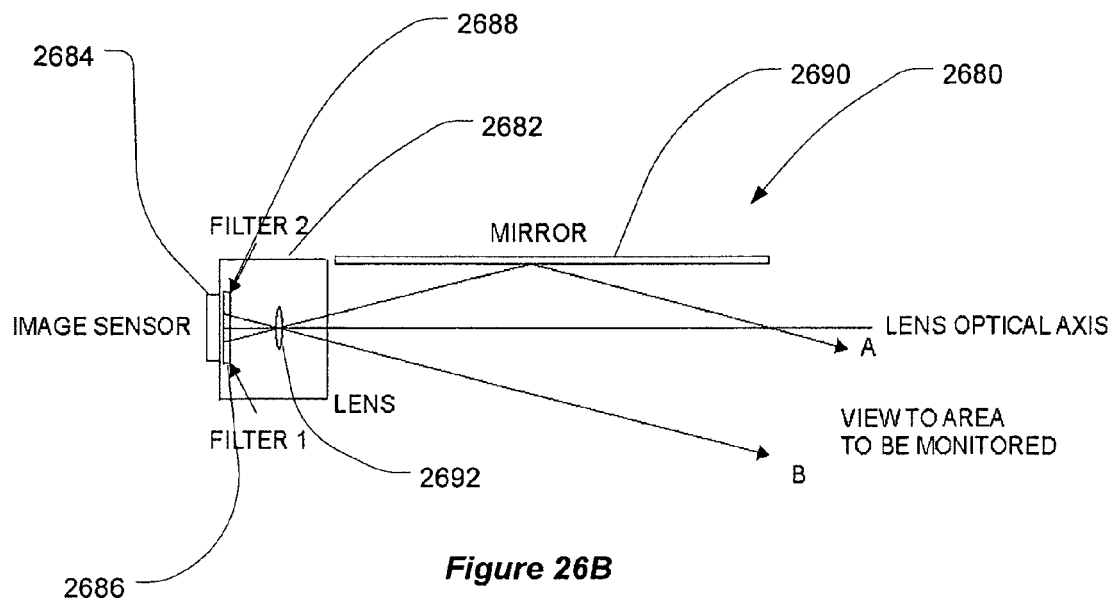
FIG. 26B shows an overview of a second sensor system for use in an AVSD system according to an embodiment of the present invention.
Figure 26C:
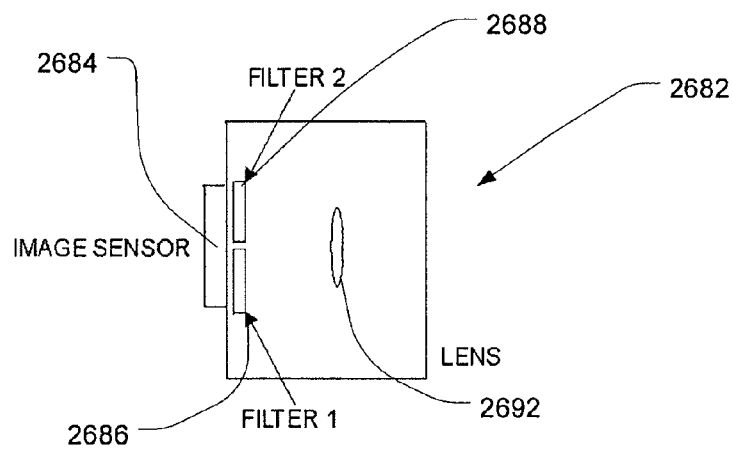
FIG. 26C shows further detail of the sensor arrangement used in the embodiment of FIG. 26B.

A further embodiment combines two or more such filtered images onto one image sensor unit using mirrors or prisms or the like so that light passing through a first (preferably more sensitive) filter is directed to one portion of the imaging chip while at least one image having passed through the second (preferably less sensitive) filter is made to fall upon another part of the image chip. This arrangement has the advantage that two or more images may be recorded simultaneously with only one image sensing chip. FIG. 26B shows an overview of the operation of this type of sensor system 2680, and FIG. 26C shows the detail of the sensor arrangement 2682.

The system 2680 includes a sensor arrangement 2682 which captures a double image on a common image sensor 2684. Some part of the light captured from the scene being monitored is reflected from mirror 2690 through lens 2692. This light (light ray A) then passes through filter 1, 2686 before being captured on a first part of sensor 2684. The light that is not reflected (light ray B) passes through the lens 2692 and then filter 2, 2688 before being captured on a second portion of the sensor 2684. The filters 2686 and 2688 can be either different polarising filters or wavelength filters to implement either of the methods described above. Alternatively one of the filters can be omitted and a filtered and un-filtered path can be obtained.

It should be noted that the mirror is positioned, relative to the lens and image sensor, and aperture thorough which light arrives into the sensor system 2680, such that two images of the a substantially identical scene are captured.

Various background cancellation methods can be used to compensate for changing background conditions. As previously described, the background cancellation algorithm will typically take a sum or average over a number of "emitter on" image frames and "emitter off" image frames.

Prior to the subtraction of the "emitter off" frames from the "emitter on" frames, the "emitter off" frames are scaled by a factor, f, to compensate for variance in illumination levels of the "off" relative to the "on" images. The optimum factor f can be estimated by using brightness information from regions in the image on both sides of the region of interest:

$$f = \frac{\left(\frac{\mu_{on1}}{\mu_{off1}} + \frac{\mu_{on2}}{\mu_{off2}}\right)}{2}$$

where:
μ is the average value of pixel intensity in background regions 1 and 2 located on either side of the region of interest as denoted by the subscripts, the subscripts also denote whether the image is an emitter on or off frame.

The principle can be extended to allow for variations along the path, not just to either side of the path by subdividing the background areas 1 and 2 and region of interest (integration areas) into segments along the length of the beam path and performing the calculations for each subdivision. The segments can be made as narrow as the camera resolution allows.

Alternatively the value f can be calculated using:

$$f = \frac{\mu_{on1} + \mu_{on2}}{\mu_{off1} + \mu_{off2}}$$

or $$f = \left(\frac{\mu_{on1} \cdot \mu_{on2}}{\mu_{off1} \cdot \mu_{off2}}\right)^{1/2}$$

In another embodiment the background "scattering" level (or grey levels or smoke) computed from the background regions can be subtracted from the readings computed from the region of interest. This works on the principle that temporal lighting variations that cause small smoke readings will generally affect the background regions in a similar way to the region of interest (integration region). By performing the same calculations on background regions, an estimate of the errors produced in the integration area can be obtained and subtracted from the readings of the region of interest.

For example, the corrected grey level in the region of interest can be calculated using the following formula:

$$G_{Corrected} = I_{on} - I_{off} - \frac{1}{2}(B_{1on} - B_{1off} + B_{2on} - B_{2off})$$

where:
$G_{Corrected}$ is the grey level in the region of interest caused by scattering when corrected for background scattering.

$I_{on}$ and $I_{off}$ are the total uncorrected grey levels in the integration area in a laser on or off frame (or average of on or off frames) as designated by the subscripts B is the total value of pixel intensity in a either background region 1 or 2 (as denoted by subscripts), in either a laser on or laser off frame as designated by the subscripts.

In this example, the average of the two scattering values $(B_{1on}-B_{1off})$ and $(B_{2on}-B_{2off})$ obtained from the two background regions (1 and 2) are subtracted from the scattering values from the integration area $(I_{on}-I_{off})$. These calculations may be done using individual pixel values, raw grey levels integrated across the beam path, final smoke values or at any intermediate step, with varying degrees of computational effort.

For all of the above methods, the background regions should preferably be chosen so as not to contain undesirable characteristics such as saturation, or localized flicker or noise. Individual pixels or areas may be excluded. In some cases usable pixels may only be present on one side of the integration area.

It is worth noting that even in environments where rapidly changing lighting levels are not a problem, the cancellation methods described here may still have an advantage over simple subtraction, namely that of cancelling out unwanted scattered light from the laser, which would otherwise lead to a constant "background" smoke reading in the absence of smoke. These background cancellation methods described cancel the unwanted scatter in the integration region, provided that the scatter in the integration region is approximately equal to the average of the scatter in the background regions. This condition is expected to be the case if the scatter was due primarily to non-specular reflections.

Another method is to simply ignore (e.g. either zero or limit the values) those parts of the integration area where the corresponding "background scattering" is significant or excessive. The threshold at which this occurs could be related to, or derived from, the fire alarm threshold. The intention being to avoid false fire alarms. If a condition with elevated background scattering levels persists for an excessive length of time then a fault should be raised so the condition can be corrected. Systems with automatic beam steering, as described above, could attempt to self-correct by choosing a different beam position, before raising a fault.

In certain embodiments it may be advantageous to combine the above mentioned methods, so that small disturbances are compensated for, and larger ones where compensation might be inadequate are simply suppressed. In this way, the fire alarm level need not be compromised and the false alarm rate for the fire decision is minimized, but early warning continues to operate as best it can, and the system will signal a fault less often.

As is typically the case with smoke detection based on light scattering, dust or other large particles in the beam can give rise to false alarms. The inventors of the present invention have identified that in an AVSD system such particles typically correspond to individual pixels within the beam integration region that contribute disproportionately largely to the total received light signal. On the other hand, smoke tends to spread out and become distributed resulting in a "smoother" image.

This property of large particles can be taken advantage of by implementing methods for recognizing the presence of dust, e.g. by detecting peaks in scattering relative to the prevailing time average, nearby spatial average, or both.

Exemplary embodiments of such techniques will now be given, in these examples, the data samples used are background-cancelled, pixel wise grey level or scattering values. In alternative embodiments, instead of using the individual pixels, these filtering techniques can be performed on aggregate data such as an array of scatter vs. pixel radius.

(a) Temporal Transient Filtering

In summary this example operates by the signal from each pixel in the integration area (after background cancellation) being compared with previous and/or subsequent samples. When the value in question exceeds the average by a pre-determined threshold, it is ignored e.g. by clipping, discarding or replacing it with a local average.

This analysis can also be extended to allow rejection of short runs of excessive scattering. The calculated average may be obtained using a combination of samples captured before and after the sample being filtered.

(b) Spatial Transient Filtering

In an example using spatial transient filtering, the signal from each pixel in the integration region (after background cancellation) can be compared with the average of adjacent pixels. When the pixel value in question exceeds the mean by more than a pre-determined threshold, it can be ignored, e.g. by clipping or discarding it.

This analysis can also be extended to allow rejection of short spatial runs or regions of excessive scattering. Since the beam length associated with a given pixel can vary greatly from one end of the beam to the other, it can be advantageous to vary the maximum allowed run length accordingly.

In one form the threshold can be determined as a multiple of the standard deviation of values from pixels near the pixel in question. Therefore the system will tend to respond to events that materially exceed the random noise from the system. Other thresholds either based on a statistical quantity associated with the system or an absolute or empirically determined parameter can also be used.

(c) Statistical Analysis

Statistical analysis can also be used to discriminate between dust derived scattering signals and smoke derived signals.

The inventors have determined that large particles tend to produce more temporal and spatial variation of the received scattered light than do small particles. Therefore, it is possible to correct scattering readings to compensate or at least partially compensate for the contribution due to dust or other large particles. Although many relationships or formulae could also be used, the preferred method is based on a mathematical model of the scattering contributions from dust and smoke.

Before the correction method is described, some definitions and the model need to be given. The model, and calculations that are performed are based on individual pixels or groups of nearby pixels with substantially similar statistics.

Assume that the population of scattering particles in the volume of interest can be divided into two categories, small smoke like particles and larger particles that are presumably dust. The particle size distributions may overlap. The total scattering signal received is a combination of scattering from the two populations.

$$\overline{S}=\overline{S_1}+\overline{S_2}$$

Where:
$\overline{S}$ is the total average scattering signal over a period of time and
$\overline{S_1}$ is the average scattering signal from the smoke and
$\overline{S_2}$ is the average scattering signal from the dust.

The total standard deviation of the received scattering signal samples is $$\sigma_{Total}^2=\sigma_{Background}^2+\sigma_S^2$$

Where:
$\sigma_{Total}$ is the standard deviation of the received scattering signal samples over a period of time,
$\sigma_{Background}$ is the contribution from the system that is not associated with scattering in the volume of interest (background lighting variations, shot noise, other electrical noise)
$\sigma_S$ is the contribution from scattering processes, caused by particles moving within the volume of interest.

(The volume of interest is defined as the intersection of the laser beam and the field of view of the pixel or pixel group in question.

The value $\sigma_S$ is itself comprised of contributions from the dust and smoke particle populations.

$$\sigma_S^2=\sigma_1^2+\sigma_2^2$$

Where:
$\sigma_1$ is the contribution from smoke within the volume of interest and
$\sigma_2$ is the contribution from dust within the volume of interest.

Also, we will use the usual definition for relative standard deviation:

$$R_X=\sigma_X/\overline{X}$$

Where:
$R_X$ is the relative standard deviation of the population of samples of X
$\sigma_X$ is the standard deviation of the population of samples of X
$\overline{X}$ is the mean of the population of samples of X Note that for the current purpose, estimates of these and other quantities will be used interchangeably with exact values (In general only estimates will be available.)

Using the naming convention developed above we define:
$R_1$ as the relative standard deviation for smoke, and
$R_2$ as the standard deviation for dust.

Figure 27:
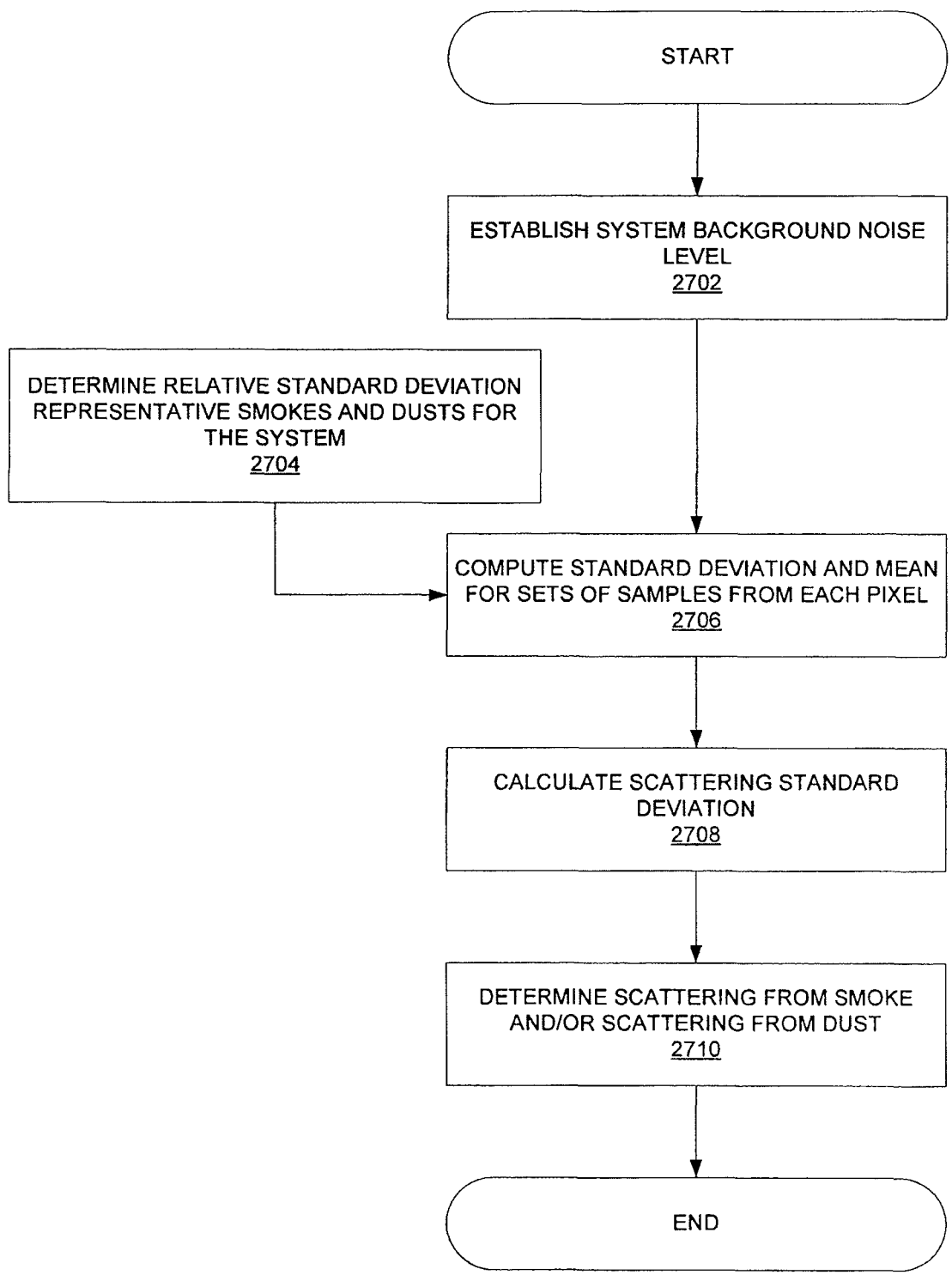
FIG. 27 is a flowchart representing steps in a method for correcting for dust in an AVSD system according to an embodiment of the present invention.

Using the above definitions, the method 2700 for correcting for dust can be implemented as illustrated in FIG. 27, as follows:

Firstly, in step 2702 the system establishes the system background noise level $\sigma_{Background}$. This is preferably conducted individually for each pixel and is calculated as the standard deviation of pixel values with the samples acquired at a time when there are very few scattering particles in the beam.

Once this is done, in step 2704 the relative standard deviation (R) values for representative smokes and dusts for the particular system configuration can be established. In general $R_{Dust}$ should be greater than $R_{Smoke}$ since the particles are larger and cause more variation. The material used should be ones that produce the highest R-values for any smoke, and the lowest R-value for any dust. This is to avoid overcorrecting the readings and reducing the sensitivity to smoke in the presence of dust. Those skilled in the art will recognise opportunities to trade off dust rejection performance against smoke sensitivity and the risk of false negative decisions.

The relationship $\sigma S = \sqrt{\sigma_{Total}^2 - \sigma_{Background}^2}$ can be used to find the standard deviation component attributable to each material and to find the corresponding R using the above defined definitions. The value of R should be substantially independent of particle concentration, so high concentrations (although not so high that secondary scattering is a problem) are best used to reduce the errors in measurement.

These R values may only be applicable for one pixel or region of pixels. This is because there can be considerable variations from pixel to pixel, e.g. due to the different length of the beam visible to pixels in different parts of the integration region.

However the determination of R values for smoke and dust need only be done once for a representative system. Once one set of R-values are established, corresponding values for non-identical systems could then be calculated or experimentally determined.

The background noise level ($\sigma_{Background}$) may vary with lighting conditions. So while it is possible to use a fixed value, it is better to use a value that depends on lighting conditions. This could be done by a formula, a look-up table or by measurements taken during conditions known to have a low concentration of scattering particles or by using the date from image frames taken without active illumination, i.e. "off frames".

Next in step 2706 the standard deviation $\sigma_{Total}$ and mean $\overline{S}$ of sets of background-cancelled samples from each pixel are computed over short time periods (typically 1 to 10 seconds.)

In step 2708 using the established $\sigma_{Background}$ and the latest $\sigma_{Total}$, $\sigma_S$ is then calculated:

$$\sigma_S = \sqrt{\sigma_{Total}^2 - \sigma_{Background}^2}$$

Then, in step 2710, using the established $R_1$, $R_2$ and the latest $\sigma_S$ and $\overline{S}$ the following two equations can be formed:

$$\sigma_S^2 = R_1^2 \overline{S_1}^2 + R_2^2 \overline{S_2}^2$$

$$\overline{S} = \overline{S_1} + \overline{S_2}$$

There are two unknowns $\overline{S_1}$ (scattering from smoke) and $\overline{S_2}$ (scattering from dust)

Solution for $\overline{S_1}$ is as follows:

$$\overline{S_2} = \overline{S} - \overline{S_1}$$

$$\sigma_S^2 = R_1^2 \overline{S_1}^2 + R_2^2 (\overline{S} - \overline{S_1})^2$$

-continued let $A = R_1/R_2$ and $B = R_S/R_2$ $$B^2 \overline{S}^2 = A^2 \overline{S_1}^2 + (\overline{S} - \overline{S_1})^2$$

$$0 = (1+A^2)\overline{S_1}^2 - 2\overline{S} \cdot \overline{S_1} + (1-B^2)\overline{S_1}^2$$

$$\overline{S_1} = \overline{S} \cdot \frac{1 \pm \sqrt{1-(1+A^2)(1-B^2)}}{1+A^2}$$

$$\overline{S_1} = \overline{S} \cdot \frac{1 \pm \sqrt{A^2 B^2 - A^2 + B^2}}{1+A^2}$$

Since $\overline{S} > \overline{S_1}$, the only physical solution is $$\overline{S_1} = \overline{S} \cdot \frac{1 - \sqrt{A^2 B^2 - A^2 + B^2}}{1+A^2}$$

Generally the factor A is small. Therefore an acceptable approximation can then be made $$\overline{S_1} = \overline{S}(1-B)$$

$$\overline{S_1} = \overline{S}(1 - R_S/R_2)$$

If required, $\overline{S_2} = \overline{S} - \overline{S_1}$ gives the estimated contribution from dust.

Using the above method, a problem can arise when the scattering signals are very small (or zero). In this case the error in the term $R_S$ becomes very large, due mainly to the large relative error in $\overline{S}$. In the extreme practical case, a division by zero error can occur. This problem can be addressed in certain embodiments by modifying the dust correction at low scattering levels. For example, the following equations can be used:

With $$\overline{S} < S_A, \qquad \overline{S_1} = \overline{S}$$

$$S_A \leq \overline{S} < S_B, \quad \overline{S_1} = \overline{S}\left(1 - \frac{\overline{S} - S_A}{S_B - S_A} R_S / R_2\right)$$

$$\overline{S} > S_B, \qquad \overline{S_1} = \overline{S}(1 - R_S / R_2)$$

The values $S_A$, is a threshold at which no correction is to be performed and $S_B$ is a second threshold at which the correction is allowed to act fully, and are chosen so that system noise does not unduly affect the behaviour at any point. Many alternatives will be obvious to those skilled in the art.

Instead of using the individual pixels, this process can be performed on the array of scatter vs. pixel radius, or other aggregate data.

Another variation to this method that can be used involves a similar process, but which is applied to spatial rather than temporal variations in pixel value. In a further variation, a combination of samples obtained over time and space can be used to increase the total sample size. This reduces the estimation errors in the statistics resulting in better rejection of dust and more accurate smoke readings.

Yet another variation involves taking advantage of the Gaussian scattering sample distribution that can arise with dust. When large particles transit the beam, a bright flash is produced. This is distinct from the random fluctuations caused by electrical noise processes or shot noise from the scene. The distribution of scattering readings in the absence of particles is approximately Gaussian since it is the sum of many uncorrelated sources. Likewise, the distribution of scattering readings in the presence of detectable levels of small particles tend toward a Gaussian shape since there are typically large numbers of particles in the beam. However, with large particles at a detectable concentration, the number of particles present will typically be far less than when smoke is present. Therefore the distribution may show some kurtosis and skew.

In particular, the inventors have determined that a fat tail on the positive side of the distribution can be expected. Because of this, it can be advantageous to use higher moments of the distribution than variance or standard deviation to determine the scattering contribution of smoke as distinct to dust. For example skew or kurtosis may be used in a method similar to the above. The skew or (excess) kurtosis may be expected to be near zero for clean air or smoke, but be increasingly positive for increasing concentrations of dust. The skew or (excess) kurtosis may therefore be used to correct the scattering reading back to what it would have been without the dust.

The basic AVSD system disclosed in our earlier patent applications, measure smoke particle concentration vs. position along the laser beam. This data ultimately needs to be converted into a fire alarm signal or multiple signals, indicating the general location of the smoke, and the level of alarm. As will be appreciated by those skilled in the art a fire alarm system will typically have 2 early warning or pre-alarm levels, a fire alarm level for evacuation and calling the fire brigade and a fourth level to activate automatic suppression systems.)

The relevant data available from the AVSD system as described in embodiments herein, and in our co-pending and previous patent applications includes an array of smoke concentration levels vs. an array index that represents the distance measured in pixels from the light source. Note that this choice of pixels is arbitrary, but was chosen since it substantially preserves the available resolution for subsequent processing steps.

One method previously presented is to divide the usable length of the beam into segments representing "virtual detectors". The smoke level for each virtual detector is computed as a length weighted average the smoke readings over the range of array indexes that fall with the corresponding segment.

$$S_{Segment\ n-m} = \frac{\sum_{r=n}^{m} S(r)L(r)}{\sum_{r=n}^{m} L(r)}$$

where:
$S_{Segment\ n-m}$ is the smoke level in the segment corresponding to array indices n to m,
S(r) is the smoke level at array index r
L(r) is the length of the beam represented by array index The segments corresponding to each virtual detector can be made to overlap to some extent. While this method is quite workable, it can result in excessive dilution if the segments are made too large, and excessive noise if they are made too small. For example, if a segment has a length of 5 m along the beam, but the smoke plume is only 1 m across, the measured smoke density will be 5 times lower than actually exists in the plume. However, if small segments of 1 m lengths were employed the noise levels would be higher (due to less averaging), and the system would be less capable of detecting distributed smoke.

Figure 27A:
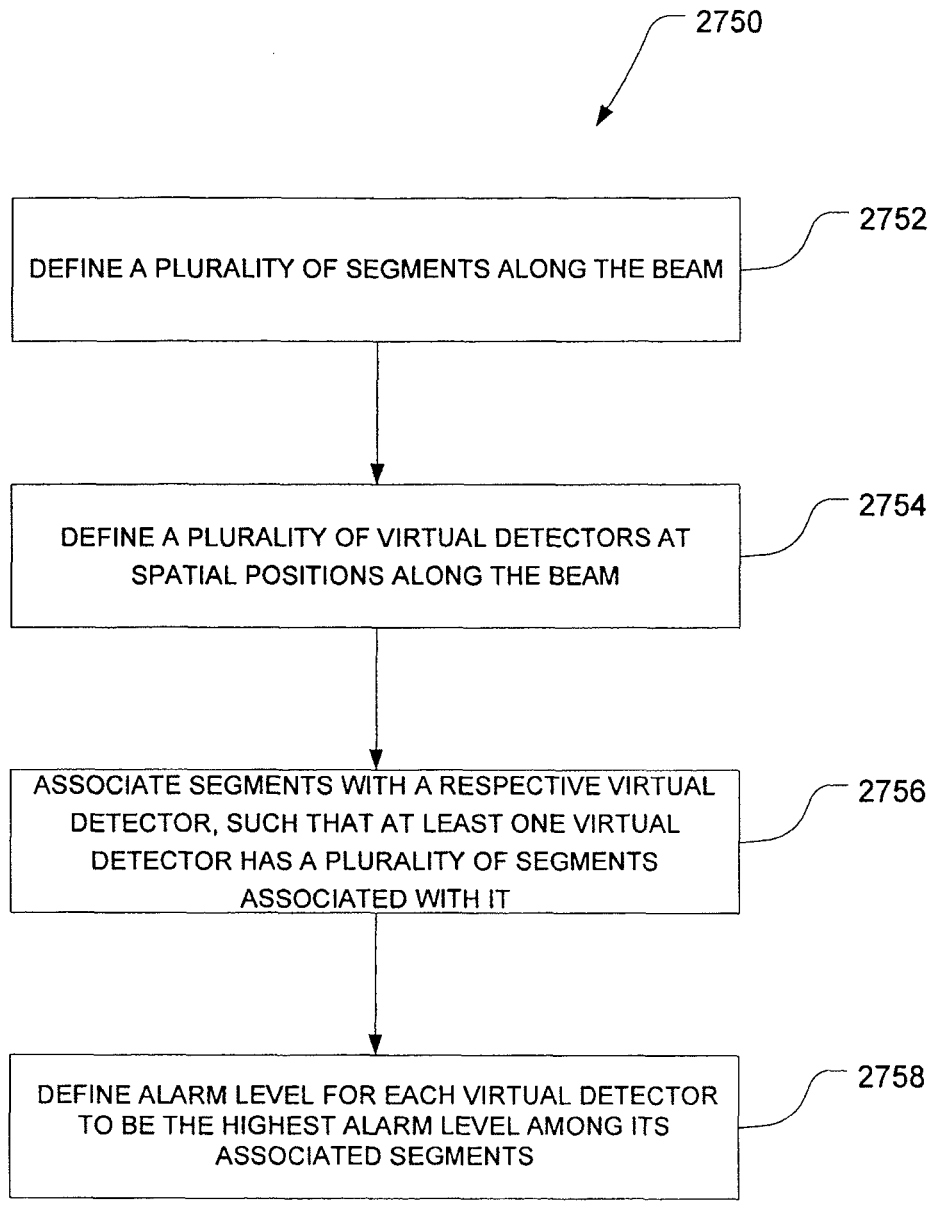
FIG. 27A is a flowchart representing steps in a method of implementing addressability in an AVSD system according to an embodiment of the present invention.

An improved method for handling this situation is illustrated in the flowchart of FIG. 27A.

In this method 2750, instead of using adjacent (or overlapping) segments of only one size, a range of segments of different sizes are defined in step 2752. Each segment has a unique spatial length and position along the beam. The segments can overlap each other in small (or large) increments along the beam. Now, for any given smoke plume position and width, there will be a defined beam segment that is a good match for it which will yield the highest signal to noise ratio.

Each segment so defined has an associated alarm decision logic (for example using the same threshold and delay scheme as previously employed). As will be appreciated the alarm thresholds of each segment must be suitably scaled to take account of the differing noise levels that result from the different averaging lengths. (Otherwise false alarms will occur).

As mentioned above a plurality of virtual detectors can be defined in step 2754 e.g. to correspond to detector addresses within a fire detection system to which the system belongs.

Next in step 2756 each segment is associated with a virtual detector. This is can be done, for example, by finding the closest virtual detector location to the spatial centre of the segment.

In the final step 2758 the alarm level for a given virtual detector is then calculated as the highest alarm level of all the segments associated with it.

In an alternative embodiment a smoke level for a virtual detector is computed to be the highest smoke level detected in all the segments associated with it. This smoke level is then passed to alarm decision logic that is associated with the virtual detector, rather than the segment. The higher noise levels that the narrow segments will exhibit can be handled by suitably scaling down the readings. This has the advantage of being able to track a drifting plume for the duration of alarm delays.

A third, alternative is to compute an instantaneous alarm level for each segment e.g. compares smoke to an alarm threshold with no delay), then to pass the highest alarm level of any segment associated with a given virtual detector to alarm delay logic associated with the virtual detector.

As will be appreciated the, the segments have been described as effectively as windows or rectangular filters (i.e. equal weighting has been given to all included data points within the segments). However, Gaussian or other weighting schemes can also be used, and may show slightly improved correlation to typical smoke plumes.

Because AVSD systems are well suited to use outside or in large open areas the affect of sunlight on the system must be considered. Typically sunlight can cause either saturation of the detector or reduced sensitivity (by introduction of noise) in an AVSD system. An additional way to avoid or at least ameliorate the affect sunlight or other stray light on an AVSD system is to carefully select the wavelength at which the AVSD system operates. More particularly the wavelength of the light emitter or light detection apparatus can be tuned to a wavelength that corresponds to either an atmospheric or solar spectral absorption line, for example there is a narrow absorption line in the solar absorption spectrum at about 656 nm caused by Hydrogen which may be used. For this technique to be effective a suitable filter should be fitted to the camera that is centred on the absorption line, and preferably be not wider than the width of the line.

If using atmospheric absorption, to prevent stray light affecting the system the ultra-violet part of the electromagnetic spectrum can be advantageously employed. Wavelengths shorter than about 400 nm are attenuated significantly by the earth's atmosphere and below 300 nm the solar irradiance at ground level is attenuated by many orders of magnitude. This can be taken advantage of by using a Sub-300 nm light source in an AVSD system. For example, a system with a laser wavelength of 266 nm may not even require a narrow band filter, just a daylight blocking filter would be sufficient. Such a system may be capable of operation in full sunlight with little or no performance penalty.

As previously discussed dust signal rejection is important to system reliability. The inventors have identified several methods of enhancing dust rejection in an AVSD system. These include:

Determining a fractional light loss to scattering ratio at a given wavelength

Determining scattering ratios at multiple wavelengths

Combine multiple wavelength fractional light loss/scattering ratios

Determining scattering ratios at different polarisations

Determine scattering levels at different scattering angles (e.g. by using multiple cameras and/or beams)

The inventors have identified that large particles such as dust scatter comparatively strongly at shallow angles. Lab tests conducted by the inventors have shown that, for the same side scatter magnitude, using a wavelength of 800 nm polarised perpendicular to the plane of scattering, dusts scatter around 10 to 100 times more than small particle such as smoke for angles in the range of 1 to 4 degrees. For this reason AVSD systems will preferably incorporate measures to reduce large particle sensitivity.

One method uses the ratio of light scattered from the beam to fractional light loss. Lab tests have shown this ratio to be of the order of 30 (10 to 100) for dusts and around 1 to 2 for typical small particle cellulose smokes. Some smokes produced from hydrocarbons (n-heptane/toluene mix, and plastics) were found to produce a ratio of around 10, but still less than most dusts. These high-ratio smokes usually also produce at least 10 times more scattering than other smoke types, so a dust rejection method based on this ratio can also be used to correct the over-sensitivity to these smokes.

Figure 28:
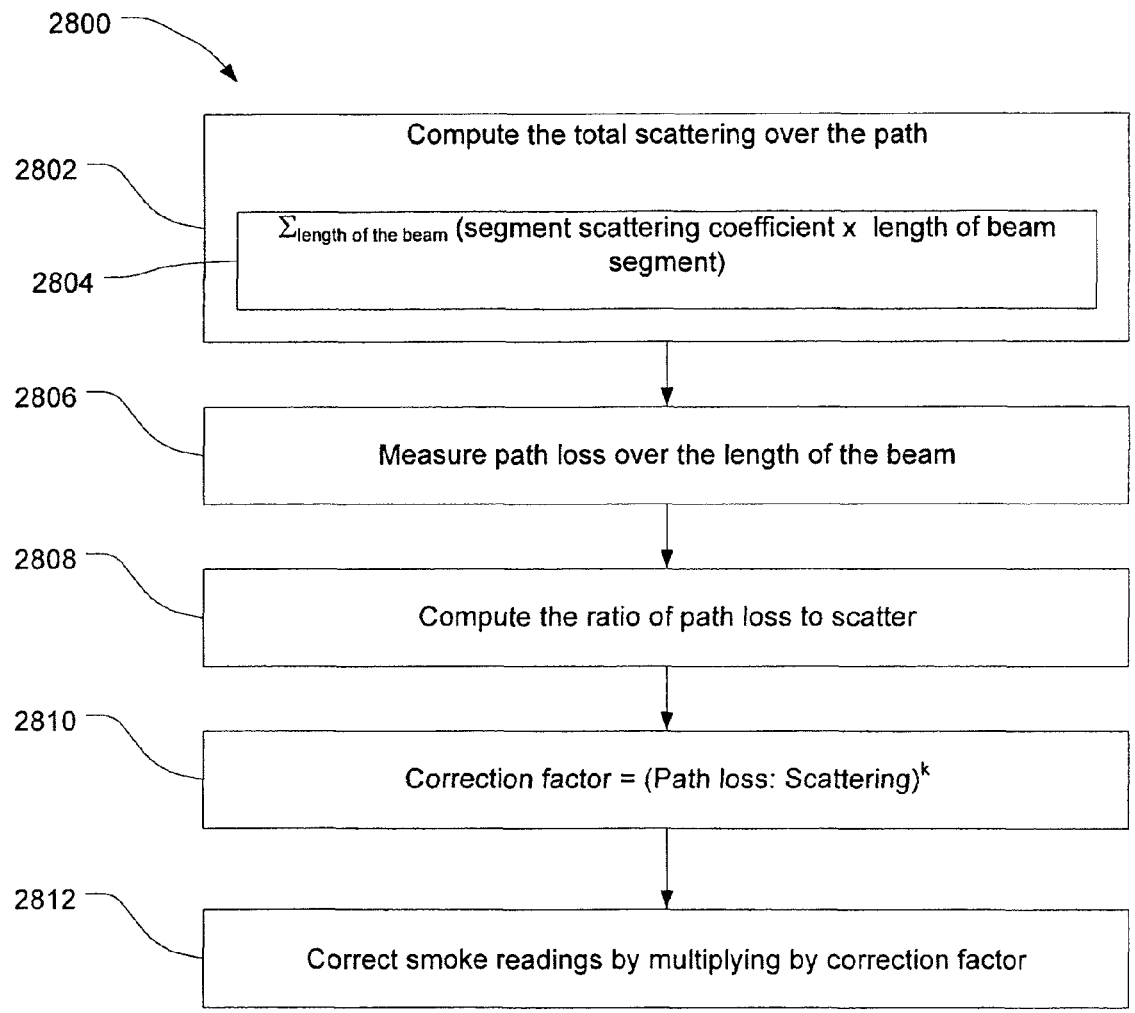
FIG. 28 is a flowchart depicting steps in a method of correcting smoke readings on the basis of measured path-loss data in an embodiment of the present invention.

In a preferred method, illustrated in FIG. 28, the scattering levels detected can be corrected using the scattering to fractional light loss ratio, as follows:

In a first step 2802 the total scattering over the path is computed. This is preferably performed as indicated in step 2804 by multiplying the determined scattering coefficients by the length of beam segment over which they apply, and summing along the length of the beam.

Next in step 2806 the fractional light loss over the length of the beam is determined.

Following this step, in step 2808 the ratio of fractional light loss to scatter is computed. This ratio is then raised to a chosen power, k, which is usually between 1 and 2 to determine a scattering correction factor in step 2810.

The correction factor is used in step 2812 to correct the scattering derived smoke readings. The correction is performed by multiplying the smoke reading by the correction factor.

The power k can be used to tune the degree of dust rejection desired. Although there is generally a trade off between dust rejection and the risk of reducing smoke responses, if k is set to a value of 1, this results in the scattering reading being corrected back to approximately the path loss system, which will always respond to smokes of any kind. Higher values of k may be used but create a risk of rejecting a genuine alarm condition. Other methods of using the relationship between scattering and fractional light loss ratio is an indicator of the type of scatterer (e.g. type of smoke, or smoke or dust etc.) being encountered may be devised.

It should be noted that in order to effectively use the above method the fractional light loss measurement should be have about the same accuracy as the system sensitivity to scattering. Thus if it is desired that the system be able to reject dust with scattering levels corresponding to 1%/m, then with 1%/m smoke and 5 m long sectors, the fractional light loss (with smoke) will be about 5%. In order for the corrected smoke reading to not be in error by more than say 20%, the fractional light loss must be accurate to about 1%.

Thus, excessive drift in fractional light loss measurement sensitivity could mask a genuine alarm condition. This sets a stability requirement for the path-loss measurement system, which is not easily achieved. However, the present inventors have devised several methods or techniques that may provide the required sensitivity and stability.

The first method generally involves projecting a beam through the volume of interest (preferably the same beam as used for the scattering measurement), directly onto a photocell. Optionally the photocell can be fitted with wavelength and/or polarisation filters to reduce unwanted light.

Also, light-collecting optics may be employed allowing the use of a small cell with a large laser beam.

In order to operate with suitable sensitivity the photocell or collecting optics must intercept the entire beam cross section. If it does not, then interference effects and small physical disturbances may cause fluctuations in the received laser power. Moreover the light collecting area of the sensor and/or optics must be sufficiently large to allow for alignment changes that may occur, e.g. movement caused by building movement and vibrations etc.

Also the light collecting area must have a sufficiently uniform sensitivity across its area so that the whole beam is measured evenly.

Figure 29A:
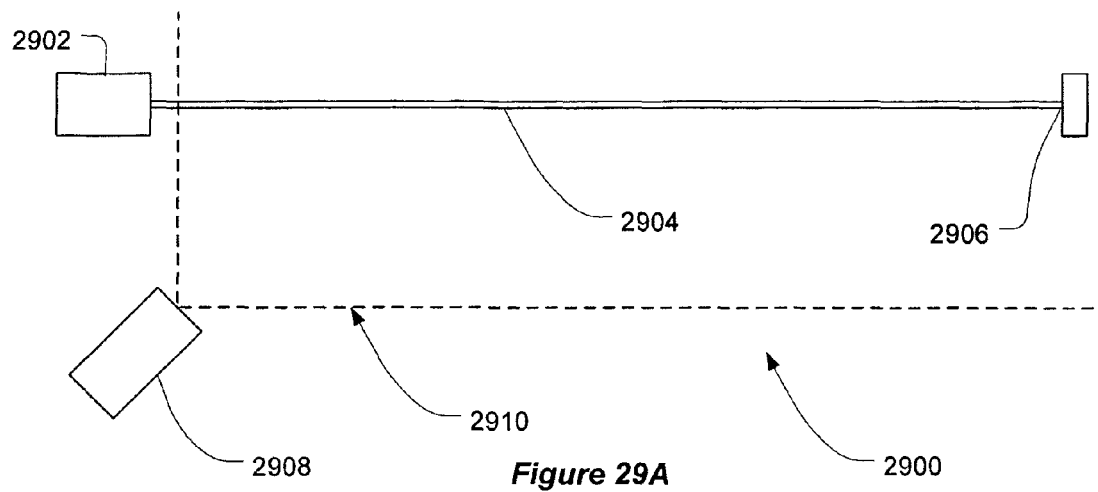
FIG. 29A illustrates an AVSD system of an embodiment of the present invention capable of measuring fractional light loss.
Figure 29B:
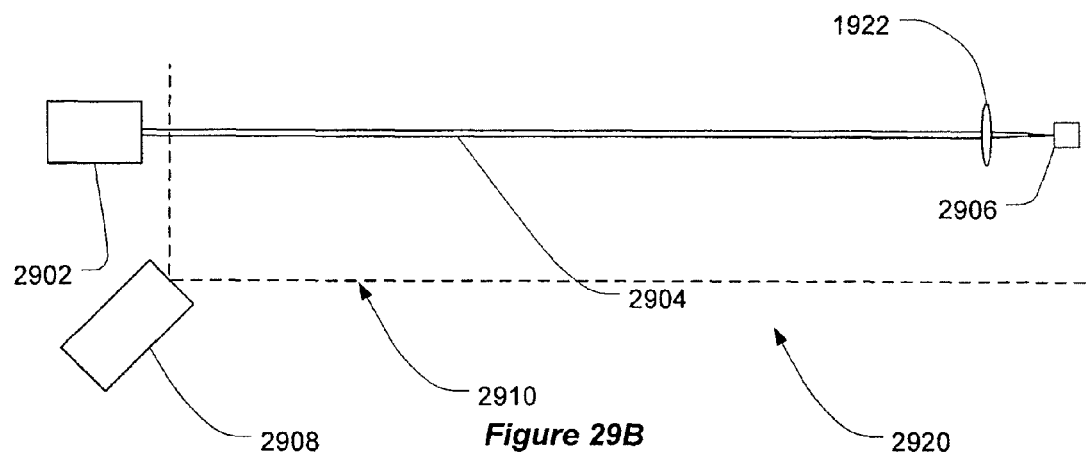
FIG. 29B illustrates an AVSD system of a second embodiment of the present invention capable of measuring fractional light loss.

FIGS. 29A and 29B illustrate suitable systems for implementing the above mentioned techniques.

FIG. 29A illustrates a system 2900 having a light source 2902 which emits a beam of light 2904. The beam terminates on a photo-sensor 2906, which measures the received laser power. As noted above the photo-sensor 2906 has sensor area larger than the beam's 2904 cross section so that it can capture the entire beam reliably. The beam 2904 is monitored by a second light capturing device, e.g. a camera 2908, configured to monitor a field of view 2910 and send output signals for use in performing particle detection in a manner described elsewhere herein and in our earlier patent applications.

FIG. 29B illustrates a system 2920 very similar to that of FIG. 29A (and like components have been like numbered), except that the beam of light 2904 emitted by the laser 2902 passes through imaging optics 2922 placed before the photo-sensor 2906. The imaging optics 1922 have a light gathering area larger than the beam's 2904 cross section so that it can capture the entire beam reliably and focus it onto the photo-sensor 2906. Because of the presence of the optics 2922, the size of the photo-sensor 2906 can be reduced. Similarly the beam 2904 is monitored by a second light capturing device, e.g. a camera 2908, configured to monitor a field of view 2910 and send output signals for use in performing particle detection in a manner described elsewhere herein and in our earlier patent applications In an alternative embodiment the laser beam can be projected through the volume of interest (preferably the same beam as used for the scattering measurement) onto a reflective target. The power of the received reflected laser beam can be monitored at the laser end.

If the target is a specular retro-reflector e.g. a mirror corner cube or a carefully adjusted plane mirror, similar factors for ensuring optimal and steady light capture to those described in relation to the systems of FIGS. 29A and 29B should be accounted for. However, if the target is a non-specular reflector (eg, a rough surface of a retro-reflector composed of a large number of small reflectors) then there are different requirements for achieving high stability, since it is impractical for the photocell (or collecting optics) to intercept the return entire beam.

Figure 30:
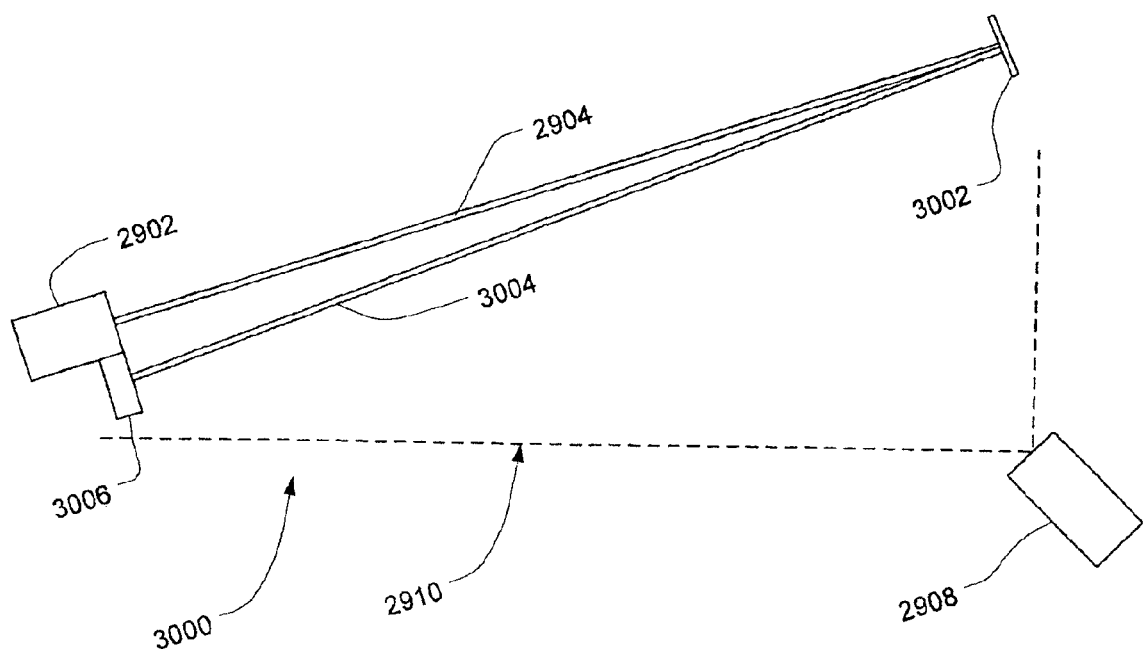
FIG. 30 illustrates an AVSD system of a further embodiment of the present invention capable of measuring fractional light loss.

An example of a system implementing such a method is illustrated in FIG. 30. The system is similar to that of FIGS. 29A and 29B (and like components have been like numbered). The system differs from the previous embodiments in that the system 3000 includes a reflector, in this case a flat mirror 3002 that intersects the beam of light 2904 and reflects a return beam 3004. The return beam is received by a photo-sensor 3006 mounted next to the laser 2902. It will be appreciated that imaging optics may also be used with this embodiment. As with the previous embodiments the beams 2904 and 3004 are monitored by a second light capturing device, e.g. a camera 2908 configured to monitor a field of view 2910, that sends output signals for use in performing particle detection in a manner described elsewhere herein and in our earlier patent applications As with the previous embodiments, to achieve suitable stability, the reflective target area and photo-sensor must be sufficiently large to allow for alignment changes that may occur with building movement etc. In addition the reflective target's light receiving area must be sufficiently uniform in reflectivity.

In the cases where non-specular reflectors are used additional measures must be taken to ensure that laser "speckle" does not cause too much variation Laser "speckle" is an interference effect resulting from multi-pathing, i.e. a situation where light can travel from source to destination by different paths. In practice, this causes random bright and dark patches or a "speckle pattern" to appear in the beam's "spot".

Suitable methods for reducing variations due to speckle are generally based on averaging a large number of uncorrelated speckle peaks and troughs. The inventors have devised the following exemplary techniques:

Use as large a photo-sensor as practical.
Defocus the light received by using sensor optics.
Move the laser over a larger part of the target surface and take an average of the readings over time.
Use a larger laser beam or a diverging beam to create a larger diameter spot at the target.
Use a non-coherent light source, or if a coherent light source is used, place a device at the sensor (e.g. opalescent glass or other techniques known to those skilled in the art) or emitter can be used to de-cohere the beam.
Modulate the frequency of the laser to reduce its coherence.
Use as large a collecting lens at the receiver as possible or practical.

As will be appreciated methods and mechanisms to automatically re-align the light source on the photo detector can also be used to reduce the variation in received power due to unwanted beam movement.

Another method to increase the stability of the fractional light loss measurement is to re-set a 100% transmission reference level from time to time. This is preferably done whenever the scattering signal is below a threshold scattering level. Once the scattering signal is above some the threshold value the last calibration level is held and used for subsequent processing. However, as will be appreciated if a scattering level continues for an extended period of time the confidence in the reading will diminish as the time since last calibration will become long.

To combat the affect of a gradual drift of the computed fractional light loss to scattering ratio during a prolonged low level scattering event, a gradual reduction in the applied correction factor can be implemented.

As will be noted from the above, in order to be successful the system will typically require a precise and quickly adjustable laser steering to ensure that fractional light loss measurements are not compromised by minute changes in the laser/target alignment. A suitable beam steering mechanism is described above.

As noted above it is possible to implement embodiments of the present invention that that determine scattering ratios at multiple wavelengths. In this embodiment several light sources may be needed. These would preferably include one infra-red light source, and one shorter wavelength light source (e.g. blue/violet or UV) to distinguish particle sizes. This introduces the need for blue/violet or ultra-violet lasers that are currently still high cost, and typically have short-life expectancy and poor temperature tolerance.

This approach will typically require selective filters at the light sensor, to enable one camera to view two wavelengths, or require an extra camera/filter pair.

The background cancellation methods described in the previous embodiments include a process in which a number of emitter "on frames" and emitter "off frames" are summed or averaged. These methods typically use an equal number of ON and OFF frames.

However, if the background light level is increasing or decreasing during the period the frames are taken, there will be a residual component background component present since the ON and OFF frames were not taken simultaneously.

This effect can be minimised by changing the sampling scheme such that the "centre of gravity" of the ON samples and OFF samples coincide. This can be achieved by taking more OFF frames than ON frames (or vice versa), and interleaving them or using some other arrangement in which the "on" an "off" frames used are spread about the came central time.

Figure 31:
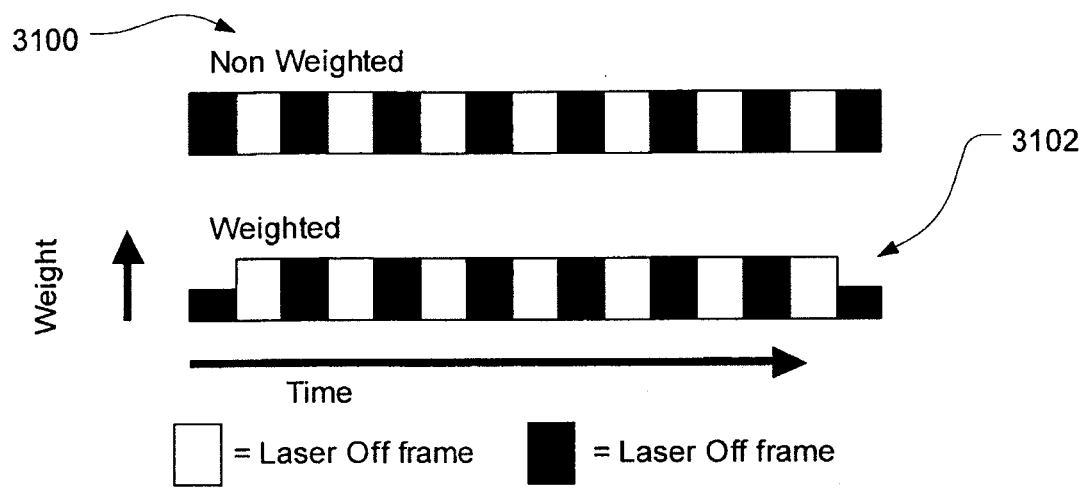
FIG. 31 illustrates a series of frames of an image sequence, which may be used in a background cancellation method according to an embodiment of the present invention.

FIG. 31 illustrates a series of frames of an image sequence 3100. Those frames coloured black represent "off" frames, i.e. those frames taken when the light source is turned off, and the frames shaded white are "on" frames" that are captured when the light source is illuminated. The sequence 3100 includes one more "off" frame than "on" frames. Meaning that the central time of the series of "on" frames is the same as that for the series of "off" frames.

In an alternative scheme weightings can also be applied to the frames. For example, FIG. 31 illustrates a second series of image frames 3102. In this series, the first and last frame "off" frames can are weighted by a factor of one half when used in the averaging or summing. This allows the background-cancelled image to be calculated as the sum of the ON frames minus the sum of the OFF frames, and avoiding the computational overhead of correcting for different numbers of frames.

Provided that the temporal centre of the ON exposures and OFF exposures coincide, then exact cancellation can be achieved for backgrounds light levels that are changing linearly with time.

Figure 32:
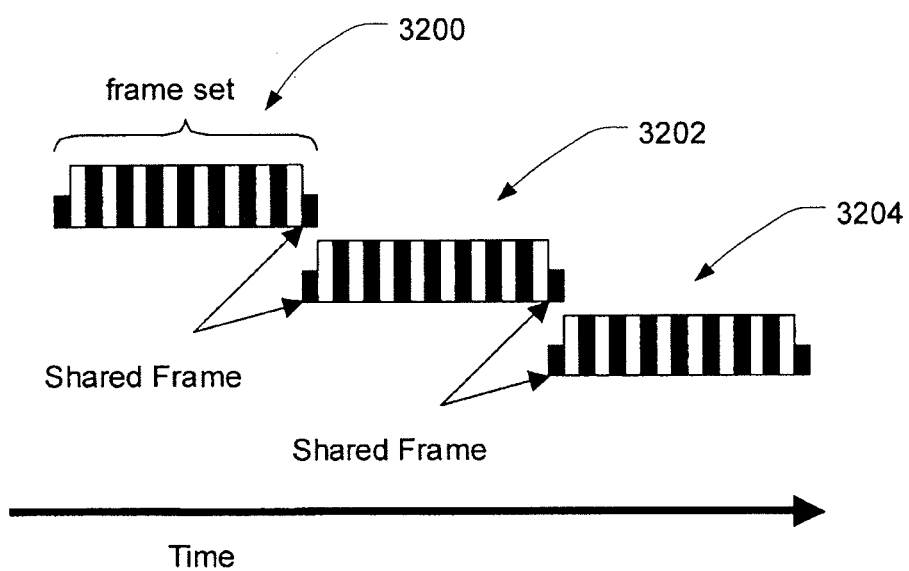
FIG. 32 illustrates a three sequentially acquired frames of an image sequence, which may be used in a background cancellation method according to an embodiment of the present invention.

In another variation, illustrated in FIG. 32, successive sequences of frames share (one or more frames) at their boundary. In this regard FIG. 32 shows three consecutively captured sequences of frames 3200, 3202 and 3204. In this scheme the "off" frame at the boundary between adjacent frame sequences, 3200 and 3202; and 3202 and 3204 contributes to the averages or sums of "off frames" for each sequence as described above. As well as assisting in performing better background cancellation in situations with linearly increasing or decreasing background levels it also avoids the need to discard otherwise usable frames.

Clearly this technique may be combined with any of the other described methods for performing background cancellation described herein or in our other copending patent applications.

Several embodiments of the above mentioned aspects of the present invention call for a scannable or steerable light source or optical components. For example, steerable laser beams are used in embodiments of the invention to address the following problems:

Commissioning the system requires the laser beam to be accurately set before the system is operational.

Drift or movement in the mounting. In this regard continuous adjustment of the laser beam may be needed to precisely maintain the required path when there is drift. For example, drift may occur due to building movement, as often arises in buildings when temperature or humidity changes; or due to unwanted shifts in the mounting arrangement.

Intrusion of objects into the field of view of the sensor—some of the embodiments described herein for addressing this problem include temporarily or continuously changing the direction of the light beam.

A range of laser beam-steering mechanism are known, and are used in a variety of applications. Examples known to the inventors include mirror galvanometers, piezo-electric optics mounts and motorised kinematic mounts. However, particular constraints exist on a beam steering mechanism used in a particle detection system proposed herein. For example aspects of the present detection system may have the following requirements that should be met for optimal performance.

Range of movement: A large range of movement may be needed in embodiments where beam scanning is used as part of ordinary operation.

Precision of movement: Because a small amount of the total beam power is scattered or obscured from the light beam per meter in embodiments of the present invention, alignment of the systems are required to be highly precise.

Rate of movement: In some embodiments it may be necessary to compensate for vibrations or high speed movement in mountings of the system, therefore any beam steering mechanism used will need to be able to counter rapid variations in geometry.

Service life: Over the required service life of a particle detection system, which is expected to be ten years, a scan for the purposes of obstruction detection may occur at one minute intervals, totalling more than 5 million operations.

Power consumption: Low power consumption is desirable.

It is advantageous that these requirements are met with a solution that provide robustness, long service life, low maintenance requirements and a very low average power consumption, and that this is achieved at a low cost of manufacture.

Figure 33:
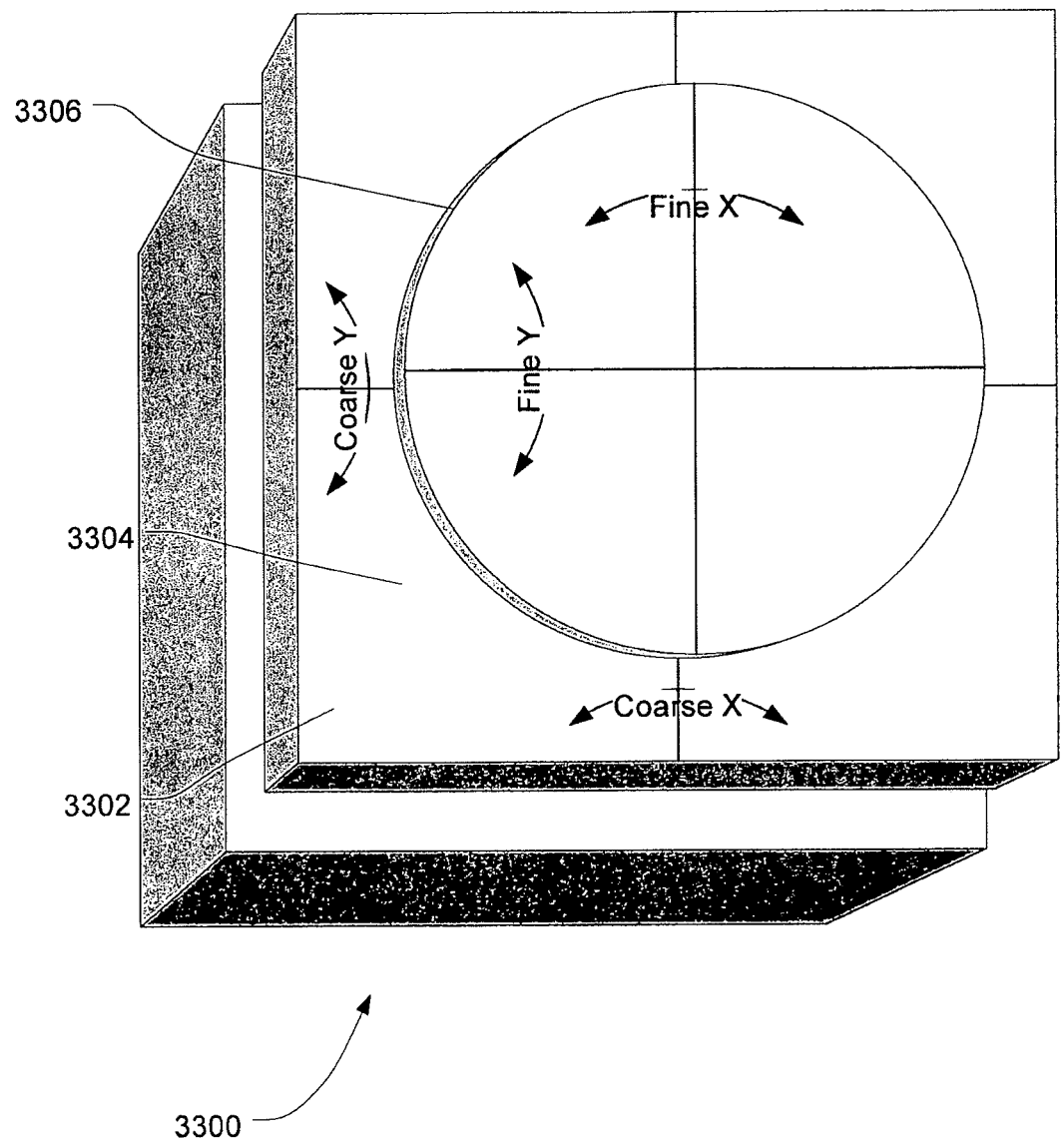
FIG. 33 illustrates a beam steering mechanism made in accordance with an embodiment of the present invention.

FIG. 33 illustrates schematically a first embodiment of the beam steering mechanism used in a preferred form of the present invention. In this case the mechanism operates by changing the direction of a mirror mounted on the mechanism, although other optical components could be mounted thereon. The beam steering mechanism 3300 is advantageously made up from 2 or more stages mounted on top of each other. The first stage 3304 is steerable relative the mounting 3302, and provides coarse control over a large range of movement which is particularly useful for initial coarse alignment of the particle detection system at installation. Preferably the first stage can provide more than 40 degrees travel with an accuracy of, say ±1 degree.

The second stage 3306, mounted on the first stage 3304 and independently steerable thereon, provides fine control over a narrower range of movement, which is useful for precise alignment during commissioning and for maintaining alignment in the event of drift. It may also permit repeated scanning of the laser beam for obstruction detection purposes without wearing out. Typically the second stage will provide a travel of less than 20 with accuracy of better than ±0.05 degrees.

For example, in the preferred embodiment, a first "coarse" stage 3304 can be mounted to the base mount 3302 and its directional control provided by using DC electric motors fitted with reduction gearboxes and a linkage mechanism, or cam, to a swash plate. Preferably, 2 motors are used, one controlling movement primarily in the X (horizontal) axis and one controlling movement primarily in the Y (vertical) axis.

This is, however, a matter of design convenience and it is not necessary that the axes chosen are orthogonal, provided a suitable range of movement in 2 dimensions can be achieved.

In the preferred embodiment a second "fine" stage 3306 is mounted on the first stage 3304 and provides relatively precise movement using 2 electro-magnetic voice-coil actuators. Well known alternative actuators, such as the piezo-electric type, may be substituted.

The benefits obtained by using this multi-stage approach are:

Lower cost—while it would be feasible to construct a movement system that combines both wide range of movement and precision, this would demand expensive components made to very fine tolerances. The multi-stage approach permits low-cost components to be used.

Long service life—the actuators chosen for the second stage, such as voice-coils or piezo electric devices, do not to wear out in the same manner as other available actuator mechanisms.

Figure 34:
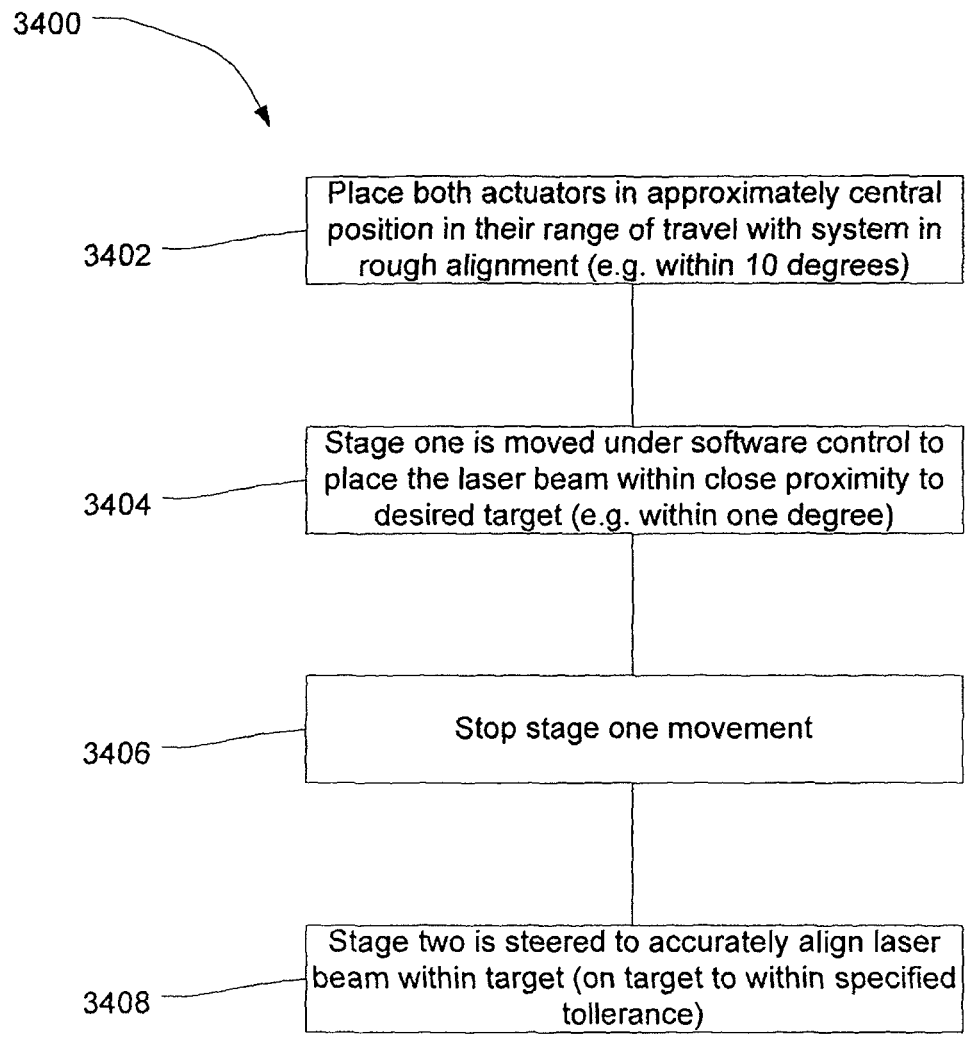
FIG. 34 is a flowchart illustrating steps in a target acquisition process implemented with a beam steering mechanism of the type illustrated in FIG. 33.

The steering mechanism just described can be used as follows for a target acquisition process used during commissioning of an AVSD system (or at other times, as illustrated in the flowchart of FIG. 34.

The target acquisition method 3400 begins (in step 3402) by the coarse positioning stage (and preferably also the fine positioning stage) being placed in its centralised position, which is preferably an un-powered rest position. The system is preferably then roughly aligned, say to within 10-20 degrees. This initial rough alignment will usually be performed manually by a technician, e.g. simply by relying on the installation measurements and relative pearliness of the walls to which the light source and target are mounted.

Next in step 3402 the coarse alignment stage is moved under software control to place the laser beam in rough proximity to the required target position, e.g. within 1 or 2 degrees.

Next in step 3404 the coarse alignment stage is then halted. Preferably, the coarse alignment stage is constructed so that when power is removed it remains securely at rest.

Then in step 3404 the fine alignment stage is moved to steer the laser beam into the required position.

The target acquisition algorithm used can be any of the acquisition algorithms described elsewhere in this document or any other mechanism known to those skilled in the art.

Further aspects of the present invention relate to mechanical improvements or modifications that can be used individually or in combination to improve either reliability or preciseness of an AVSD system as described herein.

A problem that may arise in an AVSD system is the contamination of the optically sensitive surfaces of the camera and laser by airborne particles. Such contamination may cause a reduction in the effective sensitivity and image resolution of the system. Whilst, the internal optical surfaces of the image capture device, light emitter or any intervening optical systems and may be sealed from the atmosphere to protect them, the outermost optical surfaces, e.g. lenses or windows are still prone to contamination.

One way to prevent particles from contacting an exposed optically sensitive surface is to place the optically sensitive surface at a significant distance from the aperture in the enclosure through which it receives or transmits light. The aperture permits the entry of light into the camera, or the exit of a beam from the laser, but creates a pocket of substantially still air between the optical surface and the environmental atmosphere. Any dirt particles which enter the aperture will then be likely to settle out on optically unimportant surfaces before they travel to the optically sensitive surface. Furthermore, small particles which may otherwise stay suspended in the air and so could reach the optically sensitive surface can be removed.

Figure 35:
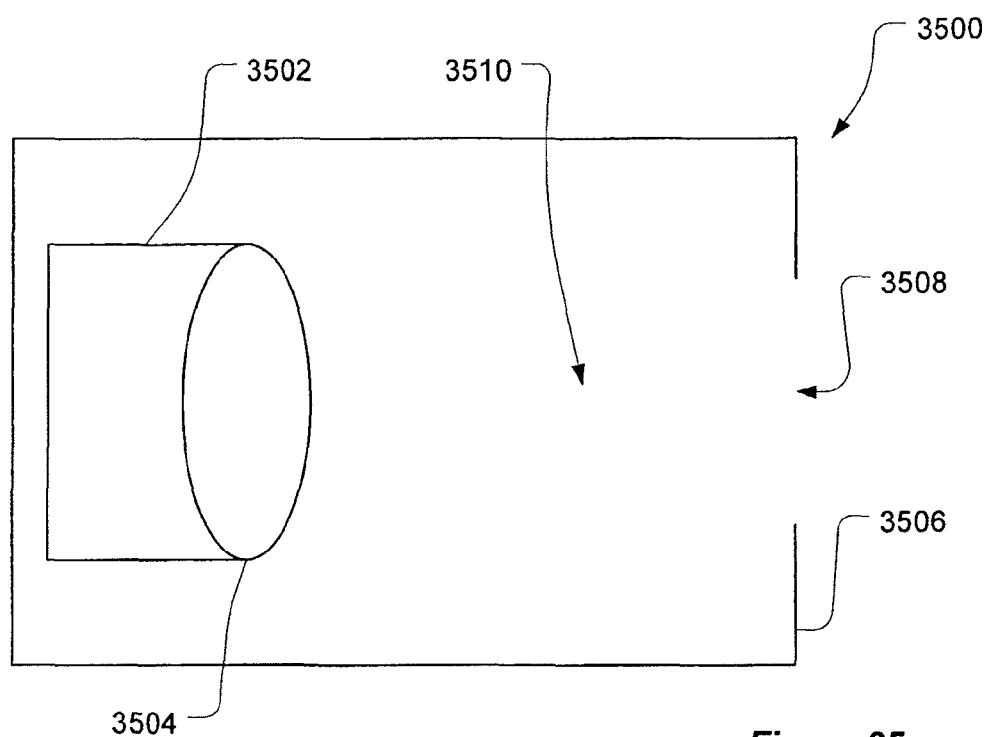
FIG. 35 illustrates a housing arrangement for an optical component of an AVSD system made according to an embodiment of the present invention.

FIG. 35 illustrates an optical arrangement 3500 of the type described above. The optical arrangement 3500 includes a component 3502 of the AVSD system (e.g. a light emitter such as a laser or light detector such as a camera) that includes an exposed optical element 3504, which may be a lens or window etc. Surrounding this component 3502 is a housing 3506 which includes an aperture 3508 through which light may enter or leave the housing. Between the aperture 3508 and the exposed optical component 3504 the housing encloses a volume 3510 in which relatively still air will be present.

One method for removing light particles suspended in the volume 3510 is to arrange for an electric field to be set up across the volume of air 3510, so drawing airborne particles from the air before they can travel to the optically sensitive surface.

Figure 36:
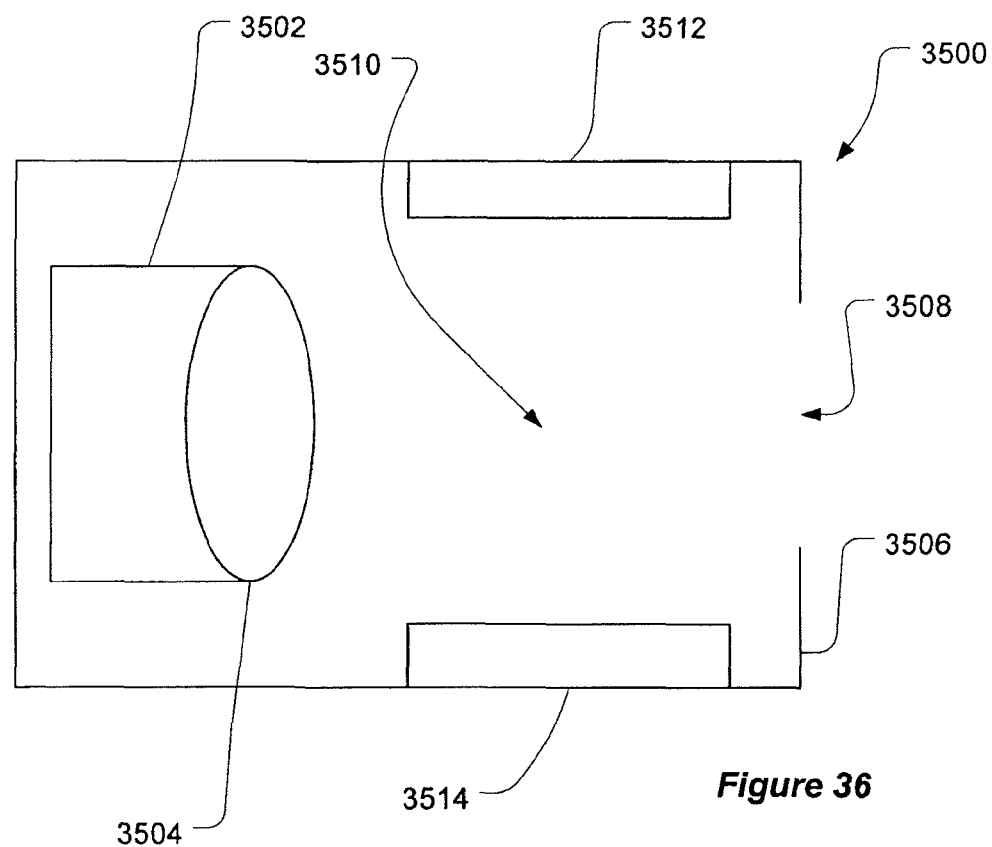
FIG. 36 illustrates a housing arrangement for an optical component of an AVSD system made according to a further embodiment of the present invention and which includes a passive electrical contaminant capturing means.

In the embodiment of FIG. 36 an electrical field is provided passively, by placing permanently electrically charged materials 3512 and 3514 adjacent to the air volume 3510. Such materials are well known and can include e.g. electret material such as that available from 3M or another polarised ferroelectric material. Preferably, the construction of the housing 3506 is such that it allows the materials 3512 and 3514 to be conveniently replaced or cleaned, should it become excessively contaminated.

Figure 37:
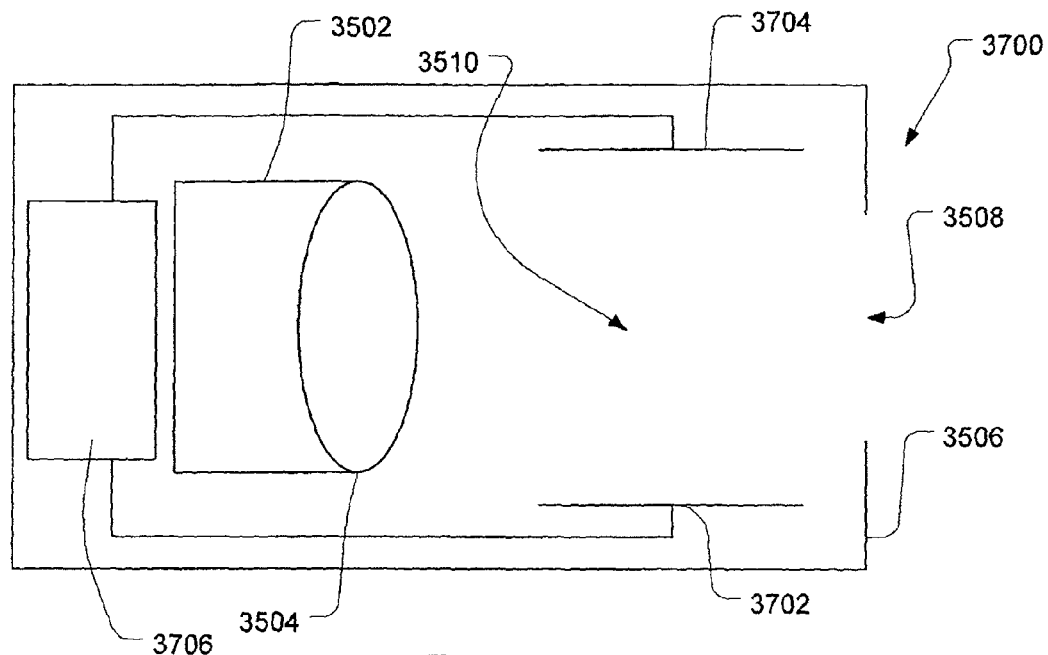
FIG. 37 illustrates a housing arrangement for an optical component of an AVSD system made according to another embodiment of the present invention, which includes an active electrical contaminant capturing means.

In another embodiment, such as that shown in FIG. 37, the electric field can be generated actively e.g. by any one of several well known electronic methods. In this embodiment 3700 the housing 3506 includes two charged plates 3702 and 3704 located either side of the volume 3510. An electric field between the plates 3702 and 3704 are maintained by circuit 3706. The circuit can be, for example, an inverter/capacitor-diode ladder arrangement also known as a Cockcroft-Walton voltage multiplier.

Figure 38:
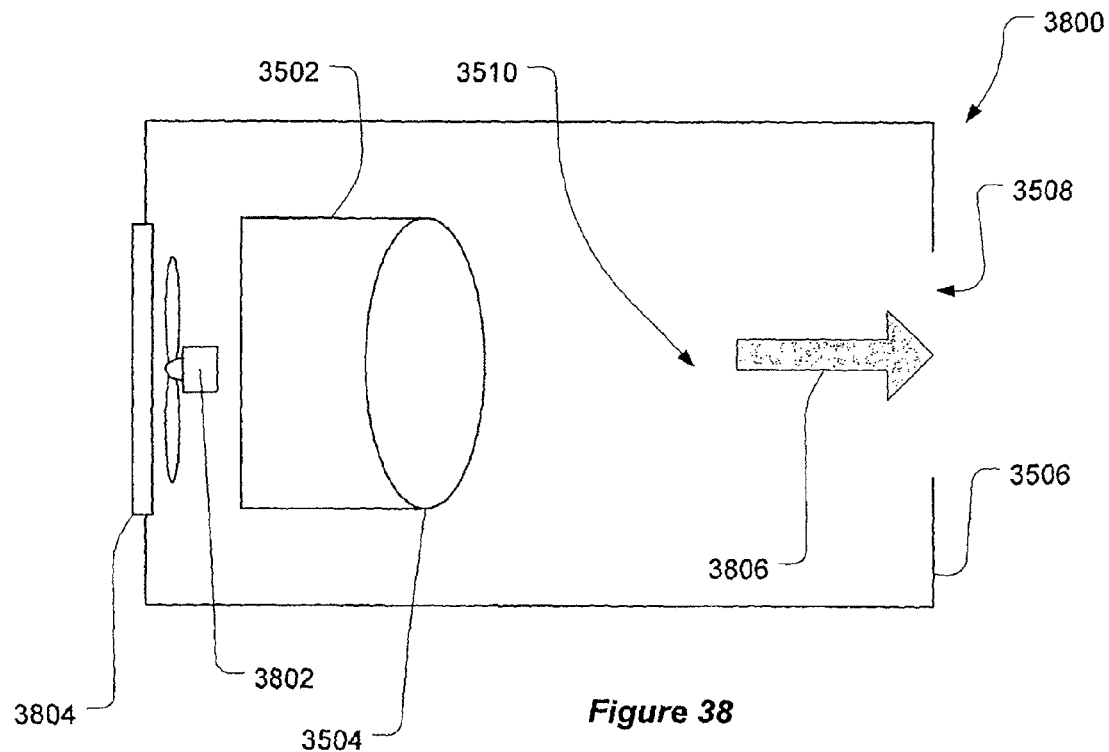
FIG. 38 illustrates a housing arrangement for an optical component of an AVSD system made according to an embodiment of the present invention, which includes a clean air optics cleaning system.

Another way to prevent the particles from travelling toward the optically sensitive surface is by inducing an opposing flow of clean air. This clean air may be provided by drawing outside air through a filter using a fan. FIG. 38 illustrates an example of such an arrangement. Generally speaking the housing 3506 and optical components 3502 are the same as that illustrated in FIG. 35 (and like components are like numbered). This arrangement 3800 additionally includes a fan 3802 mounted inside the housing 3506 which is arranged to draw air into the housing through the filter 3804. The clean air entering the housing in this manner is then forced around the optical components 3506 and exits the housing 3506 via the aperture 3508 in the direction of arrow 3806. This system can be enhanced by using a duct or other similar device to blow the clean air directly onto the exposed optically sensitive surface 3504 to ensure that it is kept free of contamination.

A related, but slightly different problem may arise due to living creatures, particularly insects or spiders, moving onto the exposed optical surfaces of the system, e.g. on the lens the sensor or the laser emitter. An insect, such as for example a large moth, could land on the sensor viewing window and obstruct an unacceptable portion of the view, or on a light source and could partly or fully obstruct the light beam emitted therefrom. Furthermore, spiders in particular may spin webs that can adhere to the optical surfaces and have a detrimental effect on performance of the system.

Similar problems have been addressed in the field of security cameras by the use of chemical repellents, insecticides and low-adhesion coatings, as well as wipers. These are of limited effectiveness and require regular renewal or maintenance.

An alternative protection method for the optics from encroachment by bugs or the like is to place an electrical conductor around the aperture in the housing or perimeter of the exposed optical component. This conductor can then be provided with a high-voltage power supply to electrocute any insect before it encroaches on the optics. To prevent potential for human injury, the current can be limited to non-harmful levels and operated with a safety interlock on the housing that turns off the high voltage supply if the hosing is opened.

In some implementations of the present invention it may tolerable to have a partial or full obstruction of one or more of the optical elements of the system for a short period of time. For example, if an obstruction clears in a time which is less than a predetermined threshold period, for example 30 seconds, then this may be considered acceptable and result in no action being required. However, if it continues for longer than the threshold period then a fault may be detected using one or more of the methods described elsewhere herein.

Surveillance cameras are known which employ a variety of methods to clearing and keeping viewing windows clean. One example is the use of wipers. However, wipers have the disadvantage that they may require frequent maintenance and require a consumable solvent to prevent damage to optical surfaces that will be caused by dry-wiping.

The inventors have determined that this problem can be ameliorated by the use of a scratch-resistant window, e.g. a sapphire window. However other approaches to addressing this problem have also been proposed.

Another example of a prior art solution is described in international patent publication WO05096091A1, titled, Cameras And Methods Of Cleaning Cameras. This provides for a transparent cover which may be driven so as to throw off extraneous matter, or at least rotated to provide a clearer view. Similar techniques have been used in other similar situations, for example spinning transparent disks are often provided in viewing windows on a ship's bridge to throw off spray.

In the present embodiment of the invention an optical element's light path, or view, is directed through at least a part of the envelope swept out by at least one moving member. This moving member prevents settling of an insect or other extraneous material on the optical surfaces.

Figure 39:
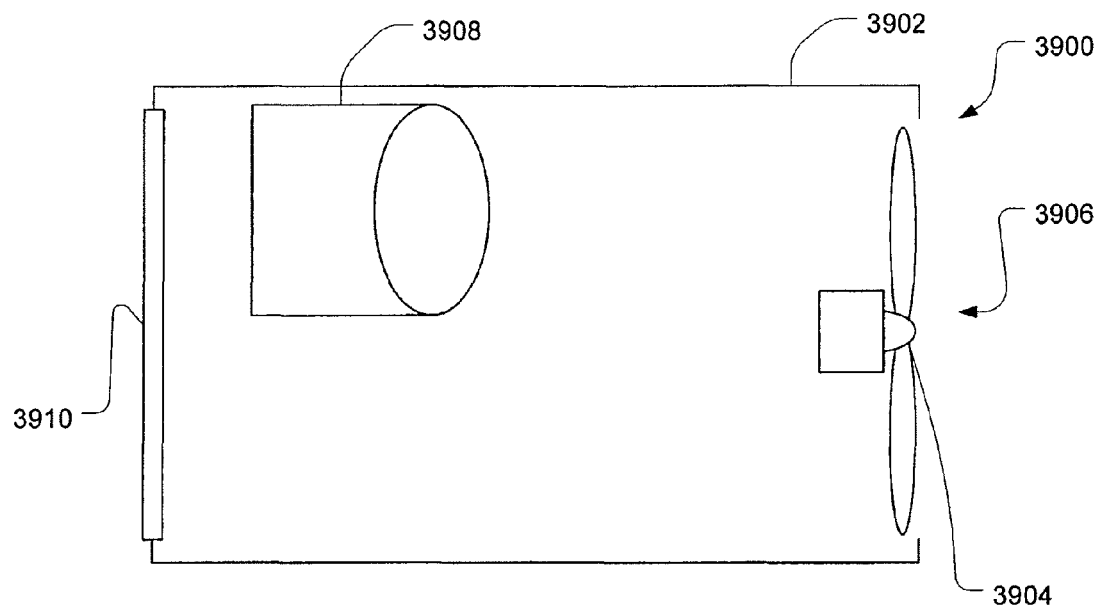
FIG. 39 illustrates a housing arrangement for an optical component of an AVSD system of an embodiment of the present invention, which includes a mechanical element for preventing or clearing obstructions from the field of view of the optical component.
Figure 40:
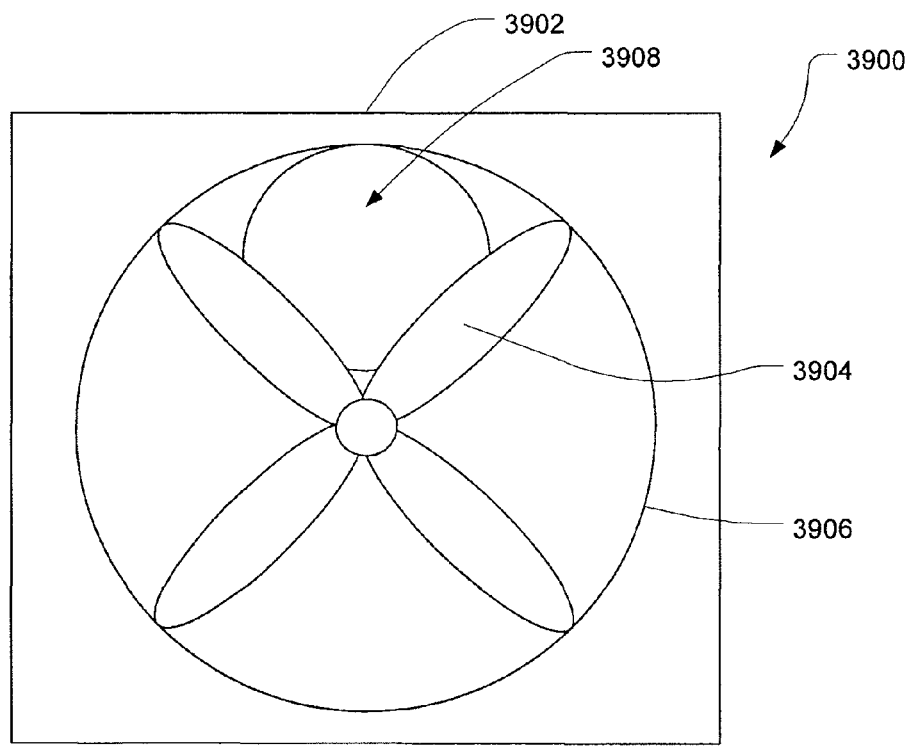
FIG. 40 illustrates a front view of the housing arrangement of FIG. 39.

Referring to FIG. 39 which illustrates an embodiment of a housing adapted to hold a camera. The housing arrangement 3900 is generally similar to that shown in FIGS. 35 through 39 and accordingly elements that share the same function have been given the same reference numbers as in the previous embodiments. The system of FIG. 39 differs from the previous embodiments in that the housing 3902 is provided with a moving member in the form of a multi-bladed axial fan 3904 which is electrically driven. Fan is sized and positioned so that its blades largely fill the viewing aperture 3906 in the housing 3902 through which the camera 3504 captures light. In use the camera 3908 captures its images by looking through the blades of the spinning fan.

The camera's 3908 open aperture time and the fan are preferably synchronised by software such that the camera 3908 captures each frame while the lens view is not obstructed by a fan blade. To assist in this the fan motor is preferably of the DC brushless type and is equipped with a commutation output signal. Alternatively any one of many well known methods may be used to control or determine the speed and angular phase of the motor.

In other embodiments any camera frames found to be obstructed by a fan blade can simply be discarded.

Advantageously the fan can be is arranged to draw air out of the housing 3902 in a manner consistent with the above described methods, thus inhibiting the entry of airborne dust etc. into the enclosure. To aid in this task the housing can be fitted with a filter 3910 to allow clean air to replace the air drawn out of the housing 3902 by the fan 3904.

The fan 3904 may be run continually, or preferably to extend its life is operated only when an obstruction has already been detected. It may also be operated at intervals to test and maintain serviceability.

The aperture 3906 may advantageously be partly obstructed, except in the region of the camera view, to limit air-flow rate.

In an alternative embodiment, the moving member may be a wiper, a brush, a simple rod, or the like and may perform a reciprocating movement across the viewing hole to protect the optics from entry of insects, spider or other extraneous matter. To obviate the problem of accumulating spider-web in particular, in one embodiment the moving member may be caused to fully or partly rotate as it is moved across the hole, thus collecting the threads in a bobbin-like fashion.

Persons skilled in the art will appreciate that this aspect of the invention can be additionally applied to protecting a light source e.g. laser, as well as to a camera.

Where the AVSD system is to be operated in low-light conditions, or where the system is subjected to high temperatures, it is advantageous to reduce the temperature of the image sensing device or light source, thus increasing its reliability and reducing measurement noise. In a typical implementation of this a cooling device such as a Peltier cooler is placed in close physical contact with the light sensor with heat energy being drawn away to an area for dissipation to the external environment.

Figure 41:
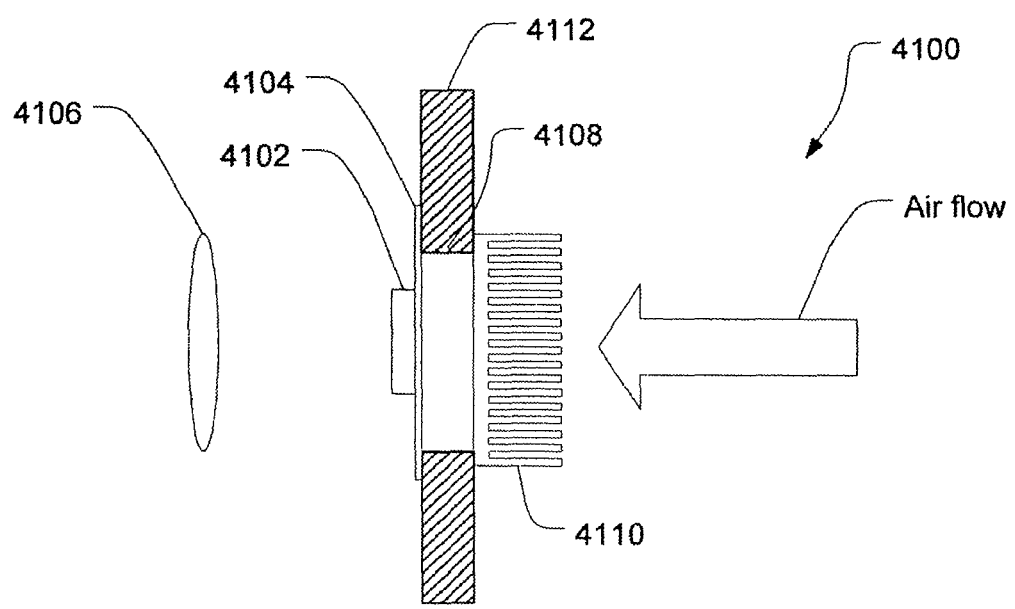
FIG. 41 illustrates a cooling arrangement for an optical component of an AVSD system of an embodiment of the present invention.

FIG. 41 illustrates an image capturing arrangement made in accordance with an embodiment of this aspect of the present invention. The image capture arrangement 4100 includes an image capturing element 4102 e.g. a CCD or CMOS image capture chip mounted on a circuit board 4104. The image capturing element 4102 is configured to view the light source in the region of interest through imaging optics such as a lens 4106. Mounted to the opposite side of the circuit board 4104 to the imager capturing device 4102 is a Peltier cooling device 4108, which in turn is coupled to a heat sink 4110. The Peltier cooler 4108 transfers heat from the image capturing device 4102 to the heat sink 4110, where it is transferred to atmosphere. To prevent the heat dissipated from the heat sink 4110 from heating up the image capturing device 4102 thermal insulation 4112 is provided. In order to increase the efficiency of heat dissipation of the heat sink the system can incorporate a fan to force air circulation around the heat sink 4110. In alternative embodiments a heat pipe could be used to allow the heat sink to be placed further away from the image capture device 4102 to further aid heat dissipation.

The previously described AVSD systems have used one or more stationary beams that illuminate fixed linear regions of interest across a volume being monitored.

Whilst these stationary beams placed at intervals across a protected space enable smoke detection to be performed in a manner that conforms with regulatory requirements and is satisfactory in many applications, a narrow plume of smoke, especially from a concentrated hot fire, could by chance pass between beams without being detected.

To address this possibility, embodiments of the present invention could provide an effectively uninterrupted plane or planes of laser light directed across the space that can be monitored. This plane of light may be generated either by an optical system such as a cylindrical lens or by scanning one or more beams across the volume.

Figure 42:
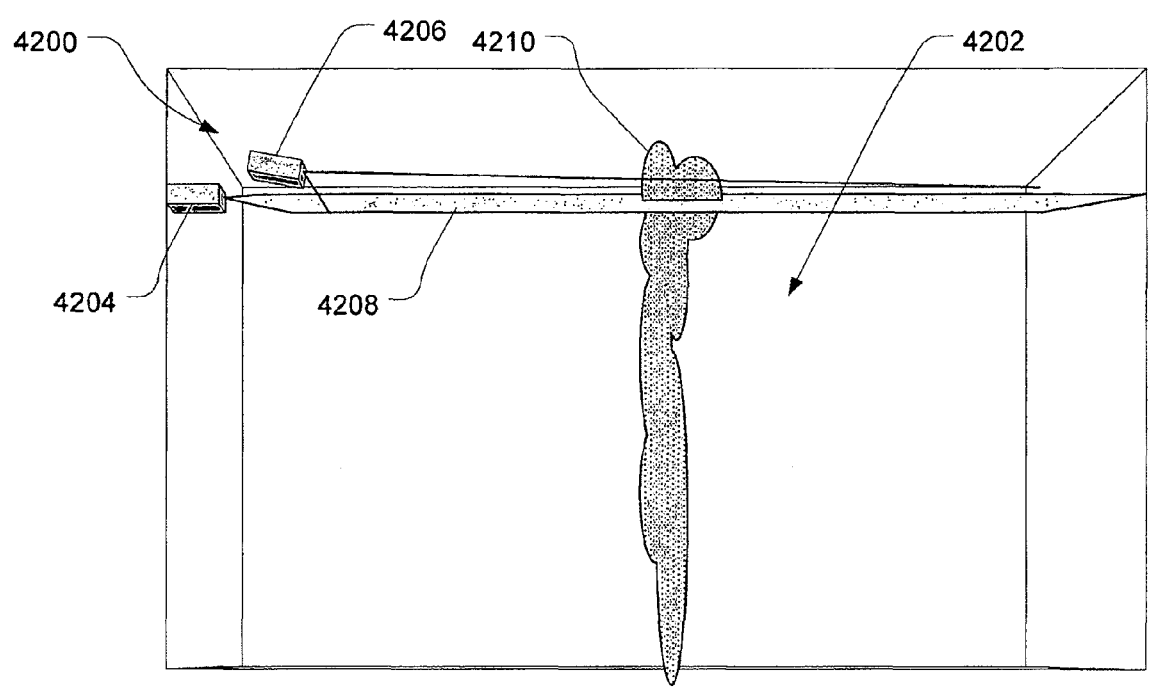
FIG. 42 illustrates a volume monitored by an AVSD system according to an embodiment of the present invention in which a plane of light is projected across the volume.

FIG. 42 illustrates an exemplary AVSD system of this type. The system 4200 is configured to monitor a room 4202 and includes a light source 4204 and an image capture means in the form of a camera 4206. The light source 4204 is illuminates a plane 4208 which is largely within the field of view of the camera 4206. As indicated above the light source 4204 can illuminate a plane either by scanning a linear beam from side to side or by using optical focussing arrangements such as a cylindrical lens.

With such an arrangement a narrow plume of smoke 4210 will cause scattering as soon as it reaches the height of the light plane 4208 and cannot pass through the plane 4208 without causing scattering.

It is to be expected that the measurement sensitivity achievable at points across the plane will vary according to the angle of scattering, and this may be automatically compensated for in software; however the smoke plume will thus be detected in the shortest possible time.

Figure 43:
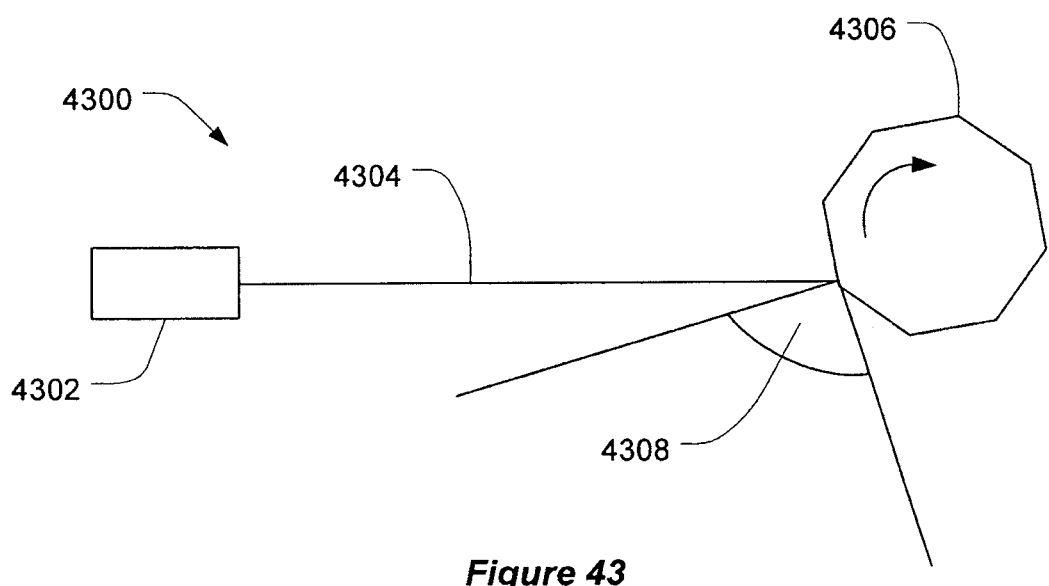
FIG. 43 illustrates a mechanism for scanning a light beam across a volume that is suitable for use in the embodiment of FIG. 42.

One mechanism for implementing beam scanning is to use a rotating octagonal mirror. FIG. 43 illustrates an arrangement for beam scanning 4302, including a light source 4302 that emits a beam of light 4304. The beam 4304 is reflected off a rotating octagonal mirror 4306. As the mirror 4306 rotates the angle of incidence of the beam arriving at the mirror surface changes and the reflected beam sweeps out sector 4308.

As noted above by scanning the beam the system has the advantage of continually monitoring a larger area than a stationary beam, while allowing the use of simple and reliable mechanisms for beam scanning.

Since the laser is moving, the beam position in the camera's image will move. If the camera is in the same plane as the laser then the beam will be constrained to an epipolar line in the image, but the positional information will still be blurred because of the time varying geometry. To combat this problem the laser sweep is intentionally de-synchronized from the camera frame rate so that it sweeps out a set of different sub-area in each successive exposure period. After a time the cycle can repeat. The positional information can then be recovered from a set of such images by solving a set of simultaneous equations. The usual AVSD methods to obtain grey levels per pixel along the beam in the image are applied before attempting to de-convolve the blurring effect of the moving laser beam.

If the beam scan rate is sufficiently slow, then the blurring effect can be ignored.

The correct phase of the laser sweep vs. the camera shutter can be checked since a part of the sweep of the laser beam can be through the camera lens. Most of the time the laser can be blanked as it passes over the lens, and when a check is needed it can be left on. Laser Tilt adjustment can also be checked for in the same way (picturing the scanning to be occurring in the horizontal plane).

Camera field of view supervision based on edge scattering as described above can also be performed with this physical arrangement.

Figure 45:
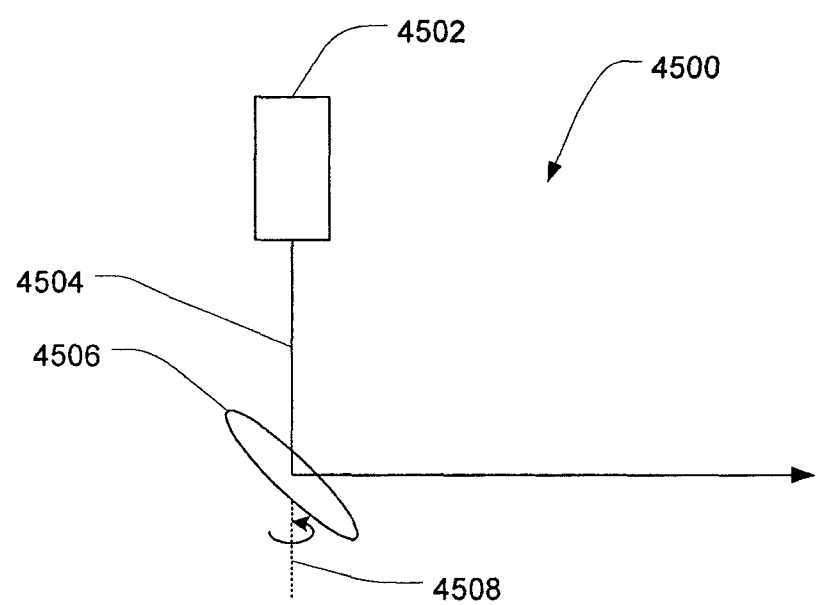
FIG. 45 illustrates a mechanism for scanning a light beam to create a light curtain.

In another embodiment a light curtain can be created by scanning a beam using a rotating mirror placed at an angle to the beam. Preferably the mirror is set at 45 degrees to the direction of incidence of the beam and rotated about an axis parallel to the beam. A suitable arrangement 4500 is shown in FIG. 45. In this arrangement the light source 4502 emits a beam of light 4504 toward a mirror 4506. The mirror 4506 is set at an angle of 45 degrees to the incident beam 4504 and reflects light at right angles to the direction of emission of the beam 4504 from the light source. The mirror 4506 is rotatable about an axis 4508 to cause the beam 4504 to sweep out a plane perpendicular to the incident beam 4504. The shape of the curtain of light swept out by the beam can be changed by changing the angle of incidence of the beam 4504 onto the mirror 4506. In other embodiments it is possible to additionally rotate the mirror around an axis perpendicular to the axis 4508. In this embodiment the beam can be made to sweep out a 3 dimensional volume. In this example the mirror can be mounted in a gimballed type arrangement that allows movement about multiple axes.

In bright lighting conditions measures must be taken to avoid saturation in the captured images, such measures include, the use of small apertures (high F numbers), lossy filters (usually neutral density) and short shutter times. Unfortunately, these measures reduce the system sensitivity directly in proportion to the loss factor that is introduced.

An alternative is to take advantage of the higher frame rate that short shutter times allow. By using the short shutter times more images can be captured in a given period, thus reducing the noise.

In principle, if the shutter time must be reduced by a factor of N to avoid saturation, then the frame rate may by increased by N times. Therefore the integration lengths may be increased by the factor N. Assuming that the camera noise (in terms of pixel values) is unchanged, the extra averaging reduces the system noise by the factor $\sqrt{N}$, while the gain change worsens by N times. The net result is then a noise level that is $\sqrt{N}$ times worse, but this is much better than being N times worse as would be the case without the frame rate increase.

Therefore, by using this scheme there is no need to suffer the full sensitivity penalty that neutral density filters or large F-stops cause.

An important additional benefit of the high frame rate is that there is reduced sensitivity to rapid background lighting variations.

In a typical implementation using an F1.6 lens and a narrow band interference filter (50 nm) can be used to reduce unwanted light and a conventional CMOS image sensor, an exposure exceeding 2 ms may cause saturation in environments with large amounts of sunlight. Therefore, for example, an exposure time of 2 ms can be used, and this allows a frame rate of about 600 frames per second. Compared to operating the system at a more conventional rate of 25 fps, this would give a noise reduction and consequent sensitivity improvement of approximately a factor of 5.

Current technology, low cost 640×480 CMOS image sensors are not generally capable of 600 fps, a maximum rate of 60 fps being more common. A method to allow operation at the high rate is to:

Program the sensor active window to a narrow horizontal window eg. 48 pixels high×640 pixels wide.

Only extract the potion of the image from the sensor, and then reset the sensor immediately for the next frame Ensure that the image of the projected laser beam appears within the window.

In practice the correct orientation can be achieved with a horizontal mounting orientation for the camera, and with the camera, laser and laser beam all within an approximately horizontal plane.

In this example the vertical height is one tenth of the full imager resolution, allowing up to a 10 times increase in frame rate.

When high levels of particulate matter are present in a volume being monitored by an AVSD system this will cause high obscuration of the light beam projected by the AVSD primary light source. In such conditions light scattered from the particles is itself scattered and absorbed significantly. This can lead to error in the measurement of the smoke level. With very high levels of smoke the detectable light scattered in a forward direction from the primary illumination source may be reduced in intensity to a very low level or even not visible in the acquired images.

In particular, scenarios with very rapid rises in smoke density might appear as a fault condition if scattering based detection alone is employed. Additionally, high levels of smoke might be difficult to distinguish from low levels due as little light is received at the sensor detecting scattered light.

Figure 44:
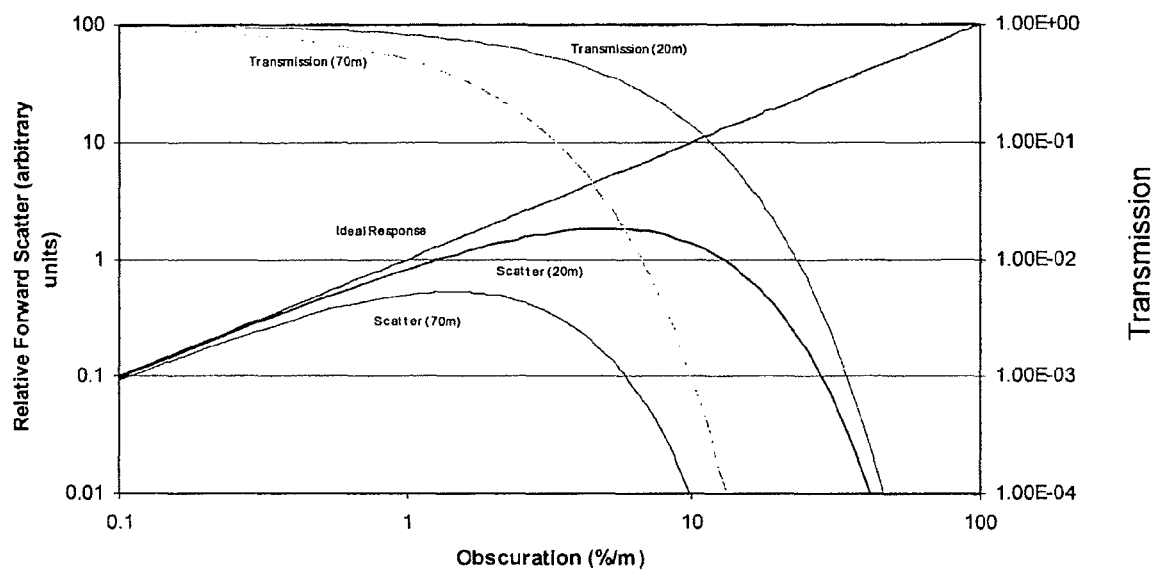
FIG. 44 is a graph illustrating the relationship between the levels of forward scatter for different smoke levels (obscurations) over different path lengths.

The effect of rising smoke levels on the received scatter signal is shown in the graph of FIG. 44. The graph points are calculated on the basis of homogenous particle density in the volume of interest and with isotropically scattering, non-absorbing particles. The graph is plotted over two path lengths, 20 meters and 70 meters. As can be seen from the graph, at low levels, e.g. up to an obscuration level of about 1% per meter, the scatter signal follows the ideal response relatively well and increases in proportion to the obscuration. At higher obscurations the scatter signal plateaus at a turnover point, and finally turns down.

The fact that the graph is not monotonically increasing causes an ambiguity as any detected scattering level generally corresponds to two different obscurations (i.e. two different levels of particle concentration). Accordingly it is necessary to solve or avoid this ambiguity in order to correctly determine the particle concentration.

One method for avoiding the ambiguity is to use alarm thresholds that are sufficiently below the turnover point in the graph that an alarm will be issued before the smoke reaches the turnover point.

To reduce the error in scattering readings, the total fractional light loss along the beam length can be estimated from the average smoke level along the beam. This can then be used to scale up the scattering readings, since the path length for the photons is about the same whether they are scattered near the camera or near the laser or in between. These new scattering readings can then be fed back to improve the estimate of the total fractional light loss and the process repeated until the desired scattering accuracy is attained. However, it is important to check for convergence failure.

If convergence failure occurs, a suitably large smoke level can be output in place of the non-convergent value, such that all down stream decision systems to go into alarm.

A more sophisticated method is to model the path in small segments, using estimated fractional light loss for each segment based on the scattered light received for that segment. These values allow a better estimate of the total fractional light loss to be gained. Again iteration is necessary. Such 'finite element' methods are should be known to those skilled in the art.

Alternatively an additional detector, capable of measurements at high smoke levels can be added to the system.

The preferred method of correcting for the attenuation of the scattered light signal is to use the arrival intensity of the laser beam (which is equivalent to the fractional light loss) at the end of its path to determine an appropriate correction factor. This correction is most conveniently based on the primary AVSD laser. If one or more of the supervision techniques or targeting techniques described herein are employed any additional components required to implement such a method are likely to be present in the AVSD system. Alternatively the following arrangements could be used:
- a separate backscatter laser can be used, and monitored by the same camera as the primary forward scatter system;
- another entire AVSD system adapted for operation at high smoke densities could be implemented;
- a photo-detector monitoring the laser target to measure the arrival intensity of the laser beam, e.g. as described in other aspects of the invention;
- an arrangement with a reflective surface at the target to reflect some or all of the laser beam back towards a photo-detector at the light source which determines the arrival intensity of the laser beam after traversing the volume twice. The reflector can be non-specular or specular, or a retro-reflector, as described above. Such as system has an advantage of increased sensitivity because the light travels through the volume twice.
- use the intensity of another light source as measured by the camera. For instance the laser unit may already be fitted with marker lamps to allow accurate determination of the position of the light source point in the image. Similar markers can be placed on other system components and monitored across the volume.
- analyse the spatial frequency of reference areas within the images obtained from the camera. Significant reduction in the high frequency components indicate a large concentration of smoke, for example, marker lamps at the laser end that would normally only occupy a few pixels in the sensor's field of view will blur over a larger region in the presence of a large concentration of smoke, thus reducing the number of short period (high frequency) components in the image.
- any method for measuring transmission, obscuration or any other parameter related to particle concentration.

At very high levels of obscuration where there is a risk that the scattering derived smoke levels are unreliable, the measured the arrival intensity of the laser beam may be combined with the scattering levels to more reliably detect particles.

A simple method is to divide the scattering derived smoke levels by the arrival intensity of the laser beam (transmission), where transmission=1−total intensity loss over the path. In an alternative method the system can be adapted to weight measurements between a scattering derived smoke signal and a smoke signal derived primarily from the arrival intensity of the laser beam. The bias between these different detection methods can be determined dynamically. For examine at low particle levels the system can be arranged to only use scattering derived smoke levels, however as the arrival intensity of the laser beam decreases more bias can be made toward a smoke level determined from the arrival intensity measurements. The system could be set up to scale the relative contribution of the two smoke measures between two thresholds. For example, at a level where the arrival intensity of the laser beam has diminished by less than 40% from its expected intensity scattering derived smoke levels only can be used. If the arrival intensity of the laser beam is has diminished by more than 60% from the expected intensity a measure of smoke determined from the received intensity measurement (possibly allocated to sectors by length) can be used. For arrival intensities in between the thresholds a weighted mean of the two can provide a smooth transition.

An alternative method for allocating the intensity loss over the length of the beam to spatial sectors along the beam is to weight the allocation on the basis of the scattering signal, if it is sufficiently above the system noise level. In this way the ability of the AVSD system to determine the location of the smoke is not lost at high smoke levels.

It will be understood that the invention disclosed and defined in this specification extends to all alternative combinations of two or more of the individual features mentioned or evident from the text or drawings. All of these different combinations constitute various alternative aspects of the invention.

It will also be understood that the term "comprises" (or its grammatical variants) as used in this specification is equivalent to the term "includes" and should not be taken as excluding the presence of other elements or features.

The invention claimed is:

1. A method in an active video smoke detection (AVSD) system, the AVSD system including:
   - at least one primary light source configured to emit a beam of light across a volume being monitored;
   - an image sensor having a field of view and arranged to capture images of a least part of the beam of light; and
   - means to analyze images captured by the image sensor to detect the presence of particles within the volume on the basis of light scattered from the beam and captured in the images; said method comprising:
   - emitting the beam of light across the volume being monitored at a primary beam position to enable detection of particles within the volume based on the analysis of images captured by the image sensor on the basis of light scattered from the beam at the primary beam position and captured in the images; and determining an intrusion of an object into the field of view of the image sensor such that the object impedes the image sensor's view of the beam in the primary beam position when detecting particles, by (a) scanning a beam of light across a part of the volume being monitored to illuminate a region within the volume that lies between a primary beam position and the image capture means, and (b) analyzing the output of the image sensor to determine whether an object has impinged upon the beam of light emitted in step (a), to identify an object that blocks a line of sight between the image capture means and the beam of light when it is in its primary beam position.

2. A method as claimed in claim 1, wherein the step of analyzing the output of the image sensor, includes identifying the presence of any one of the following features in the sensor output: reflection, refraction, diffraction pattern or glint.

3. A method as claimed in claim 1, wherein step (a) is performed using a primary light source of the AVSD system.

4. A method as claimed in claim 1, wherein the AVSD system includes at least one secondary light source that is not used for particle detection and step (a) is performed with the said secondary light source.

5. A method as claimed in claim 1, wherein the AVSD system includes at least one secondary light source for monitoring a portion of the field of view of the image sensor that is affected by a primary light source; and the method includes:
analysing the output of the image sensor to determining an intrusion of an object between the secondary light source and the image sensor.

6. A method as claimed in claim 5, wherein the secondary light source covers an extended area of the field of view of the image sensor.

7. A method as claimed in claim 1, which further includes:
indicating a fault in the event that it is determined in step (b) that an object has impinged upon the beam of light.

8. An active video smoke detection system (AVSD) including:
at least one primary light source configured to emit a beam of light across a volume being monitored, wherein the at least one primary light source is arranged to emit a beam of light across a volume being monitored at a primary beam position to enable detection of particles within the volume;
an image sensor having a field of view and arranged to capture images of a least part of the beam of light;
means to scan a beam of light across part of the volume being monitored configured to cause the scanned beam to illuminate a region within the volume that lies between a primary beam position and the image capture means; and
means to analyse images captured by the image sensor to detect the presence of particles within the volume on the basis of light scattered from the beam and captured in the images;
said AVSD system being configured to perform a method as claimed in claim 1.

9. An AVSD system as claimed in claim 8, which includes at least one secondary light source.

10. An AVSD system as claimed in claim 9, wherein the secondary light source is arranged to emit a beam of light across at least part of the field of view of the image sensor includes illuminating a background behind the volume being monitored; and wherein means to analyse images is configured to identify the presence of a shadow in the sensor output.

11. An AVSD system as claimed in claim 10, wherein the secondary light source projects a pattern of light onto a background surface.

12. An AVSD system as claimed in claim 9, wherein the at least one secondary light source is arranged in a portion of the field of view of the image sensor that is affected by a primary light source and emits light that is received by the image sensor;
wherein the means to analyse images is arranged to detect an obscuration of the secondary light source to determine an intrusion of an object between the secondary light source and the image sensor.

13. An AVSD system as claimed in claim 12, wherein the secondary light source covers an extended area of the field of view of the image sensor.

14. An AVSD system as claimed in claim 8, wherein the scanned beam is emitted by the primary light source.

15. An AVSD system as claimed in claim 8, wherein the scanned beam is emitted by the secondary light source.

16. A method as claimed in any one of claim 2, wherein step (a) is performed using a primary light source of the AVSD system.

17. A method as claimed in claim 2, wherein the AVSD system includes at least one secondary light source that is not used for particle detection and step (a) is performed with the said secondary light source.

18. A method as claimed in claim 2, wherein the AVSD system includes at least one secondary light source for monitoring a portion of the field of view of the image sensor that is affected by a primary light source; and the method includes:
analysing the output of the image sensor to determining an intrusion of an object between the secondary light source and the image sensor.

19. A method as claimed in claim 3, wherein the AVSD system includes at least one secondary light source for monitoring a portion of the field of view of the image sensor that is affected by a primary light source; and the method includes:
analysing the output of the image sensor to determining an intrusion of an object between the secondary light source and the image sensor.

20. A method as claimed in claim 4, wherein the AVSD system includes at least one secondary light source for monitoring a portion of the field of view of the image sensor that is affected by a primary light source; and the method includes:
analysing the output of the image sensor to determining an intrusion of an object between the secondary light source and the image sensor.

21. A method as claimed in claim 2, which further includes:
indicating a fault in the event that it is determined in step (b) that an object has impinged upon the beam of light.

22. A method as claimed in claim 3, which further includes:
indicating a fault in the event that it is determined in step (b) that an object has impinged upon the beam of light.

23. A method as claimed in claim 4, which further includes:
indicating a fault in the event that it is determined in step (b) that an object has impinged upon the beam of light.

24. A method as claimed in claim 5, which further includes:

indicating a fault in the event that it is determined in step (b) that an object has impinged upon the beam of light.

* * * * *